US012570704B2

(12) United States Patent
Xie et al.

(10) Patent No.: US 12,570,704 B2
(45) Date of Patent: Mar. 10, 2026

(54) FUNCTIONALLY MODIFIED MAYTANSINOIDS AND COMPOSITIONS AND METHODS OF USE THEREOF

(71) Applicants: University of Georgia Research Foundation, Inc., Athens, GA (US); The University of North Carolina at Chapel Hill, Chapel Hill, NC (US)

(72) Inventors: Jin Xie, Athens, GA (US); Anil Kumar, Athens, GA (US); Zibo Li, Chapel Hill, NC (US)

(73) Assignees: University of Georgie Research Foundation, Inc., Athens, GA (US); The University of North Carolina at Chapel Hill, Chapel Hill, NC (US)

(*) Notice: Subject to any disclaimer, the term of this patent is extended or adjusted under 35 U.S.C. 154(b) by 896 days.

(21) Appl. No.: 17/774,843

(22) PCT Filed: Nov. 5, 2020

(86) PCT No.: PCT/US2020/059109

§ 371 (c)(1),
(2) Date: May 5, 2022

(87) PCT Pub. No.: WO2021/092172

PCT Pub. Date: May 14, 2021

(65) Prior Publication Data

US 2023/0023368 A1 Jan. 26, 2023

Related U.S. Application Data

(60) Provisional application No. 62/931,058, filed on Nov. 5, 2019.

(51) Int. Cl.

| | |
|---|---|
| ***C07D 498/18*** | (2006.01) |
| ***A61K 41/00*** | (2020.01) |
| ***A61K 47/69*** | (2017.01) |
| ***A61P 21/00*** | (2006.01) |
| ***A61P 25/14*** | (2006.01) |
| ***A61P 25/28*** | (2006.01) |
| ***A61P 35/00*** | (2006.01) |
| ***C07D 498/14*** | (2006.01) |
| ***C07K 14/47*** | (2006.01) |
| *A61K 38/00* | (2006.01) |

(52) U.S. Cl.

CPC ...... *C07K 14/4703* (2013.01); *A61K 41/0038* (2013.01); *A61K 47/6937* (2017.08); *A61P 21/00* (2018.01); *A61P 25/14* (2018.01); *A61P 25/28* (2018.01); *A61P 35/00* (2018.01); *C07D 498/18* (2013.01); *A61K 38/00* (2013.01)

(58) Field of Classification Search

CPC ........... C07K 14/4703; A61K 47/6937; A61K 38/00; A61K 41/0038; A61P 25/14; A61P 21/00; A61P 25/28; A61P 35/00; C07D 498/18; C07D 498/14

See application file for complete search history.

(56) References Cited

U.S. PATENT DOCUMENTS

| | | | |
|---|---|---|---|
| 4,256,746 | A | 3/1981 | Miyashita |
| 4,294,757 | A | 10/1981 | Asai |
| 4,307,016 | A | 12/1981 | Asai |
| 4,313,946 | A | 2/1982 | Powell |
| 4,315,929 | A | 2/1982 | Freedman |
| 4,322,348 | A | 3/1982 | Asai |
| 4,331,598 | A | 5/1982 | Hasegawa |
| 4,361,650 | A | 11/1982 | Asai |
| 4,362,663 | A | 12/1982 | Kida |
| 4,364,866 | A | 12/1982 | Asai |
| 4,371,533 | A | 2/1983 | Akimoto |
| 4,424,219 | A | 1/1984 | Hashimoto |
| 4,450,254 | A | 5/1984 | Isley |
| 5,475,092 | A | 12/1995 | Chari |
| 5,571,711 | A | 11/1996 | Van Der Bruggen |
| 5,585,499 | A | 12/1996 | Chari |
| 5,683,886 | A | 11/1997 | Van Der Bruggen |
| 5,846,545 | A | 12/1998 | Chari |
| 6,177,542 | B1 | 1/2001 | Ruoslahti |
| 6,333,410 | B1 | 12/2001 | Chari |
| 6,576,239 | B1 | 6/2003 | Ruoslahti |

(Continued)

FOREIGN PATENT DOCUMENTS

| | | |
|---|---|---|
| GB | 2241703 | 9/1991 |
| WO | 9640039 | 12/1996 |

(Continued)

OTHER PUBLICATIONS

Alimoradi , et al., "Nitric oxide-releasing nanoparticles improve doxorubicin anticancer activity", Int J Nanomedicine., vol. 13, Nov. 20, 2018, pp. 7771-7787.

(Continued)

*Primary Examiner* — Samantha L Shterengarts
(74) *Attorney, Agent, or Firm* — Pabst Patent Group LLP

(57) ABSTRACT

Radiosensitizer prodrugs and formulations and methods of use thereof are provided. Typically, the radiosensitizer prodrug is an analog of a radiosensitizer parent compound having one or more S-nitrosothiol moieties. Typically, the S—N bond of the S-nitrosothiol moiety can be cleaved by radiation during radiotherapy, releasing the parent compound and nitric oxide. One or preferably both the parent compound and the nitric oxide can contribute to death of tumor cells exposed to radiotherapy. Nanoparticle formulations for delivery of the prodrug, and methods of using them in combination with radiotherapy to treat tumors and cancer are also provided.

22 Claims, 16 Drawing Sheets

Specification includes a Sequence Listing.

(56) References Cited

U.S. PATENT DOCUMENTS

| | | | |
|---|---|---|---|
| 6,673,545 | B2 | 1/2004 | Faris |
| 6,677,157 | B1 | 1/2004 | Cohen |
| 6,699,475 | B1 | 3/2004 | Panicali |
| 7,544,767 | B2 | 6/2009 | Ruoslahti |
| 2009/0257951 | A1 | 10/2009 | Ruoslahti |
| 2010/0022680 | A1 | 1/2010 | Karnik |
| 2013/0029900 | A1 | 1/2013 | Widdison |
| 2016/0143914 | A1 | 5/2016 | Wang |
| 2017/0332910 | A1 | 11/2017 | Friedman |

FOREIGN PATENT DOCUMENTS

| | | |
|---|---|---|
| WO | 0050900 | 8/2000 |
| WO | 2009151744 A1 | 12/2009 |

OTHER PUBLICATIONS

Xu , et al., "A Switchable NO-releasing nanomedicine for enhanced cancer therapy and inhibition of metastasis", Nanoscale, vol. 11, No. 12, Feb. 22, 2019, pp. 5474-5488.
"Maytansine—An Overview", ScienceDirect1-10 (2019).
Adema, et al., "Molecular characterization of the melanocyte lineage-specific antigen gp100", J. Biol. Chem., 269:20126 (1994).
Alfthan, et al., "Elevation of free beta subunit of human choriogonadotropin and core beta fragment of human choriogonadotropin in the serum and urine of patients with malignant pancreatic and biliary disease", Cancer Res., 52(17):4628-33 (1992).
Alifano, et al., "Neurotensin receptor 1 determines the outcome of non-small cell lung cancer", Clinical Cancer Research, 16(17):4401-4410 (2010).
Ando, et al., "Ganglioside GM2 on the K562 cell line is recognized as a target structure by human natural killer cells", Int. J. Cancer, 40(1):12-17 (1987).
Arora, et al., "Alterations of tumor microvironment by nitric oxide impedes castration-resistant prostate cancer growth", PNAS, 115(44):11298-11303 (2018).
Azzam, et al., "Ionizing radiation-induced metabolic oxidative stress and prolonged cell injury", Cancer Lett., 327:48-60 (2012).
Baker et al., "A critical review of recent developments in radiotherapy for non-small cell lung cancer", Radiat. Oncol. 11:115 (2016).
Barnd, et al., "Specific, major histocompatibility complex-unrestricted recognition of tumor-associated mucins by human cytotoxic T cells", Proc. Nat. Acad. Sci. USA, 86:7159-7163 (1989).
Bast, et al., "A radioimmunoassay using a monoclonal antibody to monitor the course of epithelial ovarian cancer", N. Eng. J. Med., 309(15):883-7 (1983).
Bhattacharyya & Wolff, "Maytansine Binding to the Vinblastine Sites of Tubulin", Fees Lett., 75(1):159-162 (1977).
Biggs, et al., "Synthetic uses of S-Nitrosothiols in Organic Chemistry", 1-100 (2017).
Bloodsworth, et al., "Nitric oxide regulation of free radical- and enzyme-mediated lipid and lipoprotein oxidation", Arterioscler., Thromb., Vasc. Biol., 20:1707-1715 (2000).
Brown, et al., "Structural characterization of human melanoma-associated antigen p97 with monoclonal antibodies", J. Immunol., 127(2):539-46 (1981).
Cassady, et al., "Recent Developments in the Maytansinoid Antitumor Agents", Chem. Pharm. Bull., 52(1):1-26 (2004).
Chang, et al., "Characterization of the antigen (CAK1) recognized by monoclonal antibody K1 present on ovarian cancers and normal mesothelium", Cancer Res., 52(1):181-6 (1992a).
Chang, et al., "Frequent expression of the tumor antigen cak1 in squamous-cell carcinomas", Int. J. Cancer, 51(4):548-554 (1992c).
Chang, et al., "Isolation and characterization of a monoclonal antibody, K1, reactive with ovarian cancers and normal mesothelium", Int. J. Cancer, 50(3):373 (1992b).
Chang, et al., "Molecularcloningofmesothelin, adifferentiationantigenpresent onmesothelium, mesotheliomas, andovariancancers", Proc. Natl. Acad. Sci. USA, 93:136-140 (1996).
Cheng, et al., "Formulation of functionalized PLGA-PEG nanoparticles for in vivo targeted drug delivery", Biomaterials, 28(5):869-876 (2007).
Chowdhury, et al., "Isolation of a high-affinity stable single-chain Fv specific for mesothelin from DNA-immunized mice by phage display and construction of a recombinant immunotoxin with antitumor activity", Proc. Natl. Acad. Sci. USA, 95(2):669-674 (1998).
Dai, et al., "Encapsulating maytansinoid in pH-sensitive nanocarriers: The importance of using extremely potent cytotoxic agents and fast release for nanomedicine to achieve tumor elimination", NanoResearch, 1-8 (2019).
Datta, et al., "Sensitive detection of occult breast cancer by the reverse-transcriptase polymerase chain reaction", J. Clin. Oncol., 12(3):475-82 (1994).
Derman, et al., "Preparation, characterization and immunological evaluation: canine parvovirus synthetic peptide loaded PLGA nanoparticles", J Biomed Sci, 22:89 (2015).
Disis, et al., "Existent T-Cell and Antibody Immunity to HER-2/neu Protein in Patients with Breast Cancer", Canc. Res., 54:16-20 (1994).
Ferraz et al., Antitumor potential of S-nitrosothiol-containing polymeric nanoparticles against melanoma, Molecular Pharmaceutics, 2018 [retrieved on Jan. 2, 2021]. Retrieved from the Internet: < URL: https://www.research.ed.ac.uk/portal/en/publications/antitumor-potential-of-snitrosothiolcontaining-polymeric-nanoparticles-against-rnelanoma(5c0f1fd6-2e83-40b6-bc45-4aea4c9d547f).html>. pp. 1-29.
Fraszczak, et al., "Peroxynitrite-Dependent Killing of Cancer Cells and Presentation of Released Tumor Antigens by Activated Dendritic Cells ", J. Immunol., 184:1876-1884 (2010).
Gebauer, et al., "Tumor marker concentrations in normal and malignant tissues of colorectal cancer patients and their prognostic relevance", Anticancer Res., 17(4B):2939 (1997).
Gold and Freedman, "Demonstration of Tumor-Specific Antigens in Human Colonic Carcinomata by Immunological Tolerance and Absorption Techniques", J. Exp. Med., 121(3):439-62 (1985).
Hirokawa, et al., "Neuroblastoma in an adult with a high serum level of carbohydrate antigen, CA125: Report of a case", Surg. Today, 28:349 (1998).
Hoffman, et al., "Progressive vascular changes in a transgenic mouse model of squamous cell carcinoma", Cancer Cell, 4(5):383-391 (2003).
Hoon, et al., "Ganglioside GM2 expression on human melanoma cells correlates with sensitivity to lymphokine-activated killer cells", Int. J. Cancer, 43(5):857-62 (1989).
Huerta, "Nitric oxide donors: Novel cancer therapeutics (Review)", Int J of Oncol., 33:909-927 (2008).
International Search Report for PCT/US2020/059109 dated Mar. 12, 2021.
Jager, et al., "Antigen-Specific Immunotherapy and Cancer Vaccines", Int. J. Cancer, 106:817-20 (2003).
Jemal et al., "Cancer statistics, 2010", CA Cancer J. Clin., 60(5):277-300 (2010).
Karve, et al., "Revival of the abandoned therapeutic wortmannin by nanoparticle drug delivery", Proc. Natl. Acad. Sci. U. S. A., 109(21):8230-8235 (2012).
Kawakami, et al., "Cloningofthegenecodingforasharedhumanmelanomaantigenrecognizedbyautologous Tcellsinfiltratingintotumor", Proc. Nat. Acad. Sci. USA, 91:3515-2519 (1994).
Kennedy, et al., "A Role for Antibodies in Tumor Immunity", Int. Rev. Immunol., 22:141-72 (2003).
Korkmaz et al., "Molecular, genetic and epigenetic pathways of peroxynitrite-induced cellular toxicity", Interdiscip. Toxicol., 2:219-228 (2009).
Koshkaryev, et al., "Immunoconjugates and long circulating systems: origins, current state of the art and future directions", Adv. Drug. Deliv. Rev., 65(1):24-35 (2013).
Kudoh, et al., "Preoperative Determination of Several Serum Tumor Markers in Patients with Primary Epithelial Ovarian Carcinoma", Gynecol. Obstet. Invest., 47(1):52-57 (1999).

(56) References Cited

OTHER PUBLICATIONS

Kulhari, et al., "Peptide grafted and self-assembled poly(γ-glutamic acid)-phenylalanine nanoparticles targeting camptothecin to glioma", Nanomedicine, 12(14):1661-1674 (2017).
Kuncic & Lacombe, "Nanoparticle radio-enhancement: principles, progress and application to cancer treatment", Phys. Med. Biol., 63(2):02TR01 (2018).
Lehmann, et al., "Discrimination between benign and malignant cells of melanocytic lineage by two novel antigens, a glycoprotein with a molecular weight of 113,000 and a protein with a molecular weight of 76,000", Cancer Res., 47(3):841-45 (1987).
Lehmann, et al., "MUC18, a marker of tumor progression in human melanoma, shows sequence similarity to the neural cell adhesion molecules of the immunoglobulin superfamily", Proc. Natl. Acad. Sci. USA, 86(24):9891-95 (1989).
Lloyd, et al., "Isolation and Characterization of Ovarian Cancer Antigen CA 125 Using a New Monoclonal Antibody (VK-8): Identification as a Mucin-Type Molecule", Int. J. Canc., 71:842 (1997).
Lopus et al., "Maytansine and cellular metabolites of antibody-maytansinoid conjugates strongly suppress microtubule dynamics by binding to microtubules", Mol. Cancer Ther., 9(10):2689-99 (2010).
Lopus, "Antibody-DM1 conjugates as cancer therapeutics", Cancer Lett., 307(2):113-118 (2011).
McManus, et al., "Human chorionic gonadotropin in human neoplastic cells", Cancer Res., 36(9 PT 2):3476-81 (1976).
Meier, et al., "Prognostic significance of CA125 in patients with ovarian cancer and secondary debulking surgery", Anticancer Res., 17(4B):2945 (1997).
Miller, et al., "recent developments in nitric oxide donor drugs", Br. J. of Pharm., 151:305-321 (2007).
Moertel, et al., "Early clinical study of an intermittent schedule for maytansine (NSC-153858): brief communication", J. Natl. Cancer Inst., 60(1):93-96 (1978).
Moody, et al., "Neuropeptide G Protein-Coupled Receptors as Oncotargets", Front Endocrinol, 9:345 (2018).
Natali, et al., "Immunohistochemical detection of antigen in human primary and metastatic melanomas by the monoclonal antibody 140.240 and its possible prognostic significance", Cancer, 59(1):55-63 (1987).
Ng et al., "Inhibition of phosphatidylinositide 3-kinase enhances gemcitabine-induced apoptosis in human pancreatic cancer cells", Cancer Res. 60(19):20 5451-5455 (2000).
Oroudjev, et al., "Maytansinoid-Antibody Conjugates Induce Mitotic Arrest by Suppressing Microtubule Dynamic Instability", Mol. Cancer Ther., 9(10):2700-2713 (2010).
Otto et al., "Clinical Chemistry Reference Intervals for C57BL/6J, C57BL/6N, and C3HeB/FeJ Mice (Mus musculus)", J. Am. Assoc. Lab. Anim. Sci., 55(4):375-386 (2016).
Pacher et al., "Nitric Oxide and Peroxynitrite in Health and Disease", Physiol. Rev., 87:315-424 (2007).
Pant, et al., "Tunable Nitric Oxide Release from S-nitroso-Nacetylpenicillamine via Catalytic Copper Nanoparticles for Biomedical Applications", ACS Appl. Mater. Interfaces, 9:15254-15264 (2017).
Peddi & Hurvitz, "Ado-trastuzumab emtansine (T-DM1) in human epidermal growth factor receptor 2 (HER2)-positive metastatic breast cancer: latest evidence and clinical potential", Ther. Adv. Med. Oncol., 6(5):202-209 (2014).
Plowman, et al., "Heregulin induces tyrosine phosphorylation of HER4/p180erbB4", Nature, 366:473-475 (1993).
Ramroth, et al., "Dose and Fractionation in Radiation Therapy of Curative Intent for Non-Small Cell Lung Cancer: Meta-Analysis of Randomized Trials", Int. J. Radiat. Oncol., Biol. Phys., 96(4):736-747 (2016).
Raviraj, et al., "Radiosensitizers, radioprotectors, and radiation mitigators", Indian Journal of Dental Research, 25(1):83-90 (2014).
Rizi, "Nitric Oxide: The Forgotten Child of Tumor Metabolism", Trends Cancer, 3(9):659-672 (2017).
Rose, et al., "Primary structure of the human melanoma-associated antigen p97 (melanotransferrin) deduced from the mRNA sequence", Proc. Natl. Acad. Sci. USA, 83(5):1261-65 (1986).
Samstein, et al., "Theuseofdeoxycholicacidtoenhancetheoralbioavailabilityofbiodegradablenanoparticles", Biomaterials, 29(6):703-8 (2008).
Sarandakou, et al., "Tumour-associated antigens CEA, CA125, SCC and TPS in gynaecological cancer", Eur. J. Gynaecol. Oncol., 19(1):73-7 (1998).
Sarandakou, et al., "Vaginal fluid and serum CEA, CA125 and SCC in normal conditions and in benign and malignant diseases of the genital tract", Acta Oncol., 36(7):755 (1997).
Scanlan, et al., "The cancer/testis genes: review, standardization, and commentary", Cancer Immun., 4:1 (2004).
Szoka, et al., "Comparative Properties and Methods of Preparation of Lipid Vesicles (Liposomes)I", Annual review of biophysics and bioengineering, 9:467-508 (1980).
Tang, et al., "Role of metabolism in cancer cell radioresistance and radiosensitization methods", J. Exp. Clin. Canc. Res., 37(1):87 (2018).
Tian, et al., "Co-delivery of paclitaxel and cisplatin with biocompatible PLGA-PEG nanoparticles enhances chemoradiotherapy in non-small cell lung cancer models", J. Mater. Chem. B, 5(30):6049-6057 (2017).
Topalian, et al., "Human CD4+ T cells specifically recognize a shared melanoma-associated antigen encoded by the tyrosinase gene", Proc. Nat. Acad. Sci. USA, 91(20):9461-9465 (1994).
Trowbridge and Omary, "Human cell surface glycoprotein related to cell proliferation is the receptor for transferrin", Proc. Nat. Acad. USA, 78(5):3039-43 (1981).
Tsuchida, et al., "Gangliosides of human melanoma: GM2 and tumorigenicity", J. Natl. Cancer, 78(1):55-60 (1987a).
Tsuchida, et al., "Gangliosides of human melanoma", J. Natl. Cancer, 78(1):45-54 (1987b).
Tsuzuki, "Commercial scale production of inorganic nanoparticles", Int. J. Nanotechnol., 6(5/6):567-578 (2009).
Van den Bruggen, et al., "A gene encoding an antigen recognized by cytolytic T lymphocytes on a human melanoma", Science, 254(5038):1643-7 (1991).
Vijayasardahi, et al., "The melanoma antigen gp75 is the human homologue of the mouse b (brown) locus gene product", J. Exp. Med., 171(4):1375-80 (1990).
Wang, et al., "Nanoparticle formulations of histone deacetylase inhibitors for effective chemoradiotherapy in solid tumors", Biomaterials, 51:208-215 (2015).
Weber, et al., "Tumor Immunity and Autoimmunity Induced by Immunization with Homologous DNA", J. Clin. Invest, 102:1258 (1998).
Werner, et al., "Folate-targeted polymeric nanoparticle formulation of docetaxel is an effective molecularly targeted radiosensitizer with efficacy dependent on the timing of radiotherapy", ACS Nano, 5(11):8990-8998 (2011).
Wu, et al., "Facile Preparation of a Thiol-Reactive 18F-Labeling Agent and Synthesis of 18F-DEG-VS-NT for PET Imaging of a Neurotensin Receptor-Positive Tumor", J Nucl Med, 55(7):1178-84 (2014).
Yamaguchi, et al., "Human chorionic gonadotropin in colorectal cancer and its relationship to prognosis", Br. J. Cancer, 60(3):382-84 (1989).
Yin, et al., "Evaluation of neurotensin receptor 1 as a potential imaging target in pancreatic ductal adenocarcinoma", Amino Acids, 49(8): 1325-1335 (2017).
Yoshimura, et al., "Assessment of urinary beta-core fragment of human chorionic gonadotropin as a new tumor marker of lung cancer", Cancer, 73(11):2745-52 (1994).
Yoshino, et al., "Association of HER2/neu expression with sensitivity to tumor-specic CTL in human ovarian cancer", J. Immunol., 152(5):2393-2400 (1994).
Zhao et al., "Vascular nitric oxide: Beyond eNOS", J. Pharmacol. Sci., 129(2):83-94 (2015).
Chipinda and Simoyi, "Formation and stability of a nitric oxide donor: S-nitroso-N-acetylpenicillamine", J. Phys. Chem. B, 110(10):5052-5061 (2006).

(56) References Cited

OTHER PUBLICATIONS

Dupouy, “The potential use of the neurotensin high affinity receptor 1 as a biomarker for cancer progression and as a component of personalized medicine in selective cancers”, Biochimie, 93(9):1369-78 (2011).
Ewing, “Synergistic damage from H2O2 and OH radicals in irradiated cells”, Radiat. Res., 94(1):171-189 (1983).
Ferguson, et al., “The role of pro-drug therapy in the treatment of cancer”, Drug Resist. Updates, 4(4):225-232 (2001).
Hahn, et al., “A phase II study of radiation therapy (RT), paclitaxel poliglumex (PPX), and cetuximab (C) in locally advanced head and neck cancer (LA-HNC)”, J. Clin. Oncol., 31:6059-6059 (2013).
Hayabuchi, “Radiocurable tumors and non-radiocurable tumors”, JMAJ, 47(2): 79-83 (2004).
Jeyapalan, et al., “Paclitaxel poliglumex, temozolomide, and radiation for newly diagnosed high-grade glioma: a Brown University Oncology Group Study”, Am. J. Clin. Oncol., 37(5):444-449 (2014).
Kleczkowska and Lipkowski, “Neurotensin and neurotensin receptors: Characteristic, structure-activity relationship and pain modulation—A review”, European Journal of Pharmacology, 716(1-3): 54-60 (2013).
Kling, “Development of Covalent Ligand-Receptor Pairs to Study the Binding Properties of Nonpeptidic Neurotensin Receptor 1 Antagonists”, ACS Chem Biol, 11(4):869-75 (2016).
Nosrati, et al., “Tumor Targeted Albumin Coated Bismuth Sulfide Nanoparticles (Bi2S3) as Radiosensitizers and Carriers of Curcumin for Enhanced Chemoradiation Therapy”, Sci. Eng., 5(9):4416-4424 (2019).
Reinecke, et al., “Neurotensin. Immunohistochemical localization in central and peripheral nervous system and in endocrine cells and its functional role as neurotransmitter and endocrine hormone”. Prog Histochem Cytochem, 16(1):1-172 (1985).
Remillard, et al., “Antimitotic activity of the potent turnor inhibitor maytansine”, Science, 189(4207):1002-1005 (1975).
Riley, “Free Radicals in Biology: Oxidative Stress and the Effects of lonizing Radiation”, Int. J. Radiat. Biol. 65:27-33 (1994).
Rosenthal, et al., “Phase II study of maytansine in patients with advanced lymphomas: an Eastern Cooperative Oncology Group pilot study”, Cancer Treat. Rev., 64(10-11):1115-1117 (1980).
Schaeffer, “SR142948A is a Potent Antagonist of the Cardiovascular Effects of Neurotensin”, J Cardiovasc Pharmacol, 31(4):545-50 (1998).
Song et al., “Emerging Nanotechnology and Advanced Materials for Cancer Radiation Therapy”, Adv. Mater., 29(32):1700996 (2017).
Wang et al., “Enhanced Generation of Non-Oxygen Dependent Free Radicals by Schottky-type Heterostructurf Au-BI2S3 Nanoparticles via X-ray-Induced Catalytic Reaction for Radiosensitization”, ACS Nano, 13(5):5947-5958 (2019).
Wang, et al., “Cancer Radiosensitizers”, Trends Pharmacol. Sci., 39(1):24-48 (2018).
Wang, et al., “Nitric Oxide Donors: Chemical Activities and Biological Applications”, Chemical Reviews, 102:4, 1091-1134 (2002).
Yenjerla, et al., “Analysis of dynamic instability of steady-state microtubules in vitro by video-enhanced differential interference contrast microscopy with an appendix by Emin Oroudjev”, Methods Cell Biol., 95:189-206 (2010).

FUNCTIONALLY MODIFIED MAYTANSINOIDS AND COMPOSITIONS AND METHODS OF USE THEREOF

CROSS-REFERENCE TO RELATED APPLICATION

This application is a National Phase application under U.S.C. § 371 of PCT/US2020/059109, filed Nov. 5, 2020, which claims the benefit of and priority to U.S. Ser. No. 62/931,058 filed Nov. 5, 2019 and which are incorporated by reference herein in their entireties.

REFERENCE TO THE SEQUENCE LISTING

The Sequence Listing submitted as a text file named "UGA_2020_078_PCT_ST25" created on Oct. 26, 2020, and having a size of 2,105 bytes is hereby incorporated by reference pursuant to 37 C.F.R. § 1.52(e)(5).

FIELD OF THE INVENTION

The field of the invention generally relates to functionally modified maytansinoids, and compositions and methods of use thereof, particularly for the treatment of cancer.

BACKGROUND OF THE INVENTION

Radiotherapy (RT) remains a mainstay treatment option for cancer (Tang et al., *J. Exp. Clin. Canc. Res.* 37:87 (2018)). While new radiation delivery techniques (e.g. 3D conformal radiation therapy, intensity modulated radiation therapy, and image-guided radiation therapy) have been developed, the maximum radiation dose a patient can receive has barely changed (Ramroth et al., *Int. J. Radiat. Oncol., Biol., Phys.* 96, 736-747 (2016)). To improve treatment outcomes, radiosensitizers, agents that can enhance radiation toxicity at a given physical radiation dose, are often given during RT. These include chemotherapeutics such as 5-fluorouracil, anthracyclines, paclitaxel, and platinum, which are commonly used in concurrent to RT (i.e. chemoradiotherapy) (Ferguson et al., *Drug Resist. Updates* 4, 225-232 (2001)).

To improve bioavailability and reduce systemic toxicity, nanoparticle radiosensitizers have recently been developed and explored (Wang et al., *Trends Pharmacol. Sci.* 39, 24-48 (2018), Kuncic & Lacombe, *Phys. Med. Biol.* 63, 02TR01 (2018)). Unlike small molecule therapeutics, nanoparticles can selectively accumulate in tumors through the EPR effect and/or ligand-receptor interaction, thus reducing normal tissue exposure to toxins. For instance, therapeutics such as docetaxel (Werner et al., *ACS Nano* 5, 8990-8998 (2011)), wortmannin (Karve et al., *Proc. Natl. Acad. Sci. U.S.A* 109, 8230-8235 (2012)), and histone deacetylase inhibitors (Wang et al., *Biomaterials* 51, 208-215 (2015)), can be delivered by nanoparticle carriers to tumors to enhance RT. Polyglutamic acid conjugated paclitaxel nanoparticles, also known as Paclitaxel poliglumex (Xyotax), has been tested in the clinic to improve RT against glioma (Kulhari et al., *Nanomedicine* 12, 1661-1674 (2017), Jeyapalan et al., *Am. J. Clin. Oncol.* 37, 444-449 (2014)) and head and neck cancer (Hahn et al., *J. Clin. Oncol.* 31, 6059-6059 (2013)).

Despite these achievements, there remains a need for improved radiosensitizer compositions.

Thus, it is an object of the invention to provide improved radiosensitizer compounds, and formulations and methods of use thereof.

SUMMARY OF THE INVENTION

Radiosensitizer prodrugs and formulations and methods of use thereof are provided. Typically, the radiosensitizer prodrug is an analog of a radiosensitizer parent compound having one or more S-nitrosothiol moieties. Typically, the S—N bond of the S-nitrosothiol moieties can be cleaved by radiation during radiation therapy releasing the parent compound and nitric oxide. One, or preferably both, the parent compound and the nitric oxide can contribute to death of tumor cells exposed to the radiation. In preferred embodiments, the radiation is ionizing radiation, e.g., administered as radiotherapy. The compounds may also be used as sensitizers of phototherapy and/or proton therapy.

A preferred prodrug is a compound containing the structural motif:

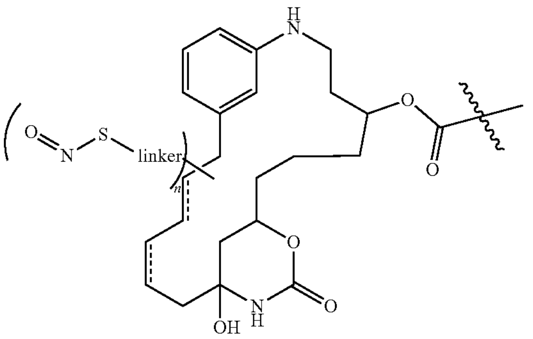

or

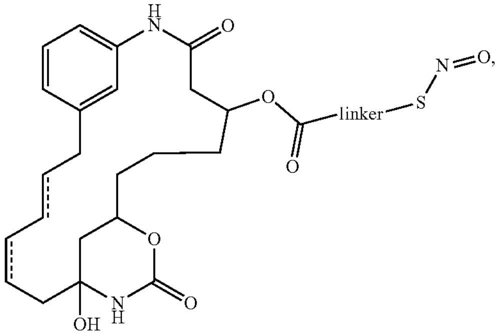

wherein:

n is an integer between 1 and 13, inclusive, the dashed lines indicate the presence or absence of a bond, and the corresponding carbon atoms have none, one, or two hydrogen atoms attached to each according to valency, and "linker" is, independently, absent, substituted amido, unsubstituted amido, substituted alkyl, substituted alkylene, unsubstituted alkylene, substituted aryl, substituted heteroaryl, substituted alkenyl, substituted alkynyl, substituted alkoxy, substituted aroxy, substituted alkylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, substituted polyaryl, substituted $C_3$-$C_{20}$ cyclic, or substituted $C_3$-$C_{20}$ heterocyclic.

In some embodiments, the compound has the structure:

Formula I

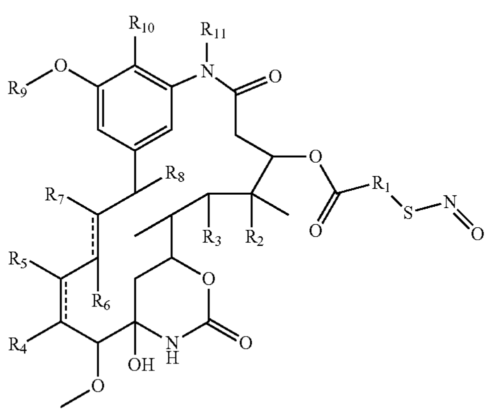

Formula I(a)

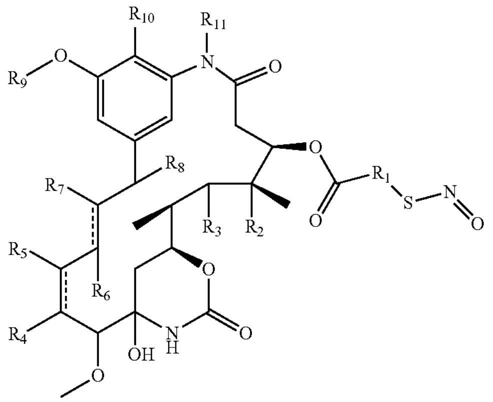

wherein:

$R_1$ is substituted amido, unsubstituted amido, substituted alkyl, substituted alkylene, unsubstituted alkylene, substituted aryl, substituted heteroaryl, substituted alkenyl, substituted alkynyl, substituted alkoxy, substituted aroxy, substituted alkylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, substituted polyaryl, substituted $C_3$-$C_{20}$ cyclic, or substituted $C_3$-$C_{20}$ heterocyclic, and $R_2$, $R_3$, $R_4$, $R_5$, $R_6$, $R_7$, $R_8$, $R_9$, $R_{10}$, and $R_{11}$ are independently hydrogen, halogen (F, Br, Cl, I), substituted alkyl, unsubstituted alkyl, substituted aryl, unsubstituted aryl, substituted heteroaryl, unsubstituted heteroaryl, unsubstituted alkenyl, substituted alkenyl, unsubstituted alkynyl, substituted alkynyl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic, or $R_2$ and $R_3$ together with the carbon atoms to which they are bonded an epoxide.

In some embodiments, $R_1$ is substituted C1-C10 amido, unsubstituted C1-C10 amido, substituted C1-C10 alkyl, unsubstituted C1-C10 alkylene, substituted C1-C10 alkylene, unsubstituted C1-C10 alkylene, substituted aryl, substituted heteroaryl, substituted C2-C10 alkenyl, substituted C2-C10 alkynyl, substituted C1-C10 alkoxy, substituted aroxy, substituted C1-C10 alkylthio, substituted arylthio, unsubstituted C1-C10 carbonyl, substituted C1-C10 carbonyl, unsubstituted C1-C10 carboxyl, substituted C1-C10 carboxyl, unsubstituted C1-C10 amino, substituted C1-C10 amino, unsubstituted C1-C10 sulfonyl, substituted C1-C10 sulfonyl, unsubstituted C1-C10 sulfamoyl, substituted C1-C10 sulfamoyl, unsubstituted C1-C10 phosphonyl, substituted C1-C10 phosphonyl, substituted polyaryl, substituted $C_3$-$C_{10}$ cyclic, or substituted $C_3$-$C_{10}$ heterocyclic, preferably wherein $R_1$ is substituted C1-C10 amido or unsubstituted C1-C10 amido.

In some embodiments, $R_1$ has the structure:

Formula II

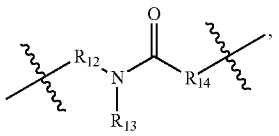

wherein $R_{12}$ is substituted C1-C5 alkylene or unsubstituted C1-C5 alkylene, $R_{12}$ is hydrogen, substituted C1-C5 alkyl, or unsubstituted C1-C5 alky, and $R_{14}$ is substituted C1-C5 alkylene or unsubstituted C1-C5 alkylene, preferably $R_{12}$ is substituted C1-C5 alkylene (preferably —$CH(CH_3)$—), $R_{12}$ is unsubstituted C1-C5 alkyl (preferably —$CH_3$), and $R_{14}$ is unsubstituted C1-C5 alkylene (preferably —$(CH_2)_2$—).

In some embodiments, the compound has a structure selected from:

Formula III

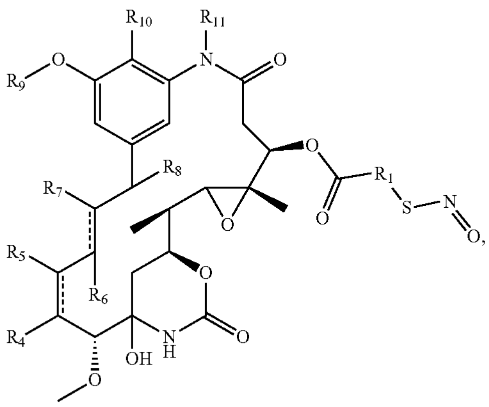

-continued
Formula IV
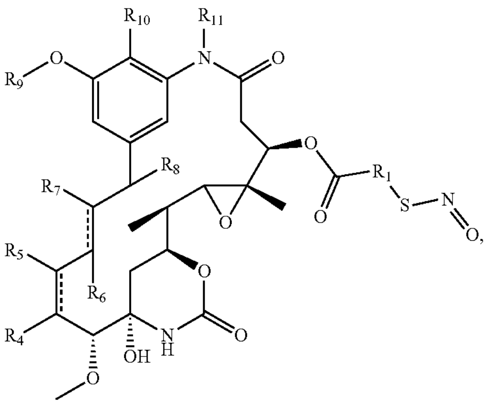
Formula V
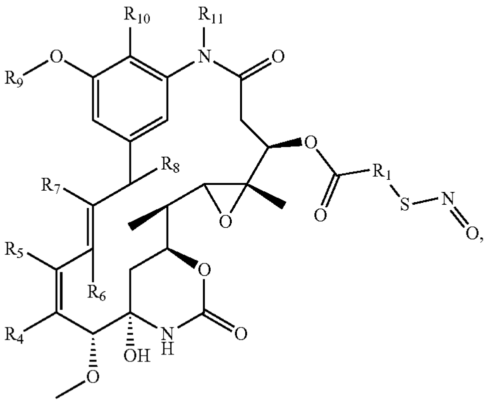
Formula VI
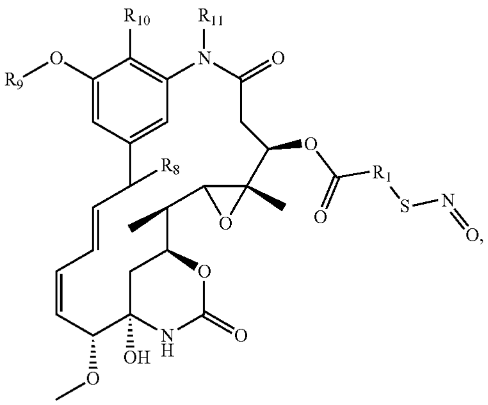
-continued
Formula VII
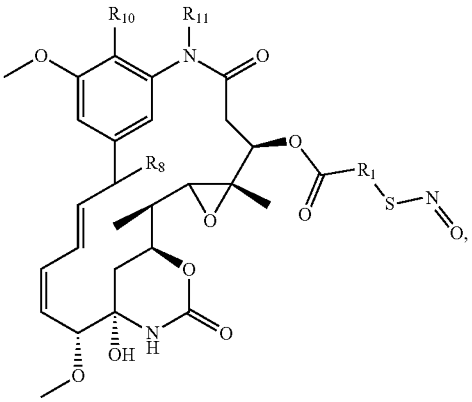
Formula VIII
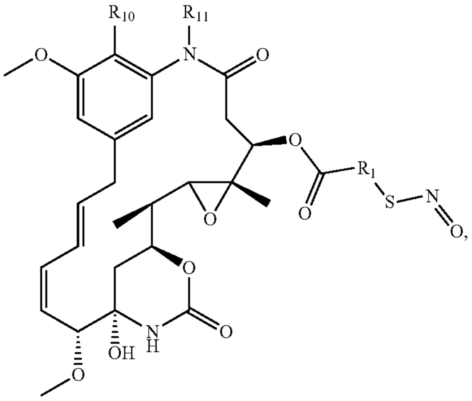
Formula IX
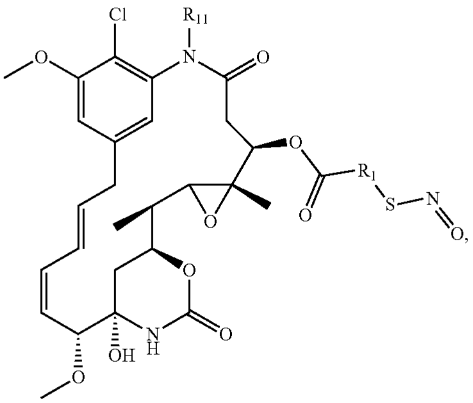
or -continued Formula X

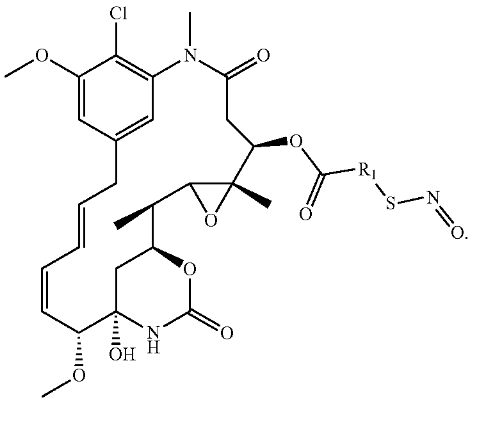

In some embodiments, when present $R_2$, $R_3$, $R_4$, $R_5$, $R_6$, $R_7$, $R_8$, $R_9$, $R_{10}$, and $R_{11}$ are independently hydrogen, hydroxy, halogen (F, Br, Cl, I), substituted C1-C5 alkyl, unsubstituted C1-C5 alkyl, substituted aryl, unsubstituted aryl, substituted heteroaryl, unsubstituted heteroaryl, unsubstituted C1-C5 alkenyl, substituted C1-C5 alkenyl, unsubstituted C1-C5 alkynyl, substituted C1-C5 alkynyl, unsubstituted C1-C5 alkoxy, substituted C1-C5 alkoxy, unsubstituted aroxy, substituted aroxy, unsubstituted C1-C5 alkylthio, substituted C1-C5 alkylthio, unsubstituted arylthio, substituted arylthio, unsubstituted C1-C5 carbonyl, substituted C1-C5 carbonyl, unsubstituted C1-C5 carboxyl, substituted C1-C5 carboxyl, unsubstituted C1-C5 amino, substituted C1-C5 amino, unsubstituted C1-C5 sulfonyl, substituted C1-C5 sulfonyl, unsubstituted C1-C5 sulfamoyl, substituted C1-C5 sulfamoyl, unsubstituted C1-C5 phosphonyl, substituted C1-C5 phosphonyl, unsubstituted polyaryl, substituted polyaryl, unsubstituted C3-C6 cyclic, substituted C3-C6 cyclic, unsubstituted C3-C6 heterocyclic, or substituted C3-C6 heterocyclic.

In some embodiments, when present $R_2$ and $R_3$ together with the carbon atoms to which they are bonded are an epoxide.

In some embodiments, when present $R_4$, $R_5$, $R_6$, and $R_7$ are independently hydrogen, hydroxy, halogen (F, Br, Cl, I), substituted C1-C5 alkyl, unsubstituted C1-C5 alkyl, substituted aryl, unsubstituted aryl, substituted heteroaryl, or unsubstituted heteroaryl, preferably, $R_4$, $R_5$, and $R_6$ are hydrogen, and $R_7$ is methyl.

In some embodiments, when present $R_8$ is hydrogen, hydroxy, halogen (F, Br, Cl, I), substituted C1-C5 carboxyl, unsubstituted C1-C5 carboxyl, substituted C1-C5 carbonyl, or unsubstituted C1-C5 carbonyl, preferably $R_8$ is hydrogen, hydroxy, substituted C1-C5 carboxyl, or unsubstituted C1-C5 carboxyl, or preferably $R_8$ is hydrogen.

In some embodiments, when present $R_9$ is hydrogen, substituted C1-C5 alkyl, unsubstituted C1-C5 alkyl, substituted C1-C5 carbonyl, or unsubstituted C1-C5 carbonyl, preferably $R_9$ is unsubstituted C1-C5 alkyl, or preferably $R_9$ is methyl.

In some embodiments, when present $R_{10}$ is a halogen (F, Cl, Br, I), substituted C1-C5 alkyl, unsubstituted C1-C5 alkyl, substituted C1-C5 carbonyl, or unsubstituted C1-C5 carbonyl, preferably $R_{10}$ is a halogen, or preferably $R_{10}$ is Cl.

In some embodiments, when present $R_{11}$ is hydrogen, substituted C1-C5 alkyl, unsubstituted C1-C5 alkyl, substituted aryl, unsubstituted aryl, substituted heteroaryl, or unsubstituted heteroaryl, preferably $R_{11}$ is unsubstituted C1-C5 alkyl, or preferably $R_{11}$ is methyl.

In a specific embodiment, the prodrug compound has the structure:

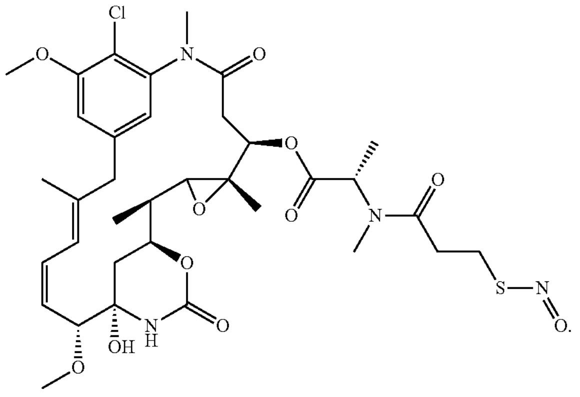 [SMILES: COc1cc2cc(c1Cl)N(C)C(=O)C[C@@H](OC(=O)[C@H](C)N(C)C(=O)CCSN=O)[C@]1(C)OC1[C@H](C)[C@@H]1C[C@@](O)(NC(=O)O1)[C@H](OC)/C=C\C=C(/C)C2]

Other radiosensitizer parent compounds can also be modified to include one or more S-nitrosothiol moieties. Such parent compounds include, but are not limited to, nicotinamide, metronidazole or an analog thereof, optionally selected from misoniszole, etanidazole, and nimorazole; a hypoxic cell cytotoxic agent, optionally selected from mitomycin-C and tirapazamine; a membrane active agent optionally selected from procaine, lidocaine, and chlorpromazine; a radiosensitizing nucleoside optionally selected from 5-fluorouracil, fluorodeoxyuridine bromodeoxyuridine, lododeoxyuridine, hydroxyurea, gemcitabine, and fludarabine, a texaphryin optionally selected from motexafin gadolinium; a suppressor of sulfhydral groups optionally selected from N-ethylmaleimide, diamide, and diethylmaleate; a chemotherapeutic agent optionally selected from paclitaxel, docetaxel, irinotecan, and cisplatin; pentoxifylline; vinorelbine; a PARP inhibitor; a histone deacetylase inhibitor; and a proteasome inhibitor.

In some embodiments, the prodrug is formulated with a nanoparticle delivery vehicle. The particles can be, for example, polymeric nanoparticles, liposomes, inorganic nanoparticles or proteins.

In some embodiments, the nanoparticles are polymeric nanoparticles formed of one or more amphiphilic, hydrophobic, and/or hydrophilic polymers.

For example, in some embodiments, the particles include one or more polyester hydrophobic polymers such as poly (lactic acid-co-glycolic acid), poly(lactic acid), and/or poly (glycolic acid). In particular embodiments the nanoparticles include poly(lactic acid-co-glycolic acid) (PLGA).

In some embodiments, the nanoparticles additionally or alternatively include one or more hydrophilic polymers. The hydrophilic polymers can be a polyalkylene glycol. In some embodiments, the nanoparticles include polyethylene glycol (PEG). In a specific embodiment, the nanoparticles are polymeric nanoparticles including poly(lactide-co-glycolic)-block-poly(ethylene glycol) (PLGA-b-PEG).

In some embodiments, the nanoparticles have a size or size distribution of about 10 nm to about 300 nm, or about 20 nm and about 200 nm. Additionally, or alternatively, the particles can have an average of any size between about 10 nm to about 300 nm, or about 20 nm and about 200 nm, or about 50 nm and about 150 nm, or about 50 nm and about 100 nm, or about 50 nm and about 75 nm. Typically, the particles are generally of a size or range of sizes suitable for delivery of the compound to tumor microenvironments, preferably by enhanced permeability and retention. In some embodiments, the nanoparticles have a targeting agent coupled thereto. For example, in some embodiments, the targeting agent targets NTSR1, typically by binding to Neurotensin receptor type 1 (NTSR1). The targeting agent can be an NTSR1 agonist or antagonist. In some embodiments, the targeting agent is neurotensin (NTS) or a variant or derivative thereof, such as $NTS_{mut}$. In other embodiments, the targeting agent is SR142948A or its derivatives.

Pharmaceutical compositions including an effective amount of the disclosed prodrug compound, and nanoparticle formulations thereof, are also provided.

Methods of using the compounds, nanoparticle formulations, and pharmaceutical compositions are also provided. For example, a method of treating a subject in need thereof can include administering the subject an effective amount of a disclosed prodrug compound or nanoparticle formulation thereof, preferably in a pharmaceutical composition. The subject can have a benign or malignant tumor. In preferred embodiments, the subject has cancer.

Typically, the subject is one that would benefit from a radiation-based therapy, including, but not limited to ionizing radiotherapy, phototherapy, or proton therapy. Thus, the methods can further including administering the subject one or more doses of ionizing radiation therapy, phototherapy, or proton therapy. Typically, a dose of ionizing, phototherapy or proton therapy radiation is administered (e.g., minute(s), hour(s), or day(s)) after administration of a pharmaceutical composition including the prodrug. For example, in exemplary embodiments, a dose of radiation is administered 1 hour to 48 hours, or 1 hour to 24 hours, or 1 hour to 12 hours, or 1 hour to 6 hours, or 2 hours to 6 hours, or 1, 2, 3, 4, or 5 hours after administration of the pharmaceutical composition. In some embodiments, 1, 2, 3, 4, or 5 rounds are radiation are administered after each single dose of the prodrug. In some embodiments, the prodrug is administered one or more times for each round of radiation. In some embodiments, each cycle of radiation is preceded by a cycle of prodrug. For example, in particular embodiments, 1, 2, 3, 4, 5, 6, 7, 8, 9, 10, or more rounds of administration of the pharmaceutical composition followed by administration of the dose of radiation are carried out in tandem.

Typically, the compound enhances the treatment of the cancer compared to administration of the radiation alone. In some embodiments, the cancer is a radiosensitive cancer. In other embodiments, the cancer is a radioresistant cancer. The cancer can be, for example, a vascular, bone, muscle, bladder, brain, breast, cervical, colo-rectal, esophageal, kidney, liver, lung, nasopharangeal, pancreatic, prostate, skin, stomach, uterine, or germ cell cancer. The cancer can be an epithelial cancer. In a specific embodiment, the cancer is a non-small cell lung cancer (NSCLC). In some embodiments, the cancer is composed of cells with upregulated NTSR1. Preferably, the same dose of radiation is more effective than when administered in the absence of the prodrug compound, a lower dose of radiation the same effectiveness as a higher dose when administered in the absence of the prodrug compound, or a combination thereof.

BRIEF DESCRIPTION OF THE DRAWINGS

FIGS. 3A and 3B show cytosolic and mitochondrial SOD activities: SOD levels in the absence of X-ray irradiation (3A), and SOD levels when cells were first incubated with DM1, DM1-NO, DM1-NPs, DM1-NO-NPs, or PBS, and then irradiated by X-ray (6 Gy) (3B). FIG. 3C shows intracellular OH radical level changes, assessed by MB assays. A decreased absorption at 664 nm indicates an increased ·OH level. All the cells received 6 Gy irradiation. FIG. 3D shows intracellular $^1O_2$, assessed by measuring SOSG fluorescence at 525 nm. All the cells received 6 Gy irradiation. The data were presented as mean±standard based on experiment results from at least three replicates. *P<0.05; P<0.01; *P<0.001; ns, no significant difference.

FIG. 8A is a series of photographic image of tumors from all treatment groups, dissected on Day 24. FIG. 8B is a graph showing the weight of the excised tumor masses from all treatment groups. FIG. 8C is a tumor growth curves. Significant tumor suppression was observed with animals in the DM1-NO-NPs+RT group. FIG. 8D is a body weight chart. No clear body weight drop was observed with animals in the DM1-NO-NPs+RT group. Scale bars, 50 μm. * P<0.05; P<0.01; *P<0.001; ns, no significant difference.

FIGS. 9A-9C are bar graphs showing red blood cell (RBC) and white blood cell (WBC) counts (9A), platelet counts (9B), and plateletcrit (PCT, mean platelet volume or platelet distribution width) counts (9C). ns, no significant difference. All the indices in 9A-9C were in the normal range.

FIGS. 10A-10C are bar graphs showing the results of blood biochemical analysis of alanine transaminase (ALT) and aspartate transaminase (AST) (10A), blood urea nitrogen (BUN) (10B), and creatinine (CR) (10C). FIGS. 10D and 10E are bar graphs showing liver tissue analysis of ALT (10D) and AST (10E) levels. FIG. 10F is a bar graph showing blood electrolyte levels (sodium, potassium, chloride, bicarbonate, glucose, calcium, inorganic phosphate, and magnesium. FIG. 10G is a bar graph showing total proteins, albumins, and lipids (cholesterol) levels in the blood. ns, no significant difference.

DETAILED DESCRIPTION OF THE INVENTION

I. Definitions

Figure 1A:
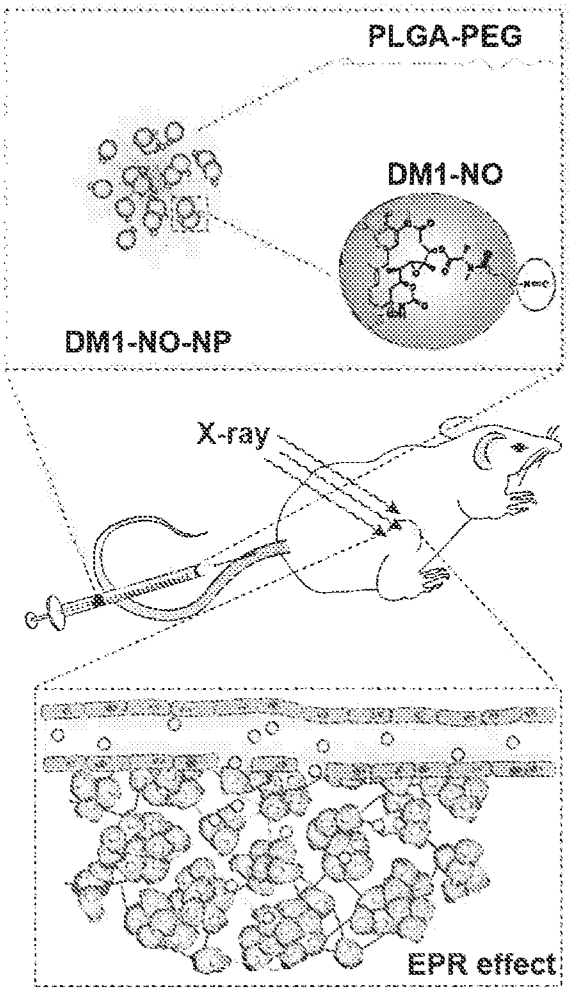
FIGS. 1A and 1B are schemes illustrating how DM1-NO encapsulated PLGA-b-PEG nanoparticles (DM1-NO-NPs) can accumulate in tumors through the EPR effect. In the presence of radiation and/or reduced pH in endosomes/lysosomes, the S—N bond was broken, releasing DM1 and NO. DM1 inhibits microtubule assembly, arresting cells at the more radiosensitive G2/M phase. Meanwhile, NO can react with ROS to form radicals such as peroxynitrites, causing DNA and lipid damages. The combined effects enhance the efficacy of RT.
Figure 1B:
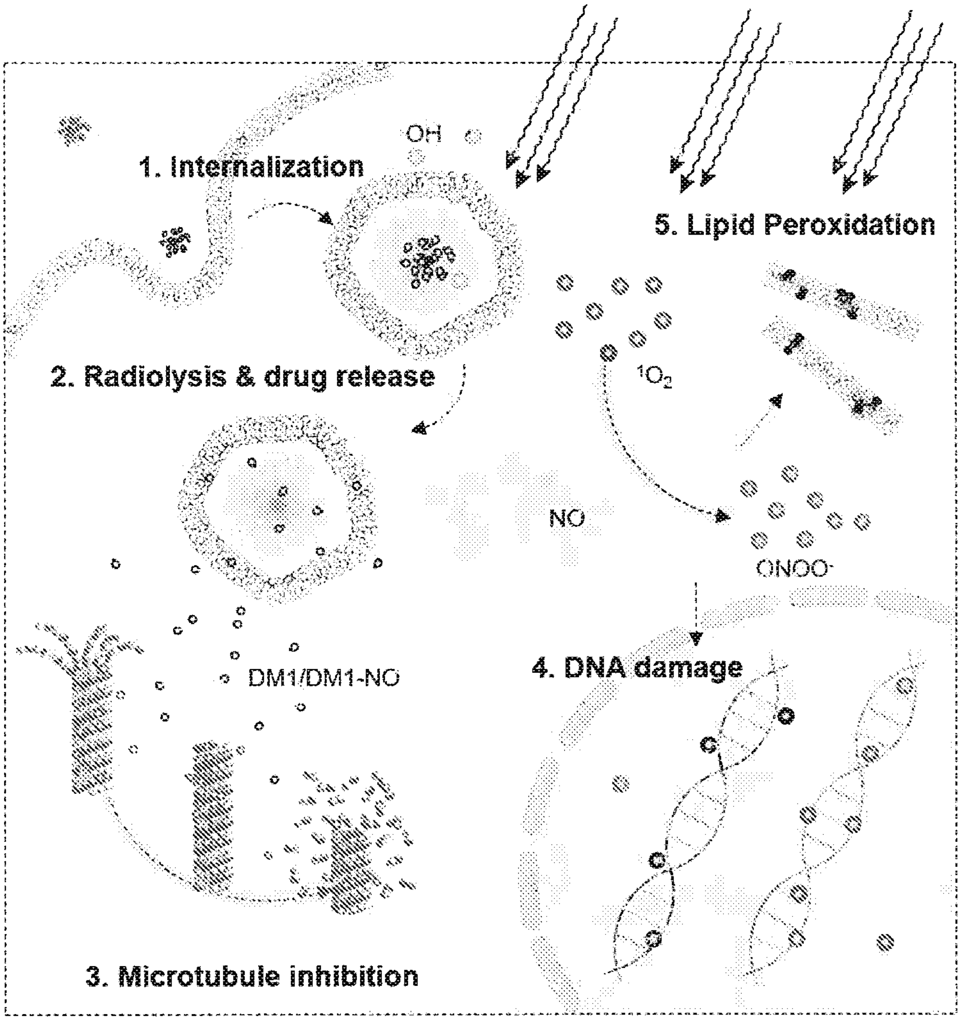

"Derivative" and "analog" are used interchangeably and, as relates to a given compound, refer to another compound or moiety that is structurally similar, functionally similar, or both, to the specified compound. Structural similarity can be determined using any criterion known in the art, such as the Tanimoto coefficient that provides a quantitative measure of similarity between two compounds based on their molecular descriptors. Preferably, the molecular descriptors are 2D properties such as fingerprints, topological indices, and maximum common substructures, or 3D properties such as overall shape, and molecular fields. Tanimoto coefficients range between zero and one, inclusive, for dissimilar and identical pairs of molecules, respectively. A compound can be considered a derivative or analog of a specified compound, if it has a Tanimoto coefficient with the specified compound between 0.5 and 1.0, inclusive, preferably between 0.7 and 1.0, inclusive, most preferably between 0.85 and 1.0, inclusive. A compound is functionally similar to a specified, if it induces the same effect as the specified compound. "Derivative" or "analog" can also refer to a modification including, but not limited to, hydrolysis, reduction, or oxidation products, of the compound or moiety. Hydrolysis, reduction, and oxidation reactions are known in the art.

The terms "inhibit" and "reduce" mean to reduce or decrease in activity or expression. This can be a complete inhibition or reduction of activity or expression, or a partial inhibition or reduction. Inhibition or reduction can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "nanoparticle" refers to any particle having a diameter greater than 1 nm and less than 1000 nm.

"Nitrosylated," "nitrosylation," "nitrosation," and related terms, is used to describe a structure, and does not limit the structure to one made from a specific starting material or by a particular synthetic route. Except where specifically and expressly provided to the contrary, the terms refer to a structural property, regardless of how the structure was formed, and the structure is not limited to a structure made by any specific method. The term as used to describe a structure herein, refers to organic compounds or moieties that contain a covalently bonded nitric oxide (NO) group. Where the nitric oxide is bonded, via its nitrogen atom, to a sulfur atom in the organic compounds, the organic compounds are generally referred to as "S-nitrosothiols," and contain the "—SNO" group referred to as an "S-nitrosothiol moiety."

The term "targeting agent" refers to a chemical compound that can direct a nanoparticle to a receptor site on a selected cell or tissue type, can serve as an attachment molecule, or serve to couple or attach another molecule. The term "direct," as relates to chemical compounds, refers to causing a nanoparticle to preferentially attach to a selected cell or tissue type. This targeting agent, generally binds to its receptor with high affinity and specificity.

"Treatment" and "treating", as used herein, refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

Except where specifically and expressly provided to the contrary, the term "substituted" refers to a structure, e.g., a chemical compound or a moiety on a larger chemical compound, regardless of how the structure was formed. The structure is not limited to a structure made by any specific method.

"Aryl," as used herein, refers to $C_5$-$C_{26}$-membered aromatic, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, for example, benzene, naphthalene, anthracene, phenanthrene, chrysene, pyrene, corannulene, coronene, etc.

"Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with an heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Alkyl," as used herein, refers to the radical of saturated aliphatic groups, including straight-chain alkyl, branched-chain alkyl, cycloalkyl (alicyclic), alkyl substituted cycloalkylgroups, and cycloalkyl substituted alkyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfoxide, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —$CON(R)_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as $—CF_3$, $—CH_2—CF_3$, $—CCl_3$); —CN; $—NCOCOCH_2CH_2$, —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl, sulfoxide, and sulfonate), and silyl groups, as well as ethers, alkylthios, carbonyls (including ketones, aldehydes, carboxylates, and esters), haloalkyls, —CN and the like. Cycloalkyls can be substituted in the same manner.

The terms "alkenyl" and "alkynyl" refer to unsaturated aliphatic groups analogous in length and possible substitution to the alkyls described above, but that contain at least one double or triple bond, respectively.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenyl" is art recognized, and refers to the aromatic moiety $—C_6H_5$, i.e., a benzene ring without one hydrogen atom.

The term "substituted phenyl" refers to a phenyl group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Amino" and "Amine," as used herein, are art-recognized and refer to both substituted and unsubstituted amines, e.g., a moiety that can be represented by the general formula:

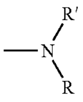
or
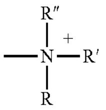

wherein, R, R', and R" each independently represent a hydrogen, substituted or unsubstituted alkyl, substituted or unsubstituted alkenyl, substituted or unsubstituted alkynyl, substituted or unsubstituted carbonyl, $—(CH_2)_m—R'''$, or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R") each independently represent a hydrogen atom, substituted or unsubstituted alkyl, a substituted or unsubstituted alkenyl, or $—(CH_2)_m—R'''$. Thus, the term 'alkylamine' as used herein refers to an amine group, as defined above, having a substituted or unsubstituted alkyl attached thereto (i.e. at least one of R, R', or R" is an alkyl group).

"Carbonyl," as used herein, is art-recognized and includes such moieties as can be represented by the general formula:

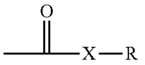
or
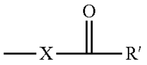

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $—(CH_2)_m—R''$, or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or $—(CH_2)_m—R''$; R" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

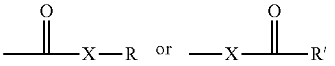

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "carboxyl" is as defined above for the formula

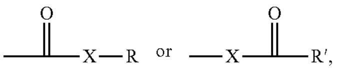

and is defined more specifically by the formula —$R^{iv}$COOH, wherein $R^{iv}$ is an alkyl, alkenyl, alkynyl, cycloalkyl, heterocyclyl, alkylaryl, arylalkyl, aryl, or heteroaryl. In preferred embodiments, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, wherein one or more hydrogen atoms in $R^{iv}$ are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

The terms "alkoxyl" or "alkoxy," "aroxy" or "aryloxy," generally describe compounds represented by the formula —$OR^v$, wherein $R^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O— alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenoxy" is art recognized, and refers to a compound of the formula —$OR^v$ wherein $R^v$ is (i.e., —O—$C_6H_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenylthio" is art recognized, and refers to —S—$C_6H_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Arylalkyl," as used herein, refers to an alkyl group that is substituted with a substituted or unsubstituted aryl or heteroaryl group.

"Alkylaryl," as used herein, refers to an aryl group (e.g., an aromatic or hetero aromatic group), substituted with a substituted or unsubstituted alkyl group.

The terms "amide" or "amido" are used interchangeably, refer to both "unsubstituted amido" and "substituted amido" and are represented by the general formula:

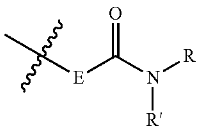

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' each independently represent a hydrogen atom, substituted or unsubstituted alkyl, a substituted or unsubstituted alkenyl, or —$(CH_2)_m$—R'''. When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

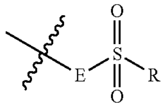

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of E and R can be substituted or unsubstituted amine, to form a "sulfonamide" or "sulfonamido." The substituted or unsubstituted amine is as defined above.

The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

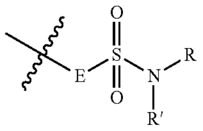

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R''$, or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide.

The term "sulfoxide" is represented by the formula

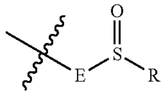

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "phosphonyl" is represented by the formula

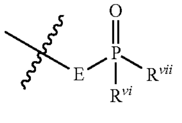

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, $R^{vi}$ and $R^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or R and R' taken together with the P atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "substituted phosphonyl" represents a phosphonyl in which E, $R^{vi}$ and $R^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phosphoryl" defines a phosphonyl in which E is absent, oxygen, alkoxy, aroxy, substituted alkoxy or substituted aroxy, as defined above, and independently of E, $R^{vi}$ and $R^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, $R^{vi}$ and $R^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof.

The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

The terms "hydroxyl" and "hydroxy" are used interchangeably and are represented by —OH.

The terms "cyano" and "nitrile" are used interchangeably to refer to —CN.

The term "phosphate" refers to $-O-PO_3$.

The term "azide" or "azido" are used interchangeably to refer to $-N_3$.

The term "substituted $C_1$-$C_x$ alkyl" refers to alkyl groups having from one to x carbon atoms, wherein at least one carbon atom is substituted, wherein "x" is an integer from one to ten. The term "unsubstituted $C_1$-$C_x$ alkyl" refers to alkyl groups having from one to x carbon atoms that are not substituted, wherein "x" is an integer from one to ten.

The term "substituted $C_1$-$C_x$ alkylene" refers to alkylene groups having from one to x carbon atoms, wherein at least one carbon atom is substituted, wherein "x" is an integer from one to ten. The term "unsubstituted $C_1$-$C_x$ alkylene" refers to alkylene groups having from one to x carbon atoms that are not substituted, wherein "x" is an integer from one to ten. The term "alkylene" as used herein, refers to a moiety with the formula $-(CH_2)_a-$, wherein "a" is an integer from one to ten.

The term "substituted $C_2$-$C_x$ alkenyl" refers to alkenyl groups having from two to x carbon atoms, wherein at least one carbon atom is substituted, wherein "x" is an integer from two to ten. The term "unsubstituted $C_2$-$C_x$ alkenyl" refers to alkenyl groups having from two to x carbon atoms that are not substituted, wherein "x" is an integer from two to ten.

The term "substituted $C_2$-$C_x$ alkynyl" refers to alkynyl groups having from two to x carbon atoms, wherein at least one carbon atom is substituted, wherein "x" is an integer from two to ten. The term "unsubstituted $C_2$-$C_x$ alkynyl" refers to alkynyl groups having from two to x carbon atoms that are not substituted, wherein "x" is an integer from two to ten.

The term "substituted $C_1$-$C_x$ alkoxy" refers to alkoxy groups having from one to x carbon atoms, wherein at least one carbon atom is substituted, wherein "x" is an integer from one to ten. The term "unsubstituted $C_1$-$C_x$ alkoxy" refers to alkoxy groups having from one to x carbon atoms that are not substituted, wherein "x" is an integer from one to ten.

The term "substituted $C_1$-$C_x$ alkylamino" refers to alkylamino groups having from one to x carbon atoms, wherein at least one carbon atom is substituted, wherein "x" is an integer from one to ten. The term "unsubstituted $C_1$-$C_x$ alkylamino" refers to alkyl groups having from one to x carbon atoms that are not substituted, wherein "x" is an integer from one to ten. The terms "alkylamine" and "alkylamino" are used interchangeably. In any alkylamino, where the nitrogen atom is substituted with one, two, or three substituents, the nitrogen atom can be referred to as a secondary, tertiary, or quaternary nitrogen atom, respectively.

The term "substituted $C_1$-$C_x$ alkylthio" refers to alkylthio groups having from one to x carbon atoms, wherein at least one carbon atom is substituted, wherein "x" is an integer from one to ten. The term "unsubstituted $C_1$-$C_x$ alkylthio" refers to alkylthio groups having from one to x carbon atoms that are not substituted, wherein "x" is an integer from one to ten.

The term "substituted $C_1$-$C_x$ carbonyl" refers to carbonyl groups having from one to x carbon atoms, wherein at least one carbon atom is substituted, wherein "x" is an integer from one to ten. The term "unsubstituted $C_1$-$C_x$ carbonyl" refers to carbonyl groups having from one to x carbon atoms that are not substituted, wherein "x" is an integer from one to ten.

The term "substituted $C_1$-$C_x$ carboxyl" refers to carboxyl groups having from one to x carbon atoms, wherein at least one carbon atom is substituted, wherein "x" is an integer from one to ten. The term "unsubstituted $C_1$-$C_x$ carboxyl" refers to carboxyl groups having from one to x carbon atoms that are not substituted, wherein "x" is an integer from one to ten.

The term "substituted $C_1$-$C_x$ amido" refers to amido groups having from one to x carbon atoms, wherein at least one carbon atom is substituted, wherein "x" is an integer from one to ten. The term "unsubstituted $C_1$-$C_x$ amido" refers to amido groups having from one to x carbon atoms that are not substituted, wherein "x" is an integer from one to ten.

The term "substituted $C_1$-$C_x$ sulfonyl" refers to sulfonyl groups having from one to x carbon atoms, wherein at least one carbon atom is substituted, wherein "x" is an integer from one to ten. The term "unsubstituted $C_1$-$C_x$ sulfonyl" refers to sulfonyl groups having from one to x carbon atoms that are not substituted, wherein "x" is an integer from one to ten.

The term "substituted $C_1$-$C_x$ sulfonic acid" refers to sulfonic acid groups having from one to x carbon atoms, wherein at least one carbon atom is substituted, wherein "x" is an integer from one to ten. The term "unsubstituted $C_1$-$C_x$ sulfonic acid" refers to sulfonic acid groups having from one to x carbon atoms that are not substituted, wherein "x" is an integer from one to ten.

The term "substituted $C_1$-$C_x$ sulfamoyl" refers to sulfamoyl groups having from one to x carbon atoms, wherein at least one carbon atom is substituted, wherein "x" is an integer from one to ten. The term "unsubstituted $C_1$-$C_x$ sulfamoyl" refers to sulfamoyl groups having from one to x carbon atoms that are not substituted, wherein "x" is an integer from one to ten.

The term "substituted $C_1$-$C_x$ sulfoxide" refers to sulfoxide groups having from one to x carbon atoms, wherein at least one carbon atom is substituted, wherein "x" is an integer from one to ten. The term "unsubstituted $C_1$-$C_x$ sulfoxide" refers to sulfoxide groups having from one to x carbon atoms that are not substituted, wherein "x" is an integer from one to ten.

The term "substituted $C_1$-$C_x$ phosphoryl" refers to phosphoryl groups having from one to x carbon atoms, wherein at least one carbon atom is substituted, wherein "x" is an integer from one to ten. The term "unsubstituted $C_1$-$C_x$ phosphoryl" refers to phosphoryl groups having from one to x carbon atoms that are not substituted, wherein "x" is an integer from one to ten.

The term "substituted $C_1$-$C_x$ phosphonyl" refers to phosphonyl groups having from one to x carbon atoms, wherein at least one carbon atom is substituted, wherein "x" is an integer from one to ten. The term "unsubstituted $C_1$-$C_x$ phosphonyl" refers to phosphonyl groups having from one to x carbon atoms that are not substituted, wherein "x" is an integer from one to ten.

The term "substituted $C_0$-$C_x$ sulfonyl" refers to sulfonyl groups having from zero to x carbon atoms, wherein, if present, at least one carbon atom is substituted, wherein "x" is an integer from zero to ten. The term "unsubstituted $C_0$-$C_x$ sulfonyl" refers to sulfonyl groups having from zero to x carbon atoms that are not substituted, wherein "x" is an integer from zero to ten.

The term "substituted $C_0$-$C_x$ sulfonic acid" refers to sulfonic acid groups having from zero to x carbon atoms, wherein, if present, at least one carbon atom is substituted, wherein "x" is an integer from zero to ten. The term "unsubstituted $C_0$-$C_x$ sulfonic acid" refers to sulfonic acid groups having from zero to x carbon atoms that are not substituted, wherein "x" is an integer from zero to ten.

The term "substituted $C_0$-$C_x$ sulfamoyl" refers to sulfamoyl groups having from zero to x carbon atoms, wherein, if present, at least one carbon atom is substituted, wherein "x" is an integer from zero to ten. The term "unsubstituted $C_0$-$C_x$ sulfamoyl" refers to sulfamoyl groups having from zero to x carbon atoms that are not substituted, wherein "x" is an integer from zero to ten.

The term "substituted $C_0$-$C_x$ sulfoxide" refers to sulfoxide groups having from zero to x carbon atoms, wherein at least one carbon atom is substituted, wherein "x" is an integer from zero to ten. The term "unsubstituted $C_0$-$C_x$ sulfoxide" refers to sulfoxide groups having from zero to x carbon atoms that are not substituted, wherein "x" is an integer from zero to ten.

The term "substituted $C_0$-$C_x$ phosphoryl" refers to phosphoryl groups having from zero to x carbon atoms, wherein, if present, at least one carbon atom is substituted, wherein "x" is an integer from zero to ten. The term "unsubstituted $C_0$-$C_x$ phosphoryl" refers to phosphoryl groups having from zero to x carbon atoms that are not substituted, wherein "x" is an integer from zero to ten.

The term "substituted $C_0$-$C_x$ phosphonyl" refers to phosphonyl groups having from zero to x carbon atoms, wherein, if present, at least one carbon atom is substituted, wherein "x" is an integer from zero to ten. The term "unsubstituted $C_0$-$C_x$ phosphonyl" refers to phosphonyl groups having from zero to x carbon atoms that are not substituted, wherein "x" is an integer from zero to ten.

The terms substituted "$C_x$ alkyl," "$C_x$ alkylene," "$C_x$ alkenyl," "$C_x$ alkynyl," "$C_x$ alkoxy," "$C_x$ alkylamino," "$C_x$ alkylthio," "$C_x$ carbonyl," "$C_x$ carboxyl," "$C_x$ amido," "$C_x$ sulfonyl," "$C_x$ sulfonic acid," "$C_x$ sulfamoyl," "$C_x$ phosphoryl," and "$C_x$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms, wherein at least one carbon atom is substituted, wherein "x" is an integer from one to ten. The terms unsubstituted "$C_x$ alkyl," "$C_x$ alkylene," "$C_x$ alkenyl," "$C_x$ alkynyl," "$C_x$ alkoxy," "$C_x$ alkylamino", "$C_x$ alkylthio," "$C_x$ carbonyl," "$C_x$ carboxyl," "$C_x$ amido," "$C_x$ sulfonyl," "$C_x$ sulfonic acid," "$C_x$ sulfamoyl," "$C_x$ phosphoryl," and "$C_x$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms that are not substituted, wherein "x" is an integer from one to ten.

The terms unsubstituted "$C_0$ sulfonyl," "$C_0$ sulfonic acid," "$C_0$ sulfamoyl," "$C_0$ phosphoryl," and "$C_0$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having zero carbon atoms that are not substituted.

"Halogen," as used herein, refers to fluorine, chlorine, bromine, or iodine.

The term "radiosensitivity" refers to the relative susceptibility of cells to the harmful effect of ionizing radiation. The more radiosensitive a cell is, the less radiation that is required to kill that cell. In general, it has been found that cell radiosensitivity is directly proportional to the rate of cell division and inversely proportional to the cell's capacity for DNA repair.

The term "radioresistant" refers to a cell that does not die when exposed to clinically suitable dosages of ionizing radiation.

The term "neoplastic cell" refers to a cell undergoing abnormal cell proliferation ("neoplasia"). The growth of neoplastic cells exceeds and is not coordinated with that of the normal tissues around it. The growth typically persists in the same excessive manner even after cessation of the stimuli, and typically causes formation of a tumor.

The term "tumor" or "neoplasm" refers to an abnormal mass of tissue containing neoplastic cells. Neoplasms and tumors may be benign, premalignant, or malignant.

The term "cancer" or "malignant neoplasm" refers to a cell that displays uncontrolled growth, invasion upon adjacent tissues, and often metastasis to other locations of the body.

The term "antineoplastic" refers to a composition, such as a drug or biologic, that can inhibit or prevent cancer growth, invasion, and/or metastasis.

The term "individual," "host," "subject," and "patient" are used interchangeably to refer to any individual who is the target of administration or treatment. The subject can be a vertebrate, for example, a mammal. Thus, the subject can be a human or veterinary patient.

The term "therapeutically effective" means that the amount of the composition used is of sufficient quantity to ameliorate one or more causes or symptoms of a disease or disorder. Such amelioration only requires a reduction or alteration, not necessarily elimination. A therapeutically effective amount of a composition for treating cancer is preferably an amount sufficient to cause tumor regression or to sensitize a tumor to radiation or chemotherapy.

The term "pharmaceutically acceptable" refers to a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

II. Compositions

Described are compounds containing one or more S-nitrosothiol moieties and/or nanoparticles encapsulating these compounds. The compounds can sensitize cancer cells to radiation therapy. In some forms, the compounds are maytansinoid analogs. In some forms, the compounds include a compound having the structure shown below:

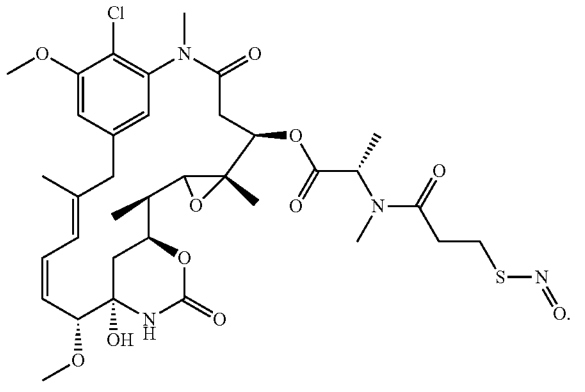 [SMILES: COc1cc2cc(c1Cl)N(C)C(=O)C[C@@H](OC(=O)[C@H](C)N(C)C(=O)CCSN=O)[C@]1(C)OC1[C@H](C)[C@@H]1C[C@@](O)(NC(=O)O1)[C@H](OC)/C=C\C=C(/C)C2]

In some forms, these compounds can be encapsulated in nanoparticles, on the surfaces of nanoparticles, or both. In some forms, the compounds can be encapsulated in nanoparticles. In some forms, the compounds can be on the surfaces of nanoparticles. The compounds can be covalently or non-covalently conjugated to the nanoparticles. In some forms, the compounds can be encapsulated within the nanoparticles and are non-covalently conjugated to the nanoparticles. In some forms, the compounds can be on the surfaces of the nanoparticles and are covalently conjugated to the surfaces of the nanoparticles. The nanoparticles can be polymeric nanoparticles, liposomes, or inorganic nanoparticles.

In some forms, the nanoparticles are polymeric nanoparticles. In some forms, the polymeric nanoparticles contain an amphiphilic copolymer. In some forms, the amphiphilic polymer contains a polyester (such as a poly(hydroxy acid) and a polyalkylene oxide (such as polyethylene glycol). In some forms, the amphiphilic polymer contains poly(lactic acid-co-glycolic acid)-polyethylene glycol. In some forms, the nanoparticles have a size between about 50 nm and about 150 nm, such as about 78 nm. Optionally, the nanoparticles contain a targeting agent.

The ensuing paragraphs include further details about the compounds, nanoparticles, and components that can be included in the nanoparticles.

A. Compounds

Compound for use in combination with radiotherapy are provided. The compounds contain one or more S-nitrosothiol moieties. The compounds are prodrug compounds designed such that when exposed to radiation, preferably ionizing radiation, during radiotherapy, the S—N bond is cleaved, releasing the parent compound and nitric oxide.

Typically, the parent compound is chemotherapeutic and/or radiosensitizer, and the one or more S-nitrosothiol moieties suppress toxicity of the prodrug form of the compound relative to the un-nitrosylated parent compound, the nitric oxide released from the prodrug when the S—N bond is cleaved elevates oxidative stress in cells, or a combination thereof.

In some embodiments, the parent compound, and thus the compound released from nitric oxide when the S—N bond is cleaved, is an inhibitor of microtubule polymerization.

In some forms, the compounds can include a structural motif shown below:

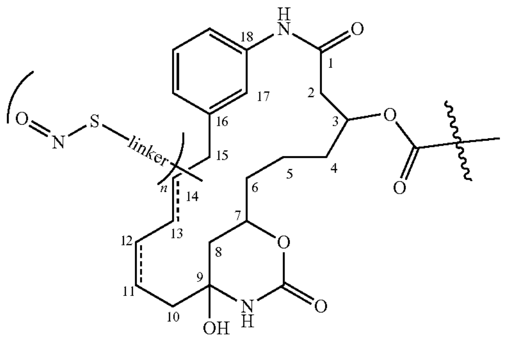

or

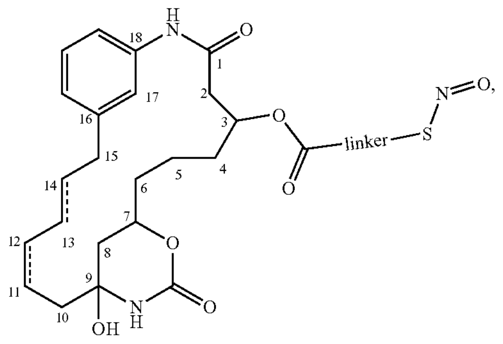

wherein the numerals primarily serve the purpose of nomenclature. The dashed lines between positions 11 and 12, and 13 and 14 indicate that a bond can be absent or present, and the carbon atoms at positions 11, 12, 13, and 14 have none, one, or two hydrogen atoms attached to each according to valency. n is an integer between 1 and 13, inclusive, such as 1, 2, 3, 4, 5, 6, 7, 8, 9, 10, 11, 12, 13. "Linker" is, independently, absent, substituted amido, unsubstituted amido, substituted alkyl, substituted alkylene, unsubstituted alkylene, substituted aryl, substituted heteroaryl, substituted alkenyl, substituted alkynyl, substituted alkoxy, substituted aroxy, substituted alkylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, substituted polyaryl, substituted $C_3$-$C_{20}$ cyclic, or substituted $C_3$-$C_{20}$ heterocyclic. "Linker" can also be substituted $C_1$-$C_{10}$ amido, unsubstituted $C_1$-$C_{10}$ amido, substituted $C_1$-$C_{10}$ alkyl, unsubstituted $C_1$-$C_{10}$ alkylene, substituted $C_1$-$C_{10}$ alkylene, unsubstituted $C_1$-$C_{10}$ alkylene, substituted aryl, substituted heteroaryl, substituted $C_2$-$C_{10}$ alkenyl, substituted $C_2$-$C_{10}$ alkynyl, substituted $C_1$-$C_{10}$ alkoxy, substituted aroxy, substituted $C_1$-$C_{10}$ alkylthio, substituted arylthio, unsubstituted $C_1$-$C_{10}$ carbonyl, substituted $C_1$-$C_{10}$ carbonyl, unsubstituted $C_1$-$C_{10}$ carboxyl, substituted $C_1$-$C_{10}$ carboxyl, unsubstituted $C_1$-$C_{10}$ amino, substituted $C_1$-$C_{10}$ amino, unsubstituted $C_1$-$C_{10}$ sulfonyl, substituted $C_1$-$C_{10}$ sulfonyl, unsubstituted $C_1$-$C_{10}$ sulfamoyl, substituted $C_1$-$C_{10}$ sulfamoyl, unsubstituted $C_1$-$C_{10}$ phosphonyl, substituted $C_1$-$C_{10}$ phosphonyl, substituted polyaryl, substituted $C_3$-$C_{10}$ cyclic, or substituted $C_3$-$C_{10}$ heterocyclic.

Maytansinoids are macrolides that can suppress the proliferation of cancer cells at sub-nanomolar concentrations, making them 100- to 1000-times more efficient than cisplatin (Lopus, *Cancer Lett.* 307, 113-118 (2011), Remillard et al., *Science* 189, 1002-1005 (1975)). Maytansinoids kill cancer cells by inhibiting microtubule assembly (Oroudjev et al., *Mol. Cancer Ther.* 9, 2700-2713 (2010)). This antimitotic effect may enrich cells at the mitotic phase, which is more sensitive to RT (Lopus et al., *Mol. Cancer Ther.* 9, 2689-2699 (2010), Yenjerla et al., *Methods Cell Biol.* 95, 189-206 (2010)). However, maytansine failed as an anticancer agent in clinical trials due to its lack of specificity and unacceptable systemic toxicity (Moertel et al., *J. Natl. Cancer Inst.* 60, 93-96 (1978), Rosenthal et al., *Cancer Treat. Rev.* 64, 1115-1117 (1980), Lopus et al., *Mol. Cancer Ther.* 9, 2689-99 (2010)). Recent developments in antibody-drug conjugates (ADC) permitted the delivery of maytansinoids, in particular DM1, to cancer cells with more favorable pharmacokinetics and pharmacodynamics (Lopus, *Cancer Lett.* 307, 113-8 (2011)). Kadcyla, a DM1-trastuzumab conjugate, can sensitize breast cancer cells to RT (Peddi &Hurvitz, *Ther. Adv. Med. Oncol.* 6, 202-209 (2014), Koshkaryev et al., *Adv. Drug. Deliv. Rev.* 65, 24-35 (2013)), confirming the potential of maytansinoids as a radiosensitizer if delivered selectively to tumors.

The experiments below show that S-nitrosylation of the maytansinoid DM1 can help suppress toxicity, allowing the drug to be delivered to tumors through the enhanced permeability and retention (EPR) effect. Under irradiation to tumors, the oxidative stress is elevated, leading to the cleavage of the S—N bond, and the release of DM1 and nitric oxide (NO). DM1 inhibits microtubule polymerization and enriches cells at the G2/M phase, which is more radiosensitive. NO under irradiation forms highly toxic radicals such as peroxynitrites, which also contribute to tumor suppression. The two components work additively or more than additively to enhance radiotherapy outcomes, which was confirmed in vitro by clonogenic assays and in vivo with H1299 tumor bearing mice.

Thus, in some forms, the compounds are maytansinoids or maytansinoid analogs containing one or more S-nitrosothiol moieties.

Examples of suitable maytansinoid analogs include those having a modified aromatic ring and/or those having modifications at other positions. Such maytansinoids are described in, for example, U.S. Pat. Nos. 4,256,746, 4,294,757, 4,307,016, 4,313,946, 4,315,929, 4,322,348, 4,331,598, 4,361,650, 4,362,663, 4,364,866, 4,424,219, 4,371,533, 4,450,254, 5,475,092, 5,585,499, 5,846,545, and 6,333,410.

In some forms, the compounds have the structure:

Formula I

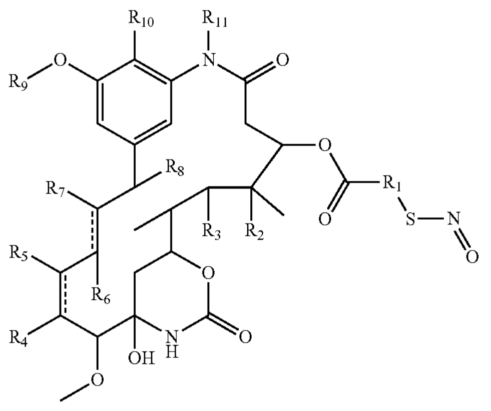

Formula I(a)

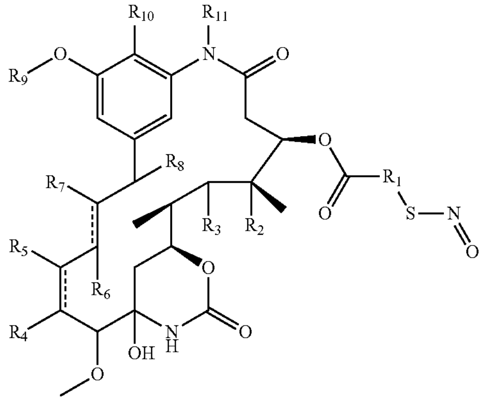

wherein:

the dashed lines between positions 11 and 12, and 13 and 14 indicate that a bond can be absent or present, and the carbon atoms at positions 11, 12, 13, and 14 have none, one, or two hydrogen atoms attached to each according to valency, $R_1$ is substituted amido, unsubstituted amido, substituted alkyl, substituted alkylene, unsubstituted alkylene, substituted aryl, substituted heteroaryl, substituted alkenyl, substituted alkynyl, substituted alkoxy, substituted aroxy, substituted alkylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, substituted polyaryl, substituted $C_3$-$C_{20}$ cyclic, or substituted $C_3$-$C_{20}$ heterocyclic, and $R_2$, $R_3$, $R_4$, $R_5$, $R_6$, $R_7$, $R_8$, $R_9$, $R_{10}$, and $R_{11}$ are independently hydrogen, halogen (F, Br, Cl, I), substituted alkyl, unsubstituted alkyl, substituted aryl, unsubstituted aryl, substituted heteroaryl, unsubstituted heteroaryl, unsubstituted alkenyl, substituted alkenyl, unsubstituted alkynyl, substituted alkynyl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic, or $R_2$ and $R_3$ together with the carbon atoms to which they are bonded an epoxide.

In some forms of Formula I or Formula I(a), $R_1$ is substituted $C_1$-$C_{10}$ amido, unsubstituted $C_1$-$C_{10}$ amido, substituted $C_1$-$C_{10}$ alkyl, unsubstituted $C_1$-$C_{10}$ alkylene, substituted $C_1$-$C_{10}$ alkylene, unsubstituted $C_1$-$C_{10}$ alkylene, substituted aryl, substituted heteroaryl, substituted $C_2$-$C_{10}$ alkenyl, substituted $C_2$-$C_{10}$ alkynyl, substituted $C_1$-$C_{10}$ alkoxy, substituted aroxy, substituted $C_1$-$C_{10}$ alkylthio, substituted arylthio, unsubstituted $C_1$-$C_{10}$ carbonyl, substituted $C_1$-$C_{10}$ carbonyl, unsubstituted $C_1$-$C_{10}$ carboxyl, substituted $C_1$-$C_{10}$ carboxyl, unsubstituted $C_1$-$C_{10}$ amino, substituted $C_1$-$C_{10}$ amino, unsubstituted $C_1$-$C_{10}$ sulfonyl, substituted $C_1$-$C_{10}$ sulfonyl, unsubstituted $C_1$-$C_{10}$ sulfamoyl, substituted $C_1$-$C_{10}$ sulfamoyl, unsubstituted $C_1$-$C_{10}$ phosphonyl, substituted $C_1$-$C_{10}$ phosphonyl, substituted polyaryl, substituted $C_3$-$C_{10}$ cyclic, or substituted $C_3$-$C_{10}$ heterocyclic.

In some forms of Formula I or Formula I(a), $R_1$ is substituted $C_1$-$C_5$ amido, unsubstituted $C_1$-$C_5$ amido, substituted $C_1$-$C_8$ alkyl, substituted $C_1$-$C_5$ alkylene, unsubstituted $C_1$-$C_8$ alkylene, substituted aryl, substituted heteroaryl, substituted $C_2$-$C_5$ alkenyl, substituted $C_2$-$C_5$ alkynyl, substituted $C_1$-$C_5$ alkoxy, substituted aroxy, substituted $C_1$-$C_8$ alkylthio, substituted arylthio, unsubstituted $C_1$-$C_5$ carbonyl, substituted $C_1$-$C_5$ carbonyl, unsubstituted $C_1$-$C_5$ carboxyl, substituted $C_1$-$C_5$ carboxyl, unsubstituted $C_1$-$C_5$ amino, substituted $C_1$-$C_5$ amino, unsubstituted $C_1$-$C_5$ sulfonyl, substituted $C_1$-$C_5$ sulfonyl, unsubstituted $C_1$-$C_5$ sulfamoyl, substituted $C_1$-$C_5$ sulfamoyl, unsubstituted $C_1$-$C_5$ phosphonyl, substituted $C_1$-$C_5$ phosphonyl, substituted polyaryl, substituted $C_3$-$C_6$ cyclic, or substituted $C_3$-$C_6$ heterocyclic.

In some forms of Formula I or Formula I(a), $R_1$ is substituted $C_1$-$C_{10}$ amido or unsubstituted $C_1$-$C_{10}$ amido.

In some forms of Formula I or Formula I(a), $R_1$ has the structure:

Formula II

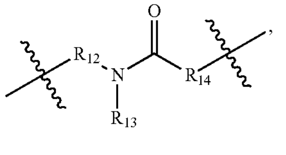

wherein $R_{12}$ is substituted $C_1$-$C_5$ alkylene or unsubstituted $C_1$-$C_5$ alkylene, $R_{12}$ is hydrogen, substituted $C_1$-$C_5$ alkyl, or unsubstituted $C_1$-$C_5$ alky, and $R_{14}$ is substituted $C_1$-$C_5$ alkylene or unsubstituted $C_1$-$C_5$ alkylene.

In some forms of Formula II, Rig is substituted $C_1$-$C_5$ alkylene (preferably —$CH(CH_3)$—), $R_{12}$ is unsubstituted $C_1$-$C_5$ alkyl (preferably —$CH_3$), and $R_{14}$ is unsubstituted $C_1$-$C_5$ alkylene (preferably —$(CH_2)_2$—).

In some forms of Formula I or Formula I(a), $R_2$, $R_3$, $R_4$, $R_5$, $R_6$, $R_7$, $R_8$, $R_9$, $R_{10}$, and $R_H$ are independently hydrogen, hydroxy, halogen (F, Br, Cl, I), substituted $C_1$-$C_5$ alkyl, unsubstituted $C_1$-$C_5$ alkyl, substituted aryl, unsubstituted aryl, substituted heteroaryl, unsubstituted heteroaryl, unsubstituted $C_1$-$C_5$ alkenyl, substituted $C_1$-$C_5$ alkenyl, unsubstituted $C_1$-$C_5$ alkynyl, substituted $C_1$-$C_5$ alkynyl, unsubstituted $C_1$-$C_5$ alkoxy, substituted $C_1$-$C_5$ alkoxy, unsubstituted aroxy, substituted aroxy, unsubstituted $C_1$-$C_5$ alkylthio, substituted $C_1$-$C_5$ alkylthio, unsubstituted arylthio, substituted arylthio, unsubstituted $C_1$-$C_5$ carbonyl, substituted $C_1$-$C_5$ carbonyl, unsubstituted $C_1$-$C_5$ carboxyl, substituted $C_1$-$C_5$ carboxyl, unsubstituted $C_1$-$C_5$ amino, substituted $C_1$-$C_5$ amino, unsubstituted $C_1$-$C_5$ sulfonyl, substituted $C_1$-$C_5$ sulfonyl, unsubstituted $C_1$-$C_5$ sulfamoyl, substituted $C_1$-$C_5$ sulfamoyl, unsubstituted $C_1$-$C_5$ phosphonyl, substituted $C_1$-$C_5$ phosphonyl, unsubstituted polyaryl, substituted polyaryl, unsubstituted $C_3$-$C_6$ cyclic, substituted $C_3$-$C_6$ cyclic, unsubstituted $C_3$-$C_6$ heterocyclic, or substituted $C_3$-$C_6$ heterocyclic, or $R_2$ and $R_3$ together with the carbon atoms to which they are bonded an epoxide.

In some forms of Formula I or Formula I(a), $R_2$ and $R_3$ together with the carbon atoms to which they are bonded are an epoxide.

In some forms of Formula I or Formula I(a), $R_4$, $R_5$, $R_6$, and $R_7$ are independently hydrogen, hydroxy, halogen (F, Br, Cl, I), substituted $C_1$-$C_5$ alkyl, unsubstituted $C_1$-$C_5$ alkyl, substituted aryl, unsubstituted aryl, substituted heteroaryl, or unsubstituted heteroaryl. In some forms of Formula I or Formula I(a), $R_4$, $R_5$, and $R_6$ are hydrogen, and $R_7$ is methyl.

In some forms of Formula I or Formula I(a), $R_8$ is hydrogen, hydroxy, halogen (F, Br, Cl, I), substituted $C_1$-$C_5$ carboxyl, unsubstituted $C_1$-$C_5$ carboxyl, substituted $C_1$-$C_5$ carbonyl, or unsubstituted $C_1$-$C_5$ carbonyl. In some forms of Formula I or Formula I(a), $R_8$ is hydrogen, hydroxy, substituted $C_1$-$C_5$ carboxyl, or unsubstituted $C_1$-$C_5$ carboxyl. In some forms of Formula I or Formula I(a), $R_8$ is hydrogen.

In some forms of Formula I or Formula I(a), $R_9$ is hydrogen, substituted $C_1$-$C_5$ alkyl, unsubstituted $C_1$-$C_5$ alkyl, substituted $C_1$-$C_5$ carbonyl, or unsubstituted $C_1$-$C_5$ carbonyl. In some forms of Formula I or Formula I(a), $R_9$ is unsubstituted $C_1$-$C_5$ alkyl. In some forms of Formula I or Formula I(a), $R_9$ is methyl.

In some forms of Formula I or Formula I(a), $R_{10}$ is a halogen (F, Cl, Br, I), substituted $C_1$-$C_5$ alkyl, unsubstituted $C_1$-$C_5$ alkyl, substituted $C_1$-$C_5$ carbonyl, or unsubstituted $C_1$-$C_5$ carbonyl. In some forms of Formula I or Formula I(a), $R_{10}$ is a halogen. In some forms of Formula I or Formula I(a), $R_{10}$ is Cl.

In some forms of Formula I or Formula I(a), $R_{11}$ is hydrogen, substituted $C_1$-$C_5$ alkyl, unsubstituted $C_1$-$C_5$ alkyl, substituted aryl, unsubstituted aryl, substituted heteroaryl, or unsubstituted heteroaryl. In some forms of Formula I or Formula I(a), $R_{11}$ is unsubstituted $C_1$-$C_5$ alkyl. In some forms of Formula I or Formula I(a), $R_{11}$ is methyl.

In some forms of Formula I or Formula I(a), the compounds have the structure:

Formula III

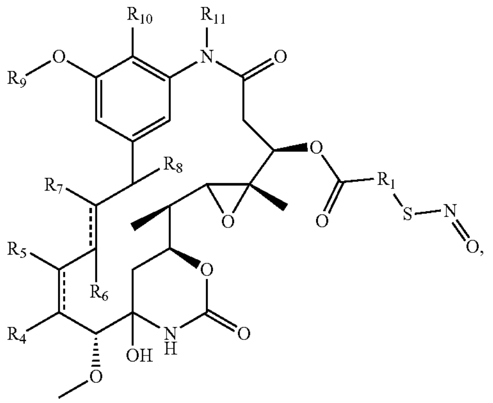

Formula IV

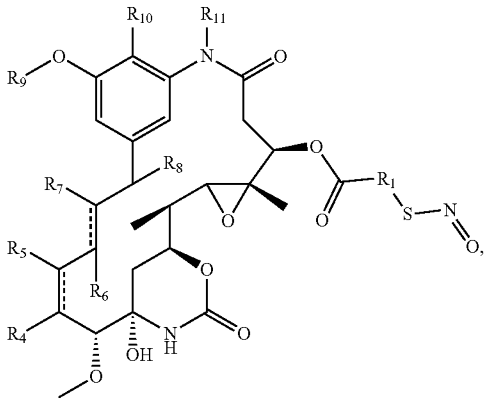

Formula V

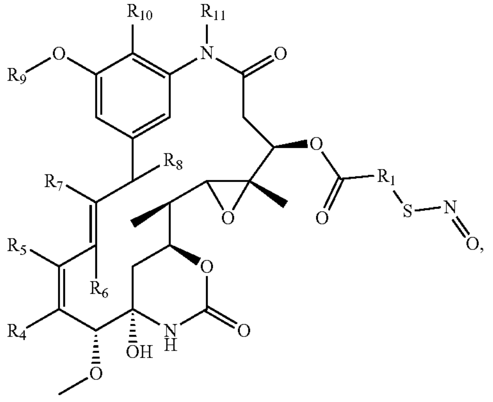

-continued

Formula VI

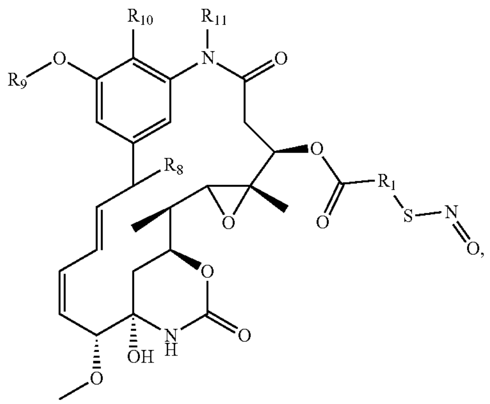

Formula VII

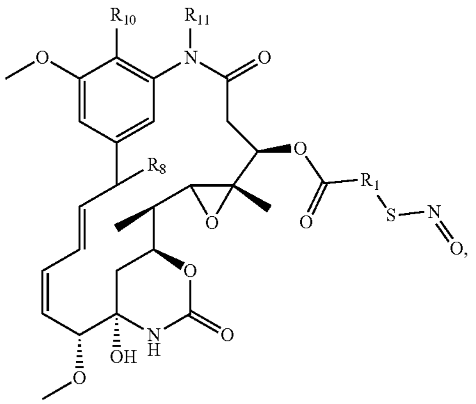

Formula VIII

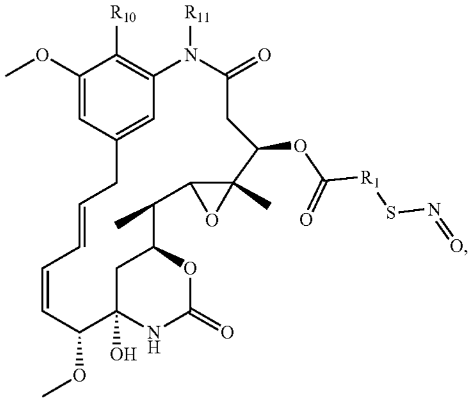

-continued

Formula IX

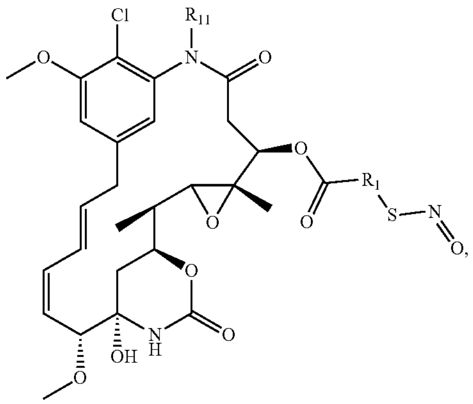

or

Formula X

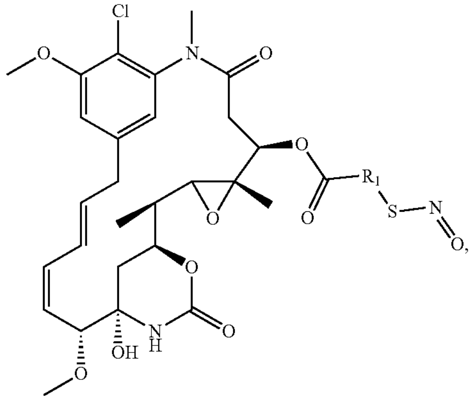

wherein when present, $R_1$, $R_4$, $R_5$, $R_6$, $R_7$, $R_8$, $R_9$, $R_{10}$, and $R_{11}$ in Formulae III to X are as described, for In some forms of Formula I or Formula I(a), in any of the preceding paragraphs.

In some forms, the compound has the structure:

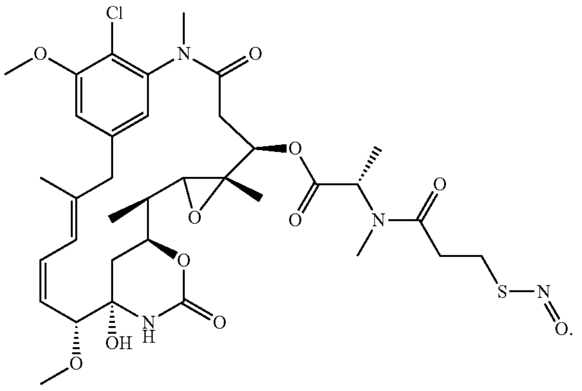 [SMILES: COc1cc2cc(c1Cl)N(C)C(=O)C[C@@H](OC(=O)[C@H](C)N(C)C(=O)CCSN=O)[C@]1(C)OC1[C@H](C)[C@@H]1C[C@@](O)(NC(=O)O1)[C@H](OC)/C=C\C=C(/C)C2]

In some forms, the parent compound is another chemotherapeutic agent or radiosensitizer. Examples of known radiosensitizers include nicotinamide, metronidazole and its analogs including, for example, misoniszole, etanidazole, and nimorazole; hypoxic cell cytotoxic agents such as mitomycin-C and tirapazamine; membrane active agents such as procaine, lidocaine, and chlorpromazine; radiosensitizing nucleosides such as 5-fluorouracil, fluorodeoxyuridine, bromodeoxyuridine, lododeoxyuridine, hydroxyurea, gemcitabine, and fludarabine; texaphryins such as motexafin gadolinium; suppressors of sulfhydral groups such as N-ethylmaleimide, diamide, and diethylmaleate; chemotherapeutic agents such as paclitaxel, docetaxel, and irinotecan, and cisplatin; pentoxifylline; vinorelbine; PARP inhibitors; histone deacetylase inhibitors; and proteasome inhibitors. See e.g., Raviraj, et al., *Indian Journal of Dental Research,* 25(1):83-90 (2014).

In some forms, a small molecule, in general, the radiosensitizers mentioned above, or maytansinoid can be chemically modified to introduce one or more thiol groups. Thiol groups can be introduced into chemical compounds using reagents that contain two or more functional groups, one of which is a thiol group. The other functional groups can be hydroxyl, carboxylic acids, amines, halides, aldehydes, ketones, etc. Depending on the reaction conductions, the thiol group can be protected via a disulfide bond that is ultimately reduced to expose the thiol group. Following introduction, one or more of the thiol group can be reacted with a nitric oxide donor, such as tert-butyl nitrite. S-nitrosylation can be achieved following protocols described in Chipinda and Simoyi, *J. Phys. Chem. B* 2006, 110, 5052-5061 and Pant, et al., ACS Appl. Mater. Interfaces 2017, 9, 15254-15264, the contents of which are herein incorporated by reference.

In some forms, the compounds can be encapsulated and/or delivered with additional radiosensitizing agents, such as those mentioned above, and/or anti-cancer agents. Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

B. Nanoparticles

The compounds can be in polymeric nanoparticles, liposomes, inorganic nanoparticles, or a combination thereof.

The experiments below illustrate that nanotechnology allows the revisiting of therapeutics such as maytansinoids that may be potent radiosensitizers but too toxic to be administered alone.

i. Polymeric Nanoparticles

In some forms, the nanoparticles can be a matrix of biocompatible polymers, preferably biodegradable polymers. The polymers can be amphiphilic, hydrophobic, or hydrophilic polymers that can be broken down hydrolytically or enzymatically in vitro or in vivo. Exemplary polymers are discussed below. Copolymers such as random, block, or graft copolymers, or blends of the polymers listed below can also be used.

The weight average molecular weight can vary for a given polymer but is generally between about 1000 Daltons and 1,000,000 Daltons, between about 1000 Daltons and about 500,000 Dalton, between about 1000 Daltons and about 250,000 Daltons, between about 1000 Daltons and about 100,000 Daltons, between about 5,000 Daltons and about 100,000 Daltons, between about 5,000 Daltons and about 75,000 Daltons, between about 5,000 Daltons and about 50,000 Daltons, or between about 5,000 Daltons and about 25,000 Daltons.

The extracellular microenvironment of tumor tissue is generally more mildly acidic than healthy tissue. In addition, the lumen of endosomes and lysosomes are also generally more acidic than the cytoplasm of a cell. Accordingly, to enhance the release of the cargo from nanoparticles in a tumor site prior to or post-nanoparticle uptake via the process of polymer degradation, diffusion, or both, the polymers can be acidic pH-responsive. In these forms, the polymers can contain ionizable groups (e g amine group(s)) that can become ionized and cause the nanoparticles to swell, or the polymers can contain a chemical moiety (such as disulfides, orthoesters, acetals, ketals, hydrazones, imines, cis-aconityls, esters, vinyl ethers, etc.) that can be cleaved more rapidly in an environment having acidic pH (such between 6.9 and 4.0) compared to an environment with a higher pH (such as 7.2, 8, 9, or higher).

a. Amphiphilic Polymers

The NPs can contain one or more amphiphilic polymers, preferably biodegradable amphiphilic polymers. The amphiphilic polymers contain a hydrophobic polymer portion and a hydrophilic polymer portion. The hydrophobic polymer portion and hydrophilic polymer portion can include any of the hydrophobic polymers and hydrophilic polymers, respectively, described in the corresponding titular sections below. In a non-limiting example, the hydrophobic polymer portion is a polymer formed from a polyester such as polyhydroxy acids (such as poly(lactic acid), poly(glycolic acid), and poly(lactic acid-co-glycolic acid)s), polycaprolactones, polyhydroxyalkanoates (such as poly-3-hydroxybutyrate, poly4-hydroxybutyrate, polyhydroxyvalerates), poly(lactide-co-caprolactones); poly(anhydride)s; poly(orthoester)s; hydrophobic polysaccharides (such as acetalated dextran, acetylated dextran, acetylated cellulose, proprionylated dextran, proprionylated cellulose); and hydrophobic polyethers (such as polypropylene glycol); as well as copolymers thereof. The hydrophilic polymer portion can contain a polymer such as a polyalkylene oxide such as polypropylene glycol or polyethylene glycol (PEG); polysaccharides such as cellulose and starch; hydrophilic polypeptides such as poly-L-glutamic acid, gamma-polyglutamic acid, poly-L-aspartic acid, poly-L-serine, or poly-L-lysine; poly (oxyethylated polyol); poly(olefinic alcohol) such as poly (vinyl alcohol); poly(vinylpyrrolidone); polyacrylamides or polymethaacrylamides including poly(N-hydroxyalkyl methacrylamides) such as poly(N-hydroxyethyl methacrylamide); poly(N-hydroxyalkyl methacrylates) such as poly (N-hydroxyethyl methacrylate); hydrophilic poly(hydroxy acids); and copolymers thereof. Examples of amphiphilic polymers that can be generated from this group include polyester-PEG copolymers such as poly(lactic acid-co-glycolic acid)-PEG (PLGA-PEG), poly(lactic acid)-PEG (PLA-PEG), poly(glycolic acid)-PEG (PGA-PEG), and polycaprolactone-PEG (PCL-PEG); hydrophobic polyethers-PEG, such as polypropylene glycol-PEG (PPG-PEG), PEG-PPG-PEG, PPG-PEG-PPG; and acetylated dextran-PEG. In some forms, the amphiphilic polymer can be PLGA-PEG.

b. Hydrophobic Polymers

The NPs can formed of one or more hydrophobic polymers. In some forms, the hydrophobic polymers are biodegradable. Examples of suitable hydrophobic polymers include polyesters such as polyhydroxy acids (such as poly(lactic acid-co-glycolic acid)s, poly(lactic acid), poly (glycolic acid)), polycaprolactones, polyhydroxyalkanoates (such as poly-3-hydroxybutyrate, poly4-hydroxybutyrate, polyhydroxyvalerates), poly(lactide-co-caprolactones); poly (anhydride)s; poly(orthoester)s; hydrophobic polysaccharides (such as acetalated dextran, acetylated dextran, acetylated cellulose, proprionylated dextran, proprionylated cellulose); as well as copolymers thereof.

In some forms, the hydrophobic polymers include polyesters such as polyhydroxy acids (such as poly(lactic acid-co-glycolic acid)s, poly(lactic acid), poly(glycolic acid)), polycaprolactones, polyhydroxyalkanoates (such as poly-3-hydroxybutyrate, poly4-hydroxybutyrate, polyhydroxyvalerates), poly(lactide-co-caprolactones); poly(anhydride) s; poly(orthoester)s; poly(beta-amino ester)s; and copolymers thereof.

c. Hydrophilic Polymers

The NPs can contain one or more hydrophilic polymers. Preferably, the hydrophilic polymers are biodegradable. Hydrophilic polymers include polyalkylene glycol such as polyethylene glycol (PEG); polysaccharides such as cellulose and starch and derivatives thereof; hydrophilic polypeptides such as poly-L-glutamic acid, gamma-polyglutamic acid, poly-L-aspartic acid, poly-L-serine, or poly-L-lysine; poly(oxyethylated polyol); poly(olefinic alcohol) such as poly(vinyl alcohol); poly(vinylpyrrolidone); poly(N-hydroxyalkyl methacrylamide) such as poly(N-hydroxyethyl methacrylamide); poly(N-hydroxyalkyl methacrylate) such as poly(N-hydroxyethyl methacrylate); hydrophilic poly(hydroxy acids); and copolymers thereof. In some forms, the hydrophilic polymer is a polyalkylene glycol such as PEG or a poloxamer.

ii. Liposomes and Micelles

In some forms, the compounds can be encapsulated in liposomal vesicles, lipid micelles, or solid lipid nanoparticles, or a combination thereof. The nanoparticles can contain one or more lipids or amphiphilic compounds. The nanoparticles are preferably made from one or more biocompatible lipids. The nanoparticles can be made from one or a mixture of different lipids that can be neutral, anionic, or cationic at physiologic pH (such as pH 7.4). As a non-limiting example, a charged lipid may be combined with a lipid that is non-ionic or uncharged at physiological pH.

In some forms, the nanoparticle can be a lipid micelle. Lipid micelles for drug delivery are known in the art. Lipid micelles can be formed, for instance, as a water-in-oil emulsion with a lipid surfactant. An emulsion is a blend of two immiscible phases wherein a surfactant is added to stabilize the dispersed droplets. The lipid micelle can be a microemulsion. A microemulsion is a thermodynamically stable system composed of at least water, oil, and a lipid surfactant producing a transparent and thermodynamically stable system whose droplet size is less than 1 micron, from about 10 nm to about 500 nm, or from about 10 nm to about 250 nm. Lipid micelles are generally useful for encapsulating hydrophobic active agents, including hydrophobic therapeutic agents, hydrophobic prophylactic agents, or hydrophobic diagnostic agents.

In some forms, the nanoparticle can be a liposome, such as a liposomal vesicle. Liposomal vesicles typically contain an aqueous medium surrounded by lipids arranged in spherical bilayers. Liposomal vesicles can be classified as small unilamellar vesicles, large unilamellar vesicles, or multi-lamellar vesicles. Multi-lamellar liposomes contain multiple concentric lipid bilayers. Liposomes can be used to encapsulate therapeutic, diagnostic, and or prophylactic agents, by trapping hydrophilic agents in the aqueous interior or between bilayers, or by trapping hydrophobic agents within the bilayer.

The lipid micelles and liposomes typically have an aqueous center. The aqueous center can contain water or a mixture of water and alcohol. Suitable alcohols include, but are not limited to, methanol, ethanol, propanol, (such as isopropanol), butanol (such as n-butanol, isobutanol, sec-butanol, tert-butanol, pentanol (such as amyl alcohol, isobutyl carbinol), hexanol (such as 1-hexanol, 2-hexanol, 3-hexanol), heptanol (such as 1-heptanol, 2-heptanol, 3-heptanol and 4-heptanol) or octanol (such as 1-octanol) or a combination thereof.

In some forms, the nanoparticle can be a solid lipid nanoparticle. Solid lipid nanoparticles present an alternative to the colloidal micelles and liposomal vesicles. Solid lipid nanoparticles are typically submicron in size, i.e. from about 10 nm to about 1 micron, from 10 nm to about 500 nm, or from 10 nm to about 250 nm. Solid lipid nanoparticles can be formed of lipids that are solids at room temperature. They are derived from oil-in-water emulsions, by replacing the liquid oil by a solid lipid.

Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including 1,2-diacyl-glycero-3-phosphocholines; phosphatidylserine (PS), phosphatidylglycerol, phosphatidylinositol (PI); glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-.alpha.-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids.

Suitable cationic lipids include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2,3-dioloyloxy) propyl]-N,N-dimethyl amine (DODAP), 1,2-diacyloxy-3-dimethylammonium propanes, N-[1-(2,3-dioleyloxy) propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA), .beta.-alanyl cholesterol, cetyl trimethyl ammonium bromide (CTAB), diC.sub.14-amidine, N-ferf-butyl-N'-tetradecyl-3-tetradecylamino-propionamidine, N-(alpha-trimethylammonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N,N,N',N'-tetramethyl-, N'-bis(2-hydroxylethyl)-2,3-dioleoyloxy-1,4-butanediammonium iodide. In one embodiment, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)-imidazolinium chloride (DOTIM), and 1-[2-(hexadecanoyloxy)ethyl]-2-pentadecyl-3-(2-hydroxyethyl)imidazolinium chloride (DPTIM). In one embodiment, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

Suitable solid lipids include, but are not limited to, higher saturated alcohols, higher fatty acids, sphingolipids, synthetic esters, and mono-, di-, and triglycerides of higher saturated fatty acids. Solid lipids can include aliphatic alcohols having 10-40, preferably 12-30 carbon atoms, such as cetostearyl alcohol. Solid lipids can include higher fatty acids of 10-40, preferably 12-30 carbon atoms, such as stearic acid, palmitic acid, decanoic acid, and behenic acid. Solid lipids can include glycerides, including monoglycerides, diglycerides, and triglycerides, of higher saturated fatty acids having 10-40, preferably 12-30 carbon atoms, such as glyceryl monostearate, glycerol behenate, glycerol palmitostearate, glycerol trilaurate, tricaprin, trilaurin, trimyristin, tripalmitin, tristearin, and hydrogenated castor oil. Suitable solid lipids can include cetyl palmitate, beeswax, or cyclodextrin.

Amphiphilic compounds include, but are not limited to, phospholipids, such as 1,2 distearoyl-sn-glycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01-60 (weight lipid/w polymer), most preferably between 0.1-30 (weight lipid/w polymer). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and .beta.-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcho-line (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophos-phoethanolamine. Synthetic phospholipids with asymmetric acyl chains (e.g., with one acyl chain of 6 carbons and another acyl chain of 12 carbons) may also be used.

In some embodiments, the liposomes can be coated with a water-soluble, biocompatible polymer. Suitable polymers include, but are not limited to polyalkylene oxides such as polyethylene glycol (PEG), polyethylene glycol-polypropylene block copolymer such as a PLURONIC®, poly(N-isopropylacrylamide) (PNIPAM), polyacrylamide (PAM), poly(carboxybetaine)s (pCB), poly(sulfobetaine)s (pSB), poly(phosphobetaine)s, and polyethyleneimine (PEI). In some forms, the polymer can be polyethylene glycol forming coated liposomes collectively known as PEGylated liposomes.

iii. Inorganic Nanoparticles

In some forms, the particles can be of an inorganic composition including, but not limited to, minerals, including silica, silicates; sulfides (such as bismuth sulfide ($Bi_2S_3$), gold bismuth sulfide (Au-si$Bi_2S_3$), oxides, halides, carbonates, sulfates, phosphates; iron(II) oxide, iron(III) oxide. In some forms, the particles can also be made of one or more metals, such as gold nanoparticles, silver nanoparticles, copper, platinum, palladium, ruthenium, or a combination thereof.

iv. Size

The size of the particles can vary. In some forms the particle size is between about 5 nm and less than 1,000 nm. In some forms, the particle size is between about 10 nm and about 750 nm. In some forms, the particle size is between about 10 nm and about 500 nm. In some forms, the particle size is between about 10 nm and about 250 nm. In some forms, the particle size is between about 50 nm and about 250 nm. In some forms, the particle size is between about 50 nm and about 150 nm. In some forms, the particle size is between about 50 nm and about 100 nm. In some forms, the particle size is between about 10 nm, about 20 nm, about 30 nm, about 40 nm, about 50 nm, about 60 nm, about 70 nm, about 78 nm, about 80 nm, about 90 nm, about 100 nm, about 110 nm, about 120 nm, about 130 nm, about 140 nm, or about 150 nm.

v. Targeting Agents

The compounds containing one or more S-nitrosothiol moieties and/or nanoparticles for delivery of the compounds can also include a targeting agent. A targeting agent can be a peptide, nucleic acid, glycoprotein, carbohydrate, lipid, or small molecule that binds to one or more targets associated with an organ, tissue, cell, subcellular locale, or extracellular matrix.

In some forms, one or more targeting agents can be conjugated to the compounds or nanoparticles, preferably covalently. The targeting agents can be covalently associated with the compounds or nanoparticles, directly or indirectly via a linker. Although discussed herein primarily as attaching a targeting agent to nanoparticles, in some embodiments a compound containing one or more S-nitrosothiol moieties is coupled to a targeting agent, e.g., a peptide or protein, with an appropriate linker and used without nanoparticles. Preferably the targeting agent does not interfere with compound's activity and the compound does not interfere with receptor binding. It is believed that if the spacer is long enough, the drug's interference with receptor binding would be low.

In some embodiments, coupling of the target agent to the compounds or nanoparticles is achieved by linking a sulfhydryl (—SH) (e.g., on a cysteine) and an amine using, e.g., Sulfosuccinimidyl-4-(N-maleimidomethyl) cyclohexane-1-carboxylate (Sulfo-SMCC) crosslinker. For example, the compounds or particles can have a free amine (e.g., PLGA-b-PEG-amine) and the targeting agent can have a cysteine with an —SH available for crosslinking. In other embodiments, a carboxyl-to-amine crosslinker such as EDC/NHS can be used. In a particular example, the particles have a free carboxyl (e.g., PLGA-b-PEG-COOH) and the targeting agent has a free amine. Click chemistry can also be used for the coupling. A common example is azide-alkyne coupling through copper(I) catalysis or copper free strain-promoted cycloaddition. Strain-promoted alkyne-nitrone cycloaddition is also feasible. Adize and alkyne can be separately coupled to compounds or nanoparticles and targeting ligands, and click chemistry will link the two components together.

The particles can be composed of a mixture of polymers, e.g., with and without the moiety used to couple the targeting agent. For example, by illustration with reference to the particular foregoing embodiments, the particles may be formed of a mixture including PLGA-b-PEG and PLGA-b-PEG-amine, or a mixture of PLGA-b-PEG and PLGA-b-PEG-COOH. Any suitable ratio of polymers can be used, and can be used to tune the relative number of targeting agents presented on the surface of the nanoparticle (i.e., ligand surface density). For example, the molar ratio of polymer with the coupling moiety to polymer without coupling moiety can be X:Y wherein X and Y are independently any integer from 1-100 inclusive. In an exemplary embodiment, non-limiting embodiment, the molar ratio of polymer with the coupling moiety to polymer without coupling moiety is 1:10. The peptide-to-particle ratio can then be calculated (Derman, et al., *J Biomed Sci,* 22, 89 (2015)).

Preferably, the targeting agent binds to a molecule (targeted moiety) that is specific to tumor cells, or may be expressed at a higher level on tumor cells as compared to non-tumor cells.

Examples of targeting agents include peptides such as iRGD, NGR, iNGR, RGR, LyP1; small molecules such as folate; aptamers, antibodies, antigen binding fragment or fusion proteins of an antibody.

Exemplary antibodies and fragments that can be used include monoclonal and polyclonal antibodies, single chain antibodies, single chain variable fragments (scFv), di-scFv, tri-scFv, diabody, triabody, tetrabody, disulfide-linked Fvs (sdFv), Fab', $F(ab')_2$, Fv, and single domain antibody fragments (sdAb). The antibodies can bind to targets on cancer cells or in a tumor's microenvironment. Exemplary cancer antigen targets are discussed below.

Examples of targeting peptides are described in U.S. Pat. Nos. 6,177,542, 7,544,767, and 6,576,239; U.S. Patent Application Publication No. 20090257951; and Hoffman, et al., Cancer Cell, vol. 4 (2003). Useful NGR peptides include peptide such as $X_2CNGRCX_2$ (SEQ ID NO:1), $CX_2(C/X)NGR(C/X)X_2C$ (SEQ ID NO:2), and $CNGRCX_6$ (SEQ ID NO:3) (where "X" is any amino acid), which can be linear or circular.

Useful peptides for tumor targeting include, for example, iRGD, LyP-1, iNGR, and RGR peptides. iRGD has a unique target within tumors; it preferentially accumulates in the hypoxic/low nutrient areas of tumors (Laakkonen, et al., 2002; 2004; Karmali, et al., 2009). CRGRRST (SEQ ID NO:4) (RGR; Joyce, et al., 2003) is a peptide that has been successfully used in targeting a cytokine antibody combination into tumors (Hamzah, et al., 2008). This peptide is linear, which simplifies the synthesis. NGR peptides home to angiogenic vasculature, including angiogenic vasculature associated with tumors, and $\alpha_v$ integrin and $\alpha_5\beta_1$ integrin (U.S. Pat. Nos. 6,576,239 and 6,177,542 and U.S. Patent Application Publication No. 20090257951).

In some forms, the targeted moiety is an antigen that is expressed by tumor cells. Antigenic markers such as serologically defined markers known as tumor associated antigens, which are either uniquely expressed by cancer cells or are present at markedly higher levels (e.g., elevated in a statistically significant manner) in subjects having a malignant condition relative to appropriate controls, are known.

Tumor-associated antigens may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melonoma associated antigens, etc.) (see, e.g., U.S. Pat. No. 6,699,475; Jager, et al., *Int. J. Cancer,* 106:817-20 (2003); Kennedy, et al., *Int. Rev. Immunol.,* 22:141-72 (2003); Scanlan, et al., *Cancer Immun.,* 4:1 (2004)).

Genes that encode cellular tumor associated antigens include cellular oncogenes and proto-oncogenes that are aberrantly expressed. In general, cellular oncogenes encode products that are directly relevant to the transformation of the cell, so these antigens are particularly preferred targets for immunotherapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene. Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. J. Med.*, 309:883 (1983); Lloyd, et al., *Int. J. Canc.*, 71:842 (1997). CA levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.*, 36:755 (1997); Sarandakou, et al., *Eur. J. Gynaecol. Oncol.*, 19:73 (1998); Meier, et al., *Anticancer Res.*, 17(4B):2945 (1997); Kudoh, et al., *Gynecol. Obstet. Invest.*, 47:52 (1999)). Elevated serum CA125 may also accompany neuroblastoma (e.g., Hirokawa, et al., *Surg. Today*, 28:349 (1998), while elevated CEA and SCC, among others, may accompany colorectal cancer (Gebauer, et al., *Anticancer Res.*, 17(4B):2939 (1997)).

The tumor associated antigen mesothelin, defined by reactivity with monoclonal antibody K-1, is present on a majority of squamous cell carcinomas including epithelial ovarian, cervical, and esophageal tumors, and on mesotheliomas (Chang, et al., *Cancer Res.*, 52:181 (1992); Chang, et al., *Int. J. Cancer*, 50:373 (1992); Chang, et al., *Int. J. Cancer*, 51:548 (1992); Chang, et al., *Proc. Natl. Acad. Sci. USA*, 93:136 (1996); Chowdhury, et al., *Proc. Natl. Acad. Sci. USA*, 95:669 (1998)). Using MAb K-1, mesothelin is detectable only as a cell-associated tumor marker and has not been found in soluble form in serum from ovarian cancer patients, or in medium conditioned by OVCAR-3 cells (Chang, et al., *Int. J. Cancer*, 50:373 (1992)). Structurally related human mesothelin polypeptides, however, also include tumor-associated antigen polypeptides such as the distinct mesothelin related antigen (MRA) polypeptide, which is detectable as a naturally occurring soluble antigen in biological fluids from patients having malignancies (see WO 00/50900).

A tumor antigen may include a cell surface molecule. Tumor antigens of known structure and having a known or described function, include the following cell surface receptors: HER1 (GenBank Accession NO: U48722), HER2 (Yoshino, et al., *J. Immunol.*, 152:2393 (1994); Disis, et al., Canc. Res., 54:16 (1994); GenBank Acc. Nos. X03363 and M17730), HER3 (GenBank Acc. Nos. U29339 and M34309), HER4 (Plowman, et al., *Nature*, 366:473 (1993); GenBank Acc. Nos. L07868 and T64105), epidermal growth factor receptor (EGFR) (GenBank Acc. Nos. U48722, and KO3193), vascular endothelial cell growth factor (GenBank NO: M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043, European Patent No. GB 2241703), insulin-like growth factor-II (GenBank Acc. Nos. X03562, X00910, M17863 and M17862), transferrin receptor (Trowbridge and Omary, *Proc. Nat. Acad. USA*, 78:3039 (1981); GenBank Acc. Nos. X01060 and M11507), estrogen receptor (GenBank Acc. Nos. M38651, X03635, X99101, U47678 and M12674), progesterone receptor (GenBank Acc. Nos. X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., *Proc. Nat. Acad. Sci. USA*, 86:7159 (1989); GenBank Acc. Nos. M65132 and M64928) NY-ESO-1 (GenBank Acc. Nos. AJ003149 and U87459), NA 17-A (PCT Publication NO: WO 96/40039), Melan-A/MART-1 (Kawakami, et al., *Proc. Nat. Acad. Sci. USA*, 91:3515 (1994); GenBank Acc. Nos. U06654 and U06452), tyrosinase (Topalian, et al., *Proc. Nat. Acad. Sci. USA*, 91:9461 (1994); GenBank Acc. NO: M26729; Weber, et al., *J. Clin. Invest*, 102:1258 (1998)), Gp-100 (Kawakami, et al., *Proc. Nat. Acad. Sci. USA*, 91:3515 (1994); GenBank Acc. NO: 573003, Adema, et al., *J. Biol. Chem.*, 269:20126 (1994)), MAGE (van den Bruggen, et al., *Science*, 254:1643 (1991)); GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. NO: U19180; U.S. Pat. Nos. 5,683,886 and 5,571,711), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), carcinoembryonic antigen (CEA, Gold and Freedman, *J. Exp. Med.*, 121:439 (1985); GenBank Acc. Nos. M59710, M59255 and M29540), and PyLT (GenBank Acc. Nos. J02289 and J02038); p 97 (melanotransferrin) (Brown, et al., *J. Immunol.*, 127:539-46 (1981); Rose, et al., *Proc. Natl. Acad. Sci. USA*, 83:1261-61 (1986)).

Additional tumor associated antigens include prostate surface antigen (PSA) (U.S. Pat. Nos. 6,677,157; 6,673,545); β-human chorionic gonadotropin β-HCG) (McManus, et al., *Cancer Res.*, 36:3476-81 (1976); Yoshimura, et al., *Cancer*, 73:2745-52 (1994); Yamaguchi, et al., *Br. J. Cancer*, 60:382-84 (1989): Alfthan, et al., *Cancer Res.*, 52:4628-33 (1992)); glycosyltransferase β-1,4-N-acetylgalactosaminyltransferases (GalNAc) (Hoon, et al., *Int. J. Cancer*, 43:857-62 (1989); Ando, et al., *Int. J. Cancer*, 40:12-17 (1987); Tsuchida, et al., *J. Natl. Cancer*, 78:45-54 (1987); Tsuchida, et al., *J. Natl. Cancer*, 78:55-60 (1987)); NUC18 (Lehmann, et al., *Proc. Natl. Acad. Sci. USA*, 86:9891-95 (1989); Lehmann, et al., *Cancer Res.*, 47:841-45 (1987)); melanoma antigen gp75 (Vijayasardahi, et al., *J. Exp. Med.*, 171:1375-80 (1990); GenBank Accession NO: X51455); human cytokeratin 8; high molecular weight melanoma antigen (Natali, et al., *Cancer*, 59:55-63 (1987); keratin 19 (Datta, et al., *J. Clin. Oncol.*, 12:475-82 (1994)).

Tumor antigens of interest include antigens regarded in the art as "cancer/testis" (CT) antigens that are immunogenic in subjects having a malignant condition (Scanlan, et al., *Cancer Immun.*, 4:1 (2004)). CT antigens include at least 19 different families of antigens that contain one or more members and that are capable of inducing an immune response, including, but not limited to, MAGEA (CT1); BAGE (CT2); MAGEB (CT3); GAGE (CT4); SSX (CT5); NY-ESO-1 (CT6); MAGEC (CT7); SYCP1 (C8); SPANXB1 (CT11.2); NA88 (CT18); CTAGE (CT21); SPA17 (CT22); OY-TES-1 (CT23); CAGE (CT26); HOM-TES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but are not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3, 4, 5, 6, 7, GnTV, Herv-K-mel, Lage-1, Mage-A1, 2, 3, 4, 6, 10, 12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG- 72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Other tumor-associated and tumor-specific antigens are known to those of skill in the art and are suitable for targeting by the disclosed fusion proteins.

In some forms, antigens associated with tumor neovasculature can also be targeted. Tumor-associated neovasculature provides a readily accessible route through which therapeutics can access the tumor. In one embodiment the viral proteins contain a domain that specifically binds to an antigen that is expressed by neovasculature associated with a tumor.

The antigen may be specific to tumor neovasculature or may be expressed at a higher level in tumor neovasculature when compared to normal vasculature. Exemplary antigens that are over-expressed by tumor-associated neovasculature as compared to normal vasculature include, but are not limited to, VEGF/KDR, Tie2, vascular cell adhesion molecule (VCAM), endoglin and $\alpha_5\beta_3$ integrin/vitronectin. Other antigens that are over-expressed by tumor-associated neovasculature as compared to normal vasculature are known to those of skill in the art and are suitable for targeting by the disclosed fusion proteins.

Neurotensin receptor 1 (NTSR1) is upregulated in the majority of lung tumors (59.7%), but expressed at low or undetectable levels in normal pulmonary tissues (Alifano, et al., *Clinical Cancer Research,* 16, 4401-4410 (2010)). NTSR1 upregulation is associated with poor 5-year overall survival, high metastasis rate, and increased neuroendocrine differentiation (Alifano, et al., *Clinical Cancer Research,* 16, 4401-4410 (2010), Dupouy, *Biochimie,* 93, 1369-78 (2011)). Thus, in some embodiments, the disclosed compositions, e.g, nanoparticles, include a ligand for NTSR1 coupled thereto.

NTSR1 is also upregulated in head and neck, breast, and colon cancer. Thus, in some embodiments, the NTSR1-targeting compositions are used for treatment of a cancer with upregulated NTSR1. In some embodiments, the subject has a lung cancer such as NSCLC, a head and neck cancer, a breast cancer, and/or a colon cancer.

In some embodiments, the NTSR1 is the wildtype NTSR1 ligand, neurotensin (NTS), or a variant, analog, or functional fragment thereof.

A wildtype sequence for human NTS is QLYENKPRRPYIL (SEQ ID NO:5), UniProtKB—P30990 (NEUT_HUMAN)—amino acids 151-163, which is specifically incorporated by reference herein in its entirety. In some embodiments, the NTSR1 ligand includes at least 50, 55, 60, 65, 70, 75, 80, 85, 90, or 95% sequence identity to SEQ ID NO:5. Neurotensin shares significant sequence similarity in its 6 C-terminal amino acids with several other neuropeptides, including neuromedin N (which is derived from the same precursor) (see, e.g., UniProtKB—P30990 (NEUT_HUMAN)). This C-terminal region is responsible for the full biological activity, the N-terminal portion having a modulatory role.

The neurotensin/neuromedin N precursor can also be processed to produce large 125-138 amino acid peptides with the neurotensin or neuromedin N sequence at their C terminus. These large peptides appear to be less potent than their smaller counterparts, but are also less sensitive to degradation and may represent endogenous, long-lasting activators in a number of pathophysiological situations.

NTS has a short half-life in vivo due to peptidase degradation (Reinecke, et al., *Prog Histochem Cytochem,* 16, 1-172 (1985), Wu, et al., *J Nucl Med,* 55, 1178-1184 (2014)). Thus, in some embodiments, the NTSR1 ligand is an NTS analog. An exemplary NTS analog is $NTS_{mut}$. $NTS_{mut}$ includes amino acids 7-13 of SEQ ID NO:5, (e.g., PRRPYIL (SEQ ID NO:6) where unnatural amino acids are introduced to stabilize the bonds between Arg8-Arg9, Pro10-Tyr11, and Tyr11-Ile12.

A structure of an $NTS_{mut}$ with a terminal cysteine to facilitate coupling of the peptide to nanoparticles or compounds is provided below:

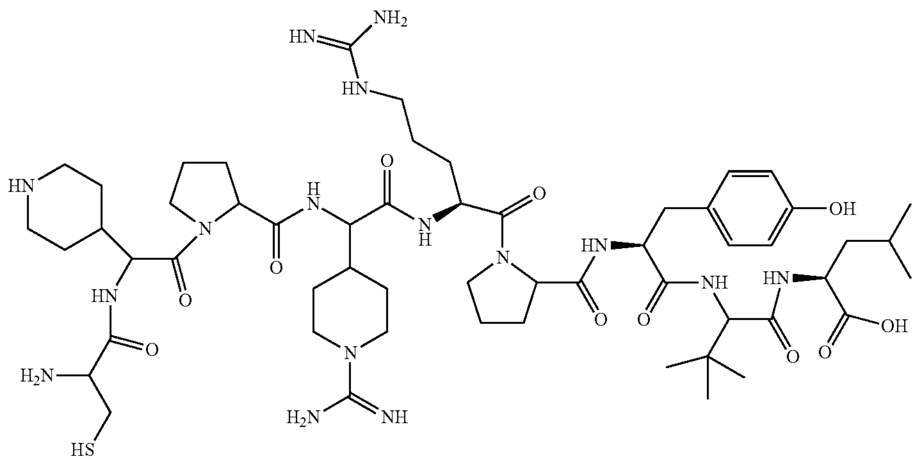

Cys-NTSmut

See also, e.g., Wu, et al., *J Nucl Med,* 55(7):1178-84 (2014) doi: 10.2967/jnumed.114.137489, which is specifically incorporated by reference herein in its entirety.

Figure 11:
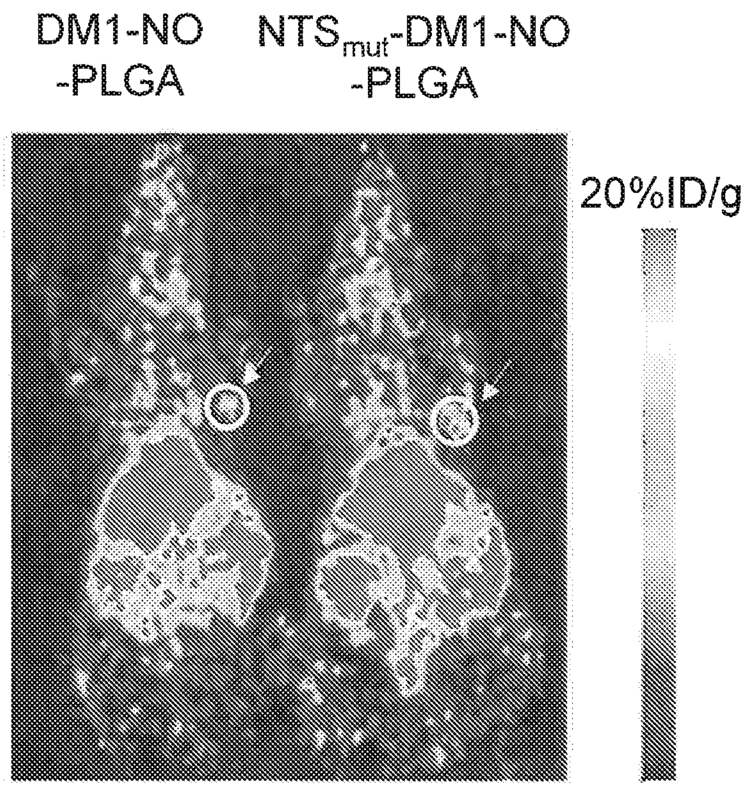
FIG. 11 are PET images obtained following 64Cu-labeled DM1-NO-PLGA and $NTS_{mut}$-DM1-NO PLGA NPs testing in H1299 tumor bearing mice. The images illustrate differences in DM1-NO-PLGA NPs believed to accumulate in tumors through the EPR effect vs. $NTS_{mut}$-DM1-NO PLGA NPs believed to accumulate in tumors through both EPR and NTSR1 targeting.

Compared to wildtype NTS, $NTS_{mut}$ affords comparable, nanomolar avidity to NTSR1, but much greater biological stability. Experimental results presented below illustrates that coupling $NTS_{mut}$ to the nanoparticles improves tumor accumulation (FIG. 11). Increased surface ligand density may enhance binding affinity to NTSR1, but may also increase surface hydrophobicity that may negatively affects pharmaco-kinetics.

In another embodiment, the ligand is $NTS_{20.8}$, e.g., as illustrated below with a cysteine to facilitate coupling of the peptide to nanoparticles or compounds, or one or its derivatives.

Other peptidomimetic and non-peptidic receptor agonists and antagonists are known in the art can be used as targeting ligands. See, e.g., Kleczkowska and Lipkowski, *European Journal of Pharmacology,* 716(1-3): 54-60 (2013), which is specifically incorporated by reference herein in its entirety.

III. Methods of Making and Reagents

A. Agents to be Delivered

Method of making agents to be delivered are provided. Preferred agents to be delivered can be prodrug compounds of, for example of radiosensitizers including inhibitors of microtubule polymerization, which contain one or more S-nitrosothiol moieties. In some forms, the prodrug compounds are maytansinoid analogs that contain one or more

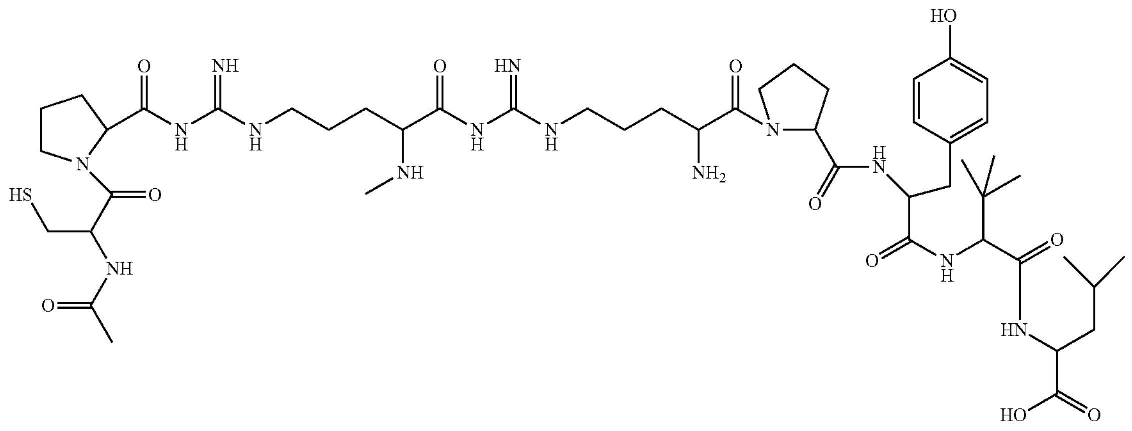

$Cys\text{-}NTS_{20.8}$

See also, e.g., Yin, et al., *Amino Acids,* 49(8):1325-1335. doi: 10.1007/s00726-017-2430-5, which is specifically incorporated by reference herein in its entirety.

In another embodiment, the ligand is SR142948A or one or its derivatives, or an NTSR1 antagonist analog thereof (Moody, et al., *Front Endocrinol,* 9 (2018), Kling, *ACS Chem Biol,* 11, 869-75 (2016), Schaeffer, *J Cardiovasc Pharmacol,* 31, 545-50 (1998).

In some embodiments, the ligand has the following structure:

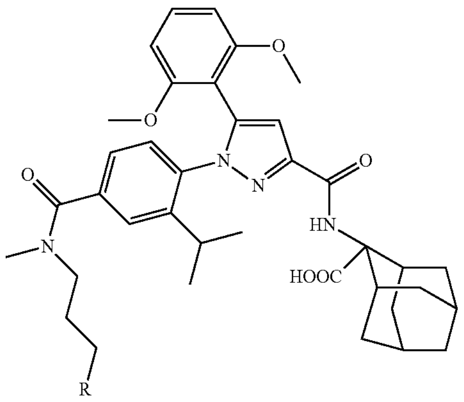

R = $NH_2$ and $N_3$

S-nitrosothiol moieties. These maytansinoids can be generated via chemical synthesis; isolation from higher plants, mosses, and microorganisms, followed by chemical modifications to include one or more S-nitrosothiol moieties. Cassady, et al., *Chem. Pharm. Bull.,* 52(1), 1-26 (2004), provides various strategies for the generation of maytansinoids, the contents of which are herein incorporated by reference. Approaches to chemically modify small molecules, in general, or maytansinoids to include one or more S-nitrosothiol moieties are discussed above.

B. Nanoparticles

Methods of making particles are also provided.

i. Polymeric Nanoparticles

Nanoprecipitation

In some forms, the nanoparticles can be prepared via the nanoprecipitation approach. In this method, water-soluble or water-miscible organic solvents are used to dissolve the polymer and form emulsion upon mixing with the aqueous phase preferably under moderate stirring. The quick diffusion of the organic solvent into water leads to the formation of nanoparticles immediately after the mixing. After formation of nanoparticles, the solvents can be removed under low/reduced pressure. Nanoprecipitation can be used to encapsulate hydrophobic or hydrophilic compounds, although the method is typically used to encapsulate hydrophobic compounds.

ii. Other Methods of Forming Nanoparticles

The nanoparticles described herein can be formed using a variety of techniques known in the art. The technique to be used can depend on a variety of factors including the polymer used to form the nanoparticles, the desired size range of the resulting nanoparticles, and suitability for the therapeutic, diagnostic, and/or prophylactic agent to be incorporated. Suitable techniques include, but are not limited to:

a. Solvent Evaporation

In this method the polymer is dissolved in a volatile organic solvent. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer Nanoparticles with different sizes and morphologies can be obtained by this method.

b. Solvent Removal

In this method, the drug is dispersed or dissolved in a solution of the selected polymer in a volatile organic solvent. This mixture is suspended by stirring in an organic oil (such as silicon oil) to form an emulsion. Unlike solvent evaporation, this method can be used to make nanoparticles from polymers with high melting points and different molecular weights. The external morphology of spheres produced with this technique is highly dependent on the type of polymer used.

c. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried.

d. Phase Inversion

Nanospheres can be formed from polymers using a phase inversion method wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. The method can be used to produce nanoparticles in a wide range of sizes, including, for example, about 100 nanometers to about 10 microns. Substances which can be incorporated include, for example, imaging agents such as fluorescent dyes, or biologically active molecules such as proteins or nucleic acids. In the process, the polymer is dissolved in an organic solvent and then contacted with a non-solvent, which causes phase inversion of the dissolved polymer to form small spherical particles, with a narrow size distribution optionally incorporating an antigen or other substance.

e. Microfluidics

Methods of making nanoparticles using microfluidics are known in the art. Suitable methods include those described in U.S. Patent Application Publication No. 2010/0022680 A1 by Karnik, et al. In general, the microfluidic device comprises at least two channels that converge into a mixing apparatus. The channels are typically formed by lithography, etching, embossing, or molding of a polymeric surface. A source of fluid is attached to each channel, and the application of pressure to the source causes the flow of the fluid in the channel. The pressure may be applied by a syringe, a pump, and/or gravity. The inlet streams of solutions with polymer, targeting moieties, lipids, drug, payload, etc. converge and mix, and the resulting mixture is combined with a polymer non-solvent solution to form the nanoparticles having the desired size and density of moieties on the surface. By varying the pressure and flow rate in the inlet channels and the nature and composition of the fluid sources nanoparticles can be produced having reproducible size and structure.

f. Self-Assembly

In some forms, the nanoparticles are formed by self-assembly of amphiphilic block copolymers in an aqueous solution. In an aqueous environment, the amphiphilic copolymers can spontaneously self-assemble to form nanoparticles with a hydrophobic core and a hydrophilic outer shell. In some forms, a solution containing the amphiphilic polymers is mixed with another solution containing a therapeutic, diagnostic, and/or prophylactic agent to be encapsulated. In some forms, the amphiphilic polymers and therapeutic, diagnostic, and/or prophylactic agent to be delivered are dissolved in a suitable solvent, such as tetrahydrofuran, DMSO, or methylene chloride. Preferably, the therapeutic agent is a compound described herein. The concentrations of the amphiphilic polymer and therapeutic, diagnostic, and/or prophylactic agent in the solvent can be varied as needed. After forming a solution containing the amphiphilic polymer and therapeutic, diagnostic, and/or prophylactic agent, the solution can be added continuously to an aqueous solution to induce nanoparticle formation (micellization). The nanoparticle suspensions can be stirred at room temperature, followed by dialysis, placement in an ultrafiltration centrifuge tube, and centrifuging to obtain the nanoparticles.

iii. Liposomal Nanoparticles

Suitable methods, materials and lipids for making liposomes are known in the art. Liposome delivery vehicles are commercially available from multiple sources. Commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art are well known. For example, liposomes can be prepared by modified thin lipid film hydration (Szoka, et al., *Annual review of biophysics and bioengineering,* 9:467-508 (1980).

iv. Inorganic Nanoparticles

The inorganic nanoparticles described herein can be manufactured using well-established methods in the art, such as vapor-phase synthesis, liquid-phase synthesis, solid-phase synthesis, or a combination thereof. Some methods are described in Tsuzuki, *Int. J. Nanotechnol.* 2009, 6(5/6), 567-578, the contents of which are herein incorporated by reference.

The disclosed compounds can be tethered to an inorganic nanoparticle surface through covalent or non-covalent interactions. For example, in some embodiments, the disclosed compounds are tethered to an inorganic nanoparticle surface through electrostatic interaction or hydrophobic-hydrophobic interaction. For inorganic nanoparticles with a porous structure, the compounds can also be trapped inside the particle pores.

IV. Pharmaceutical Compositions

Pharmaceutical compositions including the disclosed compound with or without a particle-based delivery platform are provided. Pharmaceutical compositions can be for, for example, administration by parenteral (e.g., intramuscular, intraperitoneal, intravenous (IV) or subcutaneous) injection or infusion.

In some embodiments, the pharmaceutical composition is a unit dosage containing an effective amount of a disclosed composition. In some embodiments, the unit dosage is in a unit dosage form for intravenous injection. In some embodiments, the unit dosage is in a unit dosage form for intratumoral injection.

In some embodiments, the compositions are administered systemically, for example, by intravenous or intraperitoneal administration, in an amount effective for delivery of the compositions to targeted cells.

In certain embodiments, the compositions are administered locally, for example, by subcutaneous injection, or injection directly into a site to be treated. In some embodiments, the compositions are injected or otherwise administered directly to one or more tumors. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the particles to the immediate area of the implant.

The compounds and particle-based formulations thereof can be provided to the cell either directly, such as by contacting it with the cell, or indirectly, such as through the action of any biological process. For example, the compounds and particle-based formulations thereof can be formulated in a physiologically acceptable carrier or vehicle, and injected into a tissue or fluid surrounding the cell.

A. Formulations for Parenteral Administration

In a preferred embodiment the compositions are administered in an aqueous solution, by parenteral injection.

The formulation can be in the form of a suspension or emulsion. In general, pharmaceutical compositions are provided including an effective amount of a disclosed compound and optionally including pharmaceutically acceptable diluents, preservatives, solubilizers, emulsifiers, adjuvants and/or carriers. Such compositions can include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

B. Other Formulations

The disclosed compounds alone or in a particle formulation can also be applied topically. Topical administration can include application to the lungs, nasal, oral (sublingual, buccal), vaginal, or rectal mucosa. In some embodiments, the compositions are administered in combination with transdermal or mucosal transport elements.

A wide range of mechanical devices designed for pulmonary delivery of therapeutic products can be used, including but not limited to, nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Oral formulations may be in the form of chewing gum, gel strips, tablets, capsules, or lozenges. Oral formulations may include excipients or other modifications to the particle which can confer enteric protection or enhanced delivery through the GI tract, including the intestinal epithelia and mucosa (see Samstein, et al., *Biomaterials,* 29(6):703-8 (2008).

Transdermal formulations may also be prepared. These will typically be ointments, lotions, sprays, or patches, all of which can be prepared using standard technology. Transdermal formulations can include penetration enhancers.

V. Methods of Use

A. Methods of Treatment Methods of use are provided. The experiments below demonstrate the use of an exemplary nanoparticle-based maytansinoid radiosensitizer prodrug (DM1-NO) in the treatment of cancer. Due to nanoparticle (PLGA) encapsulation and S-nitrosylation, the toxicity of DM1 is suppressed, allowing the therapeutic to be delivered systematically to tumors through the EPR effect. Subsequent radiation elevates the oxidative stress in tumors, causing the cleavage of the S—N bond and the release of DM1 and NO, both of which are potent radiosensitizers (FIG. 1A). Specifically, NO reacts with reactive oxygen species (ROS) to form radicals such as peroxynitrites that can effectively oxidize lipids, lipoproteins, and DNA molecules (Bloodsworth et al., *Arterioscler., Thromb., Vasc. Biol.* 20, 1707-1715 (2000)). DM1, on the other hand, leads to mitotic arrest and cell enrichment at the more radiosensitive G2/M phase.

A nanoparticle radiosensitizer that can sensitize NSCLC cells to RT while causing minimal systemic toxicities is highly desirable. In the experiments below, the radiosensitizing effects of DM1-NO were first assessed in vitro by clonogenic assays and then in vivo in a rodent NSCLC tumor model. NSCLC accounts for 85% of all lung cancer cases, and is diagnosed in 234,030 persons in the US alone in 2018 (Jemal et al., *Ca-Cancer J. Clin.* 60, 277-300 (2010)). RT is the standard care for the majority of patients with locally advanced or local regional disease, and is a viable alternative to lobectomy and lymph node dissection for stage I patients (Baker et al., *Radiat. Oncol.* 11, 115 (2016)).

Thus, methods of treating a subject are provided. The methods typically include administering an effective amount of a disclosed compound having one or more S-nitrosothiol moieties to a subject in need thereof. In preferred embodiments, the composition is delivered to the subject in using a particle-based delivery platform.

In the experiments below, mice were administered 200 μl free drug (DM1, DM1-NO) or drug loaded nanoparticles (DM1-NPs, DM1-NO-NP) in PBS at a dose of 260.8 nmol/kg (or about 0.2 mg/kg) by intravenous delivery. As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired.

Generally dosage levels of 0.001 to 10 mg/kg, for example, 0.1 mg/kg to 1 mg/kg, of body weight are administered to mammals. Generally, for local administration, dosage may be lower than for systemic administration. The dosage can be a daily dosage, or any other dosage regimen consistent with the disclosed methods. The timing of the administration of the composition will also depend on the formulation and/or route of administration used. The compound may be administered once daily, but may also be administered two, three or four times daily, or every other day, or once or twice per week. For example, the subject can be administered one or more treatments 1, 2, 3, 4, 5, 6, 7, 8, 9, 10, 11, 12, 13, 14, 15, 16, 17, 18, 19, 20, 21, 22, 23, or 24 hours, days, weeks, or months apart.

The subject can have one or more malignant or non-malignant tumors. In some embodiments, the subject has cancer.

Typically, the composition is administered to the subject in combination with a radiation therapy. Although discussed herein primarily with reference to ionizing radiation therapy, it is believed that the disclosed compounds may also be used as sensitizers for phototherapy and/or proton therapy. Thus, substitution of ionizing radiation with phototherapy or proton therapy in the methods disclosed herein are specifically contemplated and disclosed.

In some embodiments, the compound having one or more S-nitrosothiol moieties is administered in an effective amount to enhance treatment of the tumor or cancer relative to administration of radiation alone, and/or administration of un-S-nitrosylated compound alone or in combination with radiation. In some embodiments, the administration of the compound having one or more S-nitrosothiol moieties has suppressed and/or reduced systemic toxicity compared to administration of the un-S-nitrosylated compound. In preferred embodiments, the compound is an S-nitrosylated maytansinoid compound, such as DM1-NO.

In preferred embodiments, the radiation is ionizing radiation. Ionizing radiation therapy (also referred to as radiotherapy and RT) is the medical use of ionizing radiation as part of cancer treatment to control malignant cells. Ionizing radiation is typically defined as radiation with enough energy to liberate an electron from the orbit of an atom, causing the atom to become charged or ionized. Ionizing radiation can be administered to a subject in need thereof as part of radiation therapy for the treatment for cancer. Examples of radiation therapy include, but are not limited to, external beam radiation therapy (EBRT or XRT) or teletherapy, brachytherapy or sealed source radiation therapy, and systemic radioisotope therapy or unsealed source radiotherapy. The radiation therapy can be administered to the subject externally (i.e., outside the body), or internally for example, brachytherapy which typically utilizes sealed radioactive sources placed in the area under treatment, and or systemic administration of radioisotopes by infusion or oral ingestion. Radiation therapy can include temporary or permanent placement of radioactive sources on or within the subject. Another example of radiation therapy is particle therapy which is typically includes external beam radiation therapy where the particles are protons or heavier ions.

Radiation therapy works by damaging the DNA of dividing cells, e.g., cancer cells. This DNA damage is caused by one of two types of energy, photon or charged particle. This damage is either direct or indirect. Indirect ionization happens as a result of the ionization of water, forming free radicals, notably hydroxyl radicals, which then damage the DNA. For example, most of the radiation effect caused by photon therapy is through free radicals. One of the major limitations of photon radiotherapy is that the cells of solid tumors become deficient in oxygen, and tumor cells in a hypoxic environment may be as much as 2 to 3 times more resistant to radiation damage than those in a normal oxygen environment.

Direct damage to cancer cell DNA occurs through high-LET (linear energy transfer) charged particles such as proton, boron, carbon or neon ions. This damage is independent of tumor oxygen supply because these particles act mostly via direct energy transfer usually causing double-stranded DNA breaks. Due to their relatively large mass, protons and other charged particles have little lateral side scatter in the tissue; the beam does not broaden much, stays focused on the tumor shape and delivers small dose side-effects to surrounding tissue.

The amount of radiation used in photon radiation therapy is measured in Gray (Gy), and varies depending on the type and stage of cancer being treated. For curative cases, the typical dose for a solid epithelial tumor ranges from 60 to 80 Gy, while lymphomas are treated with 20 to 40 Gy. Post-operative (adjuvant) doses are typically around 45-60 Gy in 1.8-2 Gy fractions (for breast, head, and neck cancers). Many other factors are considered by radiation oncologists when selecting a dose, including whether the patient is receiving chemotherapy, patient co-morbidities, whether radiation therapy is being administered before or after surgery, and the degree of success of surgery.

The response of a cancer to radiation is described by its radiosensitivity. Highly radiosensitive cancer cells are rapidly killed by modest doses of radiation. These include leukemias, most lymphomas and germ cell tumors. The majority of epithelial cancers are only moderately radiosensitive, and require a significantly higher dose of radiation (60-70 Gy) to achieve a radical cure. Some types of cancer are notably radioresistant, that is, much higher doses are required to produce a radical cure than may be safe in clinical practice. Renal cell cancer and melanoma are generally considered to be radioresistant.

In some embodiments, the compositions and methods reduce the dose of radiation required to induce a curative or preventative effect. For example, the disclosed compounds can increase a cancer's radiosensitivity. Effective doses of radiation therapy may be toxic for certain cancers. In some embodiments, the compounds decrease the required effective dose of radiation needed to treat a cancer, thereby reducing toxicity of the effective dose of radiation.

In other embodiments, the disclosed compounds may be used with normal doses of drug or radiation to increase efficacy. For example, the compounds may be used to potentiate a radiation therapy for a cancer that is radiation resistant.

The response of a tumor to radiotherapy is also related to its size. For complex reasons, very large tumors respond less well to radiation than smaller tumors or microscopic disease. Various strategies are used to overcome this effect. The most common technique is surgical resection prior to radiotherapy. This is most commonly seen in the treatment of breast cancer with wide local excision or mastectomy followed by adjuvant radiotherapy. Another method is to shrink the tumor with neoadjuvant chemotherapy prior to radical radiotherapy. In some embodiments, the disclosed methods allow for treatment of tumors that are larger than can be treated by a normal dose of radiation.

A third technique is to enhance the radiosensitivity of the cancer by giving certain drugs during a course of radiotherapy. The disclosed compositions can serve this third function. In these embodiments, the compound increases the cell's sensitivity to the radiotherapy, for example, by at least 10%, 15%, 20%, 25%, 30%, 35%, 40%, 45%, 50%. Moreover, the compound can be combined with one or more additional radiosensitizers. Examples of known radiosensitizers include cisplatin, gemcitabine, 5-fluorouracil, pentoxifylline, vinorelbine, PARP inhibitors, histone deacetylase inhibitors, and proteasome inhibitors, and other mentioned elsewhere herein.

Radiation therapy can be administered to a subject in combination with surgery, chemotherapy, hormone therapy, immunotherapy, or combination thereof. For example, intraoperative radiation therapy or (IORT) is delivered immediately after surgical removal of a cancer. This method has been employed in breast cancer (TARGeted Introperative radiation therapy or TARGIT), brain tumors and rectal cancers.

Radiotherapy also has several applications in non-malignant conditions, such as the treatment of trigeminal neuralgia, severe thyroid eye disease, pterygium, pigmented villonodular synovitis, prevention of keloid scar growth, and prevention of heterotopic ossification. Thus, in some embodiments, the compositions and methods are used to increase radiosensitivity for a non-malignant condition.

In other embodiments, the composition is administered to a subject in combination with photodynamic therapy (PDT), where the prodrug serves as a photosensitizer. When prodrug is exposed to a specific wavelength of light, the S—N bond is severed and the parent drug compound and NO are released. One or more additional photosensitizers may also be used.

In other embodiments, the composition is administered to a subject in combination with proton therapy, where the prodrug serves as a sensitizer. When prodrug is exposed to proton radiation, the S—N bond is severed and the parent drug compound and NO are released.

Typically, the prodrug composition is administered before, e.g., minutes, hours, or days before, a radiation therapy. For example, in exemplary embodiments, a dose of radiation is administered 1 hour to 48 hours, or 1 hour to 24 hours, or 1 hour to 12 hours, or 1 hour to 6 hours, or 2 hours to 6 hours, or 1, 2, 3, 4, or 5 hours after administration of the pharmaceutical composition. In some embodiments, 1, 2, 3, 4, or 5 rounds are radiation are administered after each single dose of the prodrug. In some embodiments, the prodrug is administered one or more times for each round of radiation. In some embodiments, each cycle of radiation is preceded by a cycle of prodrug. For example, in particular embodiments, 1, 2, 3, 4, 5, 6, 7, 8, 9, 10, or more rounds of administration of the pharmaceutical composition followed by administration of the dose of radiation are carried out in tandem.

In some embodiments, the disclosed compositions and methods are more effective, less toxic, or combination thereof relative to a specific concurrent or sequential chemoradiotherapy (CRT). In some embodiments, the chemotherapeutic element(s) of the CRT is platinum-based doublet, optionally administered concurrently with radiation. In a more specific embodiment, the disclosed compositions and methods are more effective, less toxic, or a combination thereof relative to a cisplatin+etoposide CRT regimen.

B. Cancers to be Treated

The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth. The treatment is also useful for reducing overproliferation of non-cancerous tissues such as endometriosis, restenosis, and scarring (fibrosis).

Malignant tumors which may be treated are classified according to the embryonic origin of the tissue from which the tumor is derived. Carcinomas are tumors arising from endodermal or ectodermal tissues such as skin or the epithelial lining of internal organs and glands. The disclosed compositions are particularly effective in treating carcinomas. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, cancers such as vascular cancer such as multiple myeloma, adenocarcinomas and sarcomas, of bone, bladder, brain, breast, cervical, colo-rectal, esophageal, kidney, liver, lung, nasopharangeal, pancreatic, prostate, skin, stomach, and uterine. In some embodiments, the disclosed compositions are used to treat multiple cancer types concurrently. The compositions can also be used to treat metastases or tumors at multiple locations.

In some embodiments, the cancer is a highly radiosensitive, moderately radiosensitive cancer, or radioinsensitive (i.e., low radiosensitive cancer). Highly radiosensitive cancer cells are rapidly killed by modest doses of radiation. Tissues rich in actively dividing cells generally show high sensitivity to radiation, whereas those with few such cells have low radiosensitivity (Hayabuchi, *JMAJ,* 47(2): 79-83 (2004)). For example, genital glands such as the testis and ovary, lymphatic tissue, fetal tissue, and fetus-like blast cell tissue are highly radiosensitive. Tissues with low radiosensitivity include adult bone, fatty tissue, muscle, and large vessels. Because the radiosensitivity of a tumor reflects the sensitivity of the tissue from which it has arisen, malignant lymphomas, which originate in lymphatic tissue, and seminomas, which originate in the testis, have high sensitivity to radiation. In contrast, osteogenic sarcomas and liposarcomas demonstrate low radiosensitivity.

Epithelial tumors and cancers, are considered to have moderate radiosensitivity. Such cancers can require a significantly higher dose of radiation (60-70 Gy) to achieve a cure. Among these tumors, undifferentiated carcinoma and small cell carcinoma have relatively high radiosensitivity, followed by squamous cell carcinoma. The radiosensitivity of adenocarcinoma is generally lower than that of other types of epithelial tumors. In light of this, head and neck cancer, esophageal cancer, uterine cervical cancer, and skin cancer, among which squamous cell carcinoma is common, seem to be good indications for radiotherapy.

However, even among squamous cell carcinomas of the esophagus, some are highly radiosensitive but others are not. Radiosensitivity can depend not only on the histologic type of the tumor but also on other factors, for example, the oxygen concentration in the tumor and the mitotic cycle of tumor cells.

Renal cell cancer and melanoma are generally considered to be radioresistant.

In particular embodiments, the cancer is a lung cancer, for example, a non-small cell lung cancer (NSCLC). In other embodiments the cancer is a head and neck, breast, or colon cancer.

In some embodiments, particularly those wherein nanoparticles feature an NTSR1 targeting signal, the cancer has upregulated NTSR1. In some embodiments, the cancer in which NTSR1 is upregulated is a lung cancer, for example, a non-small cell lung cancer (NSCLC), a head and neck, breast, or colon cancer.

The disclosed compositions and methods can be further understood through the following numbered paragraphs.

1. A compound containing the structural motif:

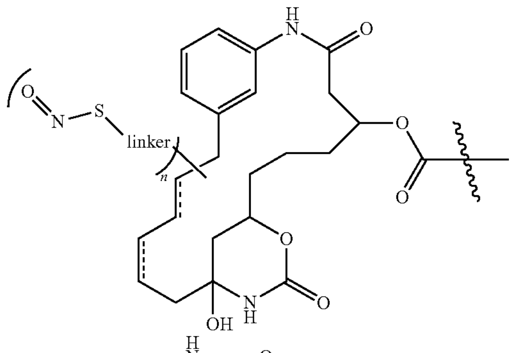

or

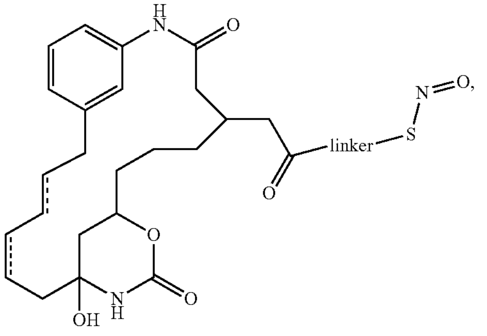

wherein:

n is an integer between 1 and 13, inclusive, the dashed lines indicate the presence or absence of a bond, and the corresponding carbon atoms have none, one, or two hydrogen atoms attached to each according to valency, and "linker" is, independently, absent, substituted amido, unsubstituted amido, substituted alkyl, substituted alkylene, unsubstituted alkylene, substituted aryl, substituted heteroaryl, substituted alkenyl, substituted alkynyl, substituted alkoxy, substituted aroxy, substituted alkylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, substituted polyaryl, substituted $C_3$-$C_{20}$ cyclic, or substituted $C_3$-$C_{20}$ heterocyclic.

2. The compound of paragraph 1, having the structure:

Formula I

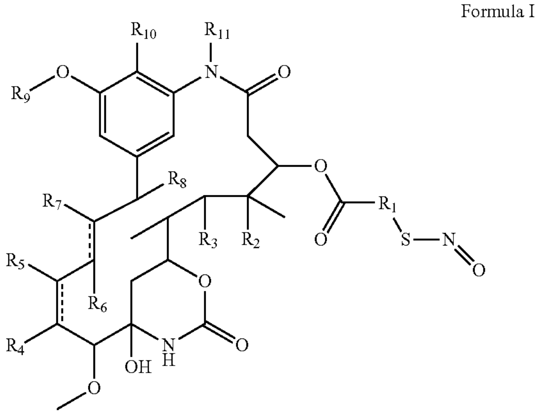

Formula I(a)

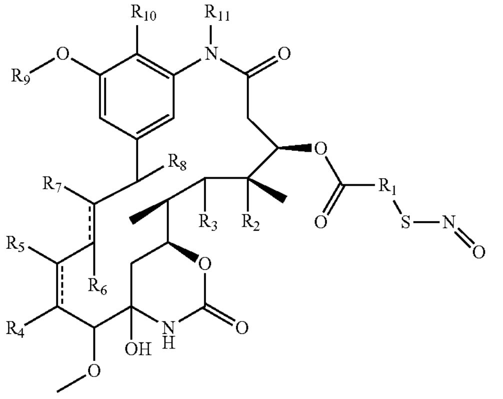

wherein:

$R_1$ is substituted amido, unsubstituted amido, substituted alkyl, substituted alkylene, unsubstituted alkylene, substituted aryl, substituted heteroaryl, substituted alkenyl, substituted alkynyl, substituted alkoxy, substituted aroxy, substituted alkylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, substituted polyaryl, substituted $C_3$-$C_{20}$ cyclic, or substituted $C_3$-$C_{20}$ heterocyclic, and $R_2$, $R_3$, $R_4$, $R_5$, $R_6$, $R_7$, $R_8$, $R_9$, $R_{10}$, and $R_{11}$ are independently hydrogen, halogen (F, Br, Cl, I), substituted alkyl, unsubstituted alkyl, substituted aryl, unsubstituted aryl, substituted heteroaryl, unsubstituted heteroaryl, unsubstituted alkenyl, substituted alkenyl, unsubstituted alkynyl, substituted alkynyl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic, or $R_2$ and $R_3$ together with the carbon atoms to which they are bonded an epoxide.

3. The compound of paragraph 2, $R_1$ is substituted $C_1$-$C_{10}$ amido, unsubstituted $C_1$-$C_{10}$ amido, substituted $C_1$-$C_{10}$ alkyl, unsubstituted $C_1$-$C_{10}$ alkylene, substituted $C_1$-$C_{10}$ alkylene, unsubstituted $C_1$-$C_{10}$ alkylene, substituted aryl, substituted heteroaryl, substituted $C_2$-$C_{10}$ alkenyl, substituted $C_2$-$C_{10}$ alkynyl, substituted $C_1$-$C_{10}$ alkoxy, substituted aroxy, substituted $C_1$-$C_{10}$ alkylthio, substituted arylthio, unsubstituted $C_1$-$C_{10}$ carbonyl, substituted $C_1$-$C_{10}$ carbonyl, unsubstituted $C_1$-$C_{10}$ carboxyl, substituted $C_1$-$C_{10}$ carboxyl, unsubstituted $C_1$-$C_{10}$ amino, substituted $C_1$-$C_{10}$ amino, unsubstituted $C_1$-$C_{10}$ sulfonyl, substituted $C_1$-$C_{10}$ sulfonyl, unsubstituted $C_1$-$C_{10}$ sulfamoyl, substituted $C_1$-$C_{10}$ sulfamoyl, unsubstituted $C_1$-$C_{10}$ phosphonyl, substituted $C_1$-$C_{10}$ phosphonyl, substituted polyaryl, substituted $C_3$-$C_{10}$ cyclic, or substituted $C_3$-$C_{10}$ heterocyclic, preferably wherein $R_1$ is substituted $C_1$-$C_{10}$ amido or unsubstituted $C_1$-$C_{10}$ amido.

4. The compound of paragraphs 2 or 3, wherein $R_1$ has the structure:

Formula II

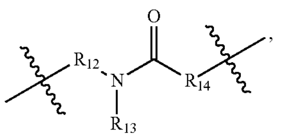

wherein $R_{12}$ is substituted $C_1$-$C_5$ alkylene or unsubstituted $C_1$-$C_5$ alkylene, $R_{13}$ is hydrogen, substituted $C_1$-$C_5$ alkyl, or unsubstituted $C_1$-$C_5$ alky, and $R_{14}$ is substituted $C_1$-$C_5$ alkylene or unsubstituted $C_1$-$C_5$ alkylene, preferably $R_{12}$ is substituted $C_1$-$C_5$ alkylene (preferably —$CH(CH_3)$—), $R_{12}$ is unsubstituted $C_1$-$C_5$ alkyl (preferably —$CH_3$), and $R_{14}$ is unsubstituted $C_1$-$C_5$ alkylene (preferably —$(CH_2)_2$—).

5. The compound of any one of paragraphs 2 to 4, having a structure selected from:

Formula III

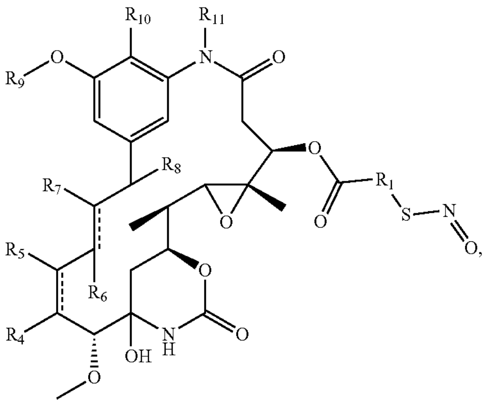

-continued

Formula IV

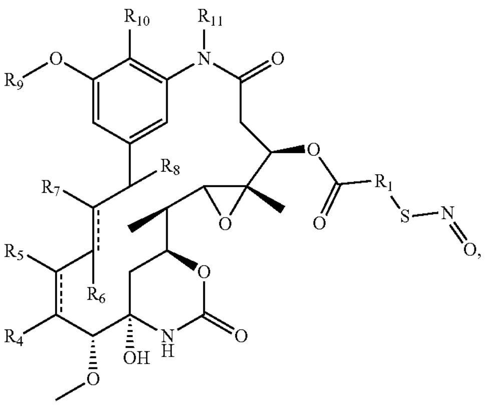

Formula V

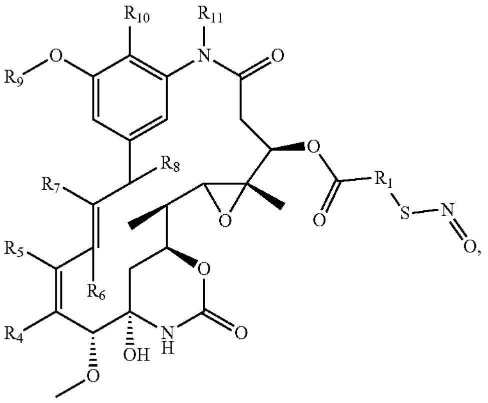

Formula VI

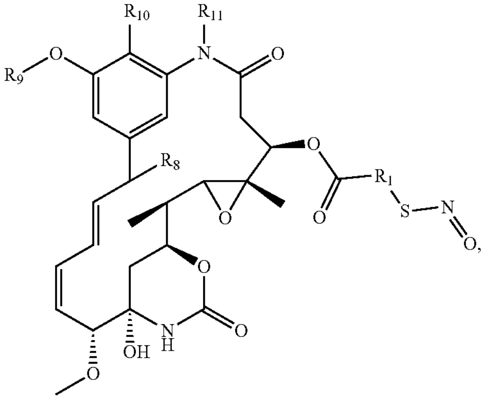

-continued

Formula VII

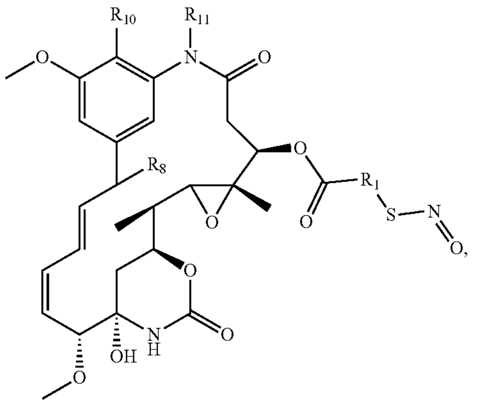

Formula VIII

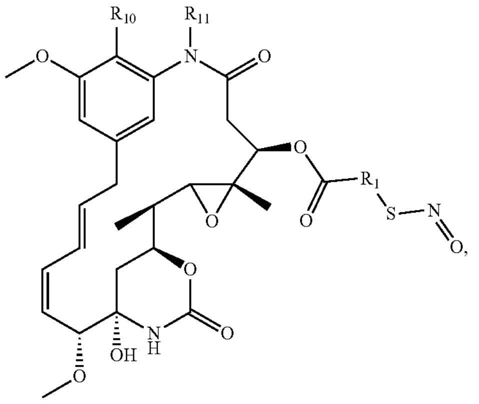

Formula IX

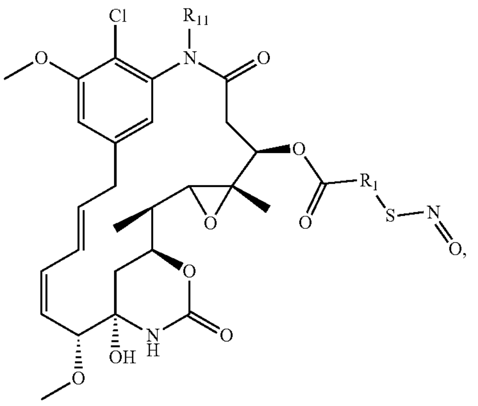

or

-continued

Formula X

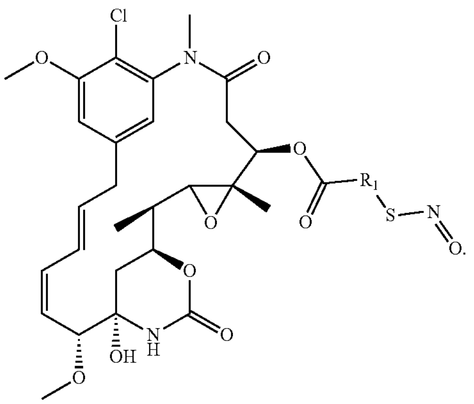

6. The compound of any one of paragraphs 2 to 5, wherein when present $R_2$, $R_3$, $R_4$, $R_5$, $R_6$, $R_7$, $R_8$, $R_9$, $R_{10}$, and $R_{11}$ are independently hydrogen, hydroxy, halogen (F, Br, Cl, I), substituted $C_1$-$C_5$ alkyl, unsubstituted $C_1$-$C_5$ alkyl, substituted aryl, unsubstituted aryl, substituted heteroaryl, unsubstituted heteroaryl, unsubstituted $C_1$-$C_5$ alkenyl, substituted $C_1$-$C_5$ alkenyl, unsubstituted $C_1$-$C_5$ alkynyl, substituted $C_1$-$C_5$ alkynyl, unsubstituted $C_1$-$C_5$ alkoxy, substituted $C_1$-$C_5$ alkoxy, unsubstituted aroxy, substituted aroxy, unsubstituted $C_1$-$C_5$ alkylthio, substituted $C_1$-$C_5$ alkylthio, unsubstituted arylthio, substituted arylthio, unsubstituted $C_1$-$C_5$ carbonyl, substituted $C_1$-$C_5$ carbonyl, unsubstituted $C_1$-$C_5$ carboxyl, substituted $C_1$-$C_5$ carboxyl, unsubstituted $C_1$-$C_5$ amino, substituted $C_1$-$C_5$ amino, unsubstituted $C_1$-$C_5$ sulfonyl, substituted $C_1$-$C_5$ sulfonyl, unsubstituted $C_1$-$C_5$ sulfamoyl, substituted $C_1$-$C_5$ sulfamoyl, unsubstituted $C_1$-$C_5$ phosphonyl, substituted $C_1$-$C_5$ phosphonyl, unsubstituted polyaryl, substituted polyaryl, unsubstituted $C_3$-$C_6$ cyclic, substituted $C_3$-$C_6$ cyclic, unsubstituted $C_3$-$C_6$ heterocyclic, or substituted $C_3$-$C_6$ heterocyclic.

7. The compound of any one of paragraphs 2 to 6, wherein when present $R_2$ and $R_3$ together with the carbon atoms to which they are bonded are an epoxide.

8. The compound of any one of paragraphs 2 to 7, wherein when present $R_4$, $R_5$, $R_6$, and $R_7$ are independently hydrogen, hydroxy, halogen (F, Br, Cl, I), substituted $C_1$-$C_5$ alkyl, unsubstituted $C_1$-$C_5$ alkyl, substituted aryl, unsubstituted aryl, substituted heteroaryl, or unsubstituted heteroaryl, preferably, $R_4$, $R_5$, and $R_6$ are hydrogen, and $R_7$ is methyl.

9. The compound of any one of paragraphs 2 to 8, wherein when present $R_8$ is hydrogen, hydroxy, halogen (F, Br, Cl, I), substituted $C_1$-$C_5$ carboxyl, unsubstituted $C_1$-$C_5$ carboxyl, substituted $C_1$-$C_5$ carbonyl, or unsubstituted $C_1$-$C_5$ carbonyl, preferably $R_8$ is hydrogen, hydroxy, substituted $C_1$-$C_5$ carboxyl, or unsubstituted $C_1$-$C_5$ carboxyl, or preferably $R_8$ is hydrogen.

10. The compound of any one of paragraphs 2 to 9, wherein when present $R_9$ is hydrogen, substituted $C_1$-$C_5$ alkyl, unsubstituted $C_1$-$C_5$ alkyl, substituted $C_1$-$C_5$ carbonyl, or unsubstituted $C_1$-$C_5$ carbonyl, preferably $R_9$ is unsubstituted $C_1$-$C_5$ alkyl, or preferably $R_9$ is methyl.

11. The compound of any one of paragraphs 2 to 10, wherein when present $R_{10}$ is a halogen (F, Cl, Br, I), substituted $C_1$-$C_5$ alkyl, unsubstituted $C_1$-$C_5$ alkyl, substituted $C_1$-$C_5$ carbonyl, or unsubstituted $C_1$-$C_5$ carbonyl, preferably $R_{10}$ is a halogen, or preferably $R_{10}$ is Cl.

12. The compound of any one of paragraphs 2 to 11, wherein when present $R_{11}$ is hydrogen, substituted $C_1$-$C_5$ alkyl, unsubstituted $C_1$-$C_5$ alkyl, substituted aryl, unsubstituted aryl, substituted heteroaryl, or unsubstituted heteroaryl, preferably $R_{11}$ is unsubstituted $C_1$-$C_5$ alkyl, or preferably $R_{11}$ is methyl.
13. The compound of any one of paragraphs 2 to 12, having the structure:

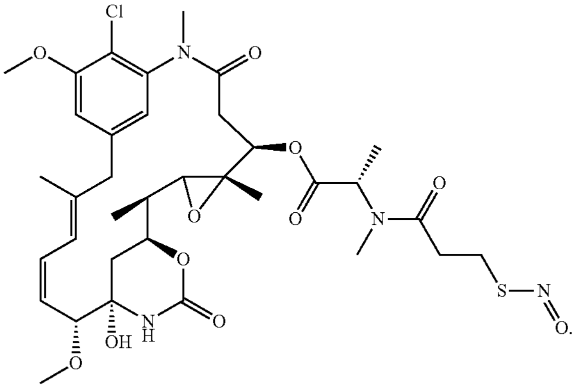 [SMILES: COc1cc2cc(c1Cl)N(C)C(=O)C[C@@H](OC(=O)[C@H](C)N(C)C(=O)CCSN=O)[C@]1(C)OC1[C@H](C)[C@@H]1C[C@@](O)(NC(=O)O1)[C@H](OC)/C=C\C=C(/C)C2]

14. A compound comprising an analog of a radiosensitizer parent compound comprising one or more S-nitrosothiol moieties, wherein the S—N bond of the S-nitrosothiol moiet(ies) is cleavable by radiation, preferably ionizing radiation, during radiotherapy and releases the parent compound and nitric oxide.
15. The compound of paragraph 14, wherein the parent compound is nicotinamide, metronidazole or an analog thereof, optionally selected from misoniszole, etanidazole, and nimorazole; a hypoxic cell cytotoxic agent, optionally selected from mitomycin-C and tirapazamine; a membrane active agent optionally selected from procaine, lidocaine, and chlorpromazine; a radiosensitizing nucleoside optionally selected from 5-fluorouracil, fluorodeoxyuridine bromodeoxyuridine, lododeoxyuridine, hydroxyurea, gemcitabine, and fludarabine, a texaphryin optionally selected from motexafin gadolinium; a suppressor of sulfhydral groups optionally selected from N-ethylmaleimide, diamide, and diethylmaleate; a chemotherapeutic agent optionally selected from paclitaxel, docetaxel, irinotecan, and cisplatin; pentoxifylline; vinorelbine; a PARP inhibitor; a histone deacetylase inhibitor; and a proteasome inhibitor.
16. A nanoparticle comprising the compound of any one of paragraphs 1-15.
17. The nanoparticle of paragraph 16, wherein the nanoparticle is a polymeric nanoparticle, liposome, inorganic nanoparticle.
18. The nanoparticle of paragraph 17, wherein the nanoparticle is a polymeric nanoparticle comprising one or more amphiphilic, hydrophobic, and/or hydrophilic polymers.
19. The nanoparticle of any one of paragraphs 16-18, wherein the nanoparticle comprises one or more hydrophobic polymers.
20. The nanoparticle of paragraph 19, wherein one or more of hydrophobic polymers is polyester.
21. The nanoparticle of paragraph 20, wherein the polyester or polyesters are selected from poly(lactic acid-co-glycolic acid)s, poly(lactic acid), poly(glycolic acid).
22. The nanoparticle of any one of paragraphs 16-21, wherein the nanoparticle comprises poly(lactic acid-co-glycolic acid) (PLGA). 23. The nanoparticle of any of paragraphs 16-22, wherein the nanoparticle comprises one or more hydrophilic polymers.
24. The nanoparticle of paragraph 23, wherein one or more of the hydrophilic polymers is a polyalkylene glycol.
25. The nanoparticle of any one of paragraphs 16-24, wherein the nanoparticle comprises polyethylene glycol (PEG).
26. The nanoparticle of any one of paragraphs 16-25, wherein the nanoparticle is a polymeric nanoparticle comprising poly(lactide-co-glycolic)-block-poly(ethylene glycol) (PLGA-b-PEG).
27. The nanoparticle of any one of paragraphs 16-26 having a size suitable for delivery of the compound to tumor microenvironments by enhanced permeability and retention.
28. The nanoparticle of any one of paragraphs 16-27, wherein the nanoparticle having a size of about 10 nm to about 300 nm.
29. The nanoparticle of any one of paragraphs 16-28, further comprising a targeting agent coupled thereto.
30. The nanoparticle of paragraph 29, wherein the targeting agent targets NTSR1.
31. The nanoparticle of paragraph 30, wherein the targeting agent is an agonist or antagonist for NTSR1.
32. The nanoparticle of paragraph 31, wherein the targeting agent is NTS or a variant thereof.
33. The nanoparticle of paragraph 32, wherein targeting agent is $NTS_{mut}$.
34. The nanoparticle of paragraph 31, wherein the targeting agent is SR142948A or $NTS_{20.8}$.
35. A pharmaceutical composition comprising an effective amount of the compound of any one of paragraphs 1-15.
36. A pharmaceutical composition comprising an effective amount of the nanoparticles of any one of paragraphs 16-34.
37. A method of treating a subject in need thereof comprising administering the subject the pharmaceutical composition of paragraph 35.
38. A method of treating a subject in need thereof comprising administering the subject the pharmaceutical composition of paragraph 36.
39. The method of paragraphs 37 and 38 wherein the subject has cancer.
40. The method of any one of paragraphs 37-39, further comprising administering the subject one or more doses of radiation therapy, optionally wherein the radiation therapy is ionizing radiation therapy, phototherapy, or proton therapy.
41. The method of paragraph 40, wherein the compound enhances the treatment of the cancer compared to administration of the radiation alone.
42. The method of any one of paragraphs 39-41, wherein the cancer is a radiosensitive cancer.
43. The method of any one of paragraphs 39-41, wherein the cancer is a radioresistant cancer.
44. The method of any one of paragraphs 39-43, wherein the cancer a vascular, bone, muscle, bladder, brain, breast, cervical, colo-rectal, esophageal, kidney, liver, lung, nasopharangeal, pancreatic, prostate, skin, stomach, uterine, or germ cell.

45. The method of any one of paragraphs 39-43, wherein the cancer is an epithelial cancer.
46. The method of any one of paragraphs 39-43, wherein the cancer is a non-small cell lung cancer (NSCLC).
47. The method of any one of paragraphs 40-46, wherein the same dose of radiation is more effective than when administered in the absence of the pharmaceutical composition, a lower dose of radiation the same effectiveness as a higher dose when administered in the absence of the pharmaceutical composition, or a combination thereof.
48. The method of any one of paragraphs 37-46, wherein a dose of radiation is administered after administration of the pharmaceutical composition.
49. The method of paragraph 48, wherein the dose of radiation is administered 1 to 48 hours, or 1 to 24 hours, or 1 to 12 hours, or 1 to 6 hours, or 2 to 6 hours, or 1, 2, 3, 4, or 5 hours after administration of the pharmaceutical composition.
50. The method of paragraphs 48 or 49, comprising 1, 2, 3, 4, 5, 6, 7, 8, 9, 10, or more rounds of administration of the pharmaceutical composition followed by administration of the dose of radiation.
51. The method of any one of paragraphs 40-50, wherein the radiation is ionizing radiation.
52. The method of any one of paragraphs 39-51, wherein the cancer comprises cells with upregulated NTSR1.

EXAMPLES

Example 1: DM1 can be Nitrosylated and Formulated in a Particle Delivery System

Materials and Methods

Materials

All required chemicals were used without further purification unless otherwise noted. 1-Ethyl-3-[3-dimethylamino-propyl]carbodiimide hydrochloride (EDC), N-hydroxysuccinimide (NHS), (2-hydroxyethyl), 3-(4,5-dimethylthiazol-2-yl)-2, 5-diphenyltetrazolium bromide (MTT), tert-butyl nitrate, polyethylene glycol (PEG, molecular weight of 2000), DMAP (dimethylaminopyridine), DCC (N,N'-dicyclohexylcarbodiimide), hydrogen peroxide solution (30 wt. % in $H_2O$), methylene chloride (DCM), Methylene blue (MB), Dimethyl Sulfoxide (DMSO) other chemicals were all purchased from Sigma.

Carboxyl terminated PLGA (poly(D,L-lactide-co-glycolide) (dL/g, 0.15 to 0.25) was obtained from Lactel (Birmingham, Ala., USA). Mertansine (DM1) was purchased from MeedKoo Bioscience Inc. Phosphate-buffered saline (PBS, pH 7.4, containing 138 mM NaCl, 2.7 mM KCl, and 10 mM sodium phosphate) was used for all in vitro experiments. RPMI 1640 media, with L-glutamine (HyClone, GE Bioscience, USA) and trypsin-EDTA were purchased from Corning (Manassas, Va. 20109). The antibiotic penicillin-streptomycin (Pen-Strep, MediaTech, USA) and fetal bovine serum (FBS) were purchased from Gibco-Life Technologies (Grand Island, N.Y. 14072). H1299 non-small lungs cancer cells (NSLC) were originally obtained from American Type Culture Collection (ATCC). Free thiol assay and Superoxide Dismutase (SOD) assay kits were obtained from Cayman Chemical (USA). Griess Reagent was obtained from Promega (USA). Nitric oxide dye DMF-FM was purchased from Thermo Scientific.

Synthesis of DM1-NO Prodrug (S-Nitrosation of DM1):

S-nitrosation of DM1 was achieved by following a reported protocol without modifications (Chipinda, et al., *J. Phys. Chem. B,* 110, 5052-5061 (2006), Pant, et al., *ACS Appl. Mater. Interfaces,* 9, 15254-15264 (2017)). Briefly, DM1 was dissolved in DMSO, and tert-butyl nitrite at a molar ratio of 5:1 was added dropwise under gentle stirring to the reaction mixture. The resulting mixture was stirred in the dark for 45 min using a magnetic stirrer. Thereafter, the reaction vessel was placed in an ice bath to precipitate the DM1-NO drug. The resulting compound was filtered, rinsed with in anhydrous DMSO, purified by HyperSep C18 column, and stored at −20° C. before use.

Characterization of the DM1-NO Prodrug

The new compound (2) was characterized by high-resolution electrospray ionization mass spectrometry (HRMS-ESI), and $^1$H-NMR spectroscopy. Mass spectrometry was performed to confirm the structure by loading the sample into a HRMS-ESI chamber through ionization source. The calculated theoretical isotope distribution of compound (1), molecular formula ($C_{35}H_{48}ClN_3O_{10}S$=737.29) and compound (2), molecular formula ($C_{34}H_{48}ClN_4O_{11}S$=766.29). The major peak was observed at 760.29 for compound (1) and 789.254 for compound (2), which agree well with the theoretical calculated m/z values of $[M+Na]^+$.

Compound (1)

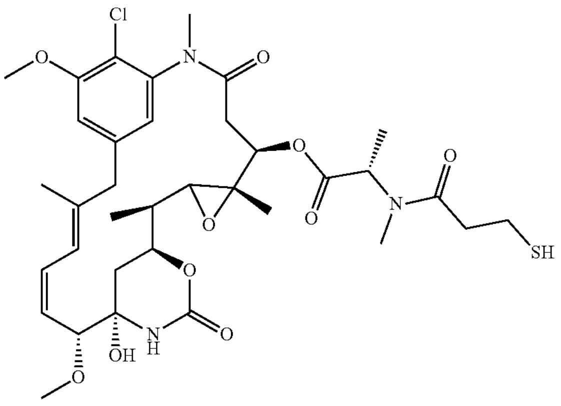

DM1

Compound (2)

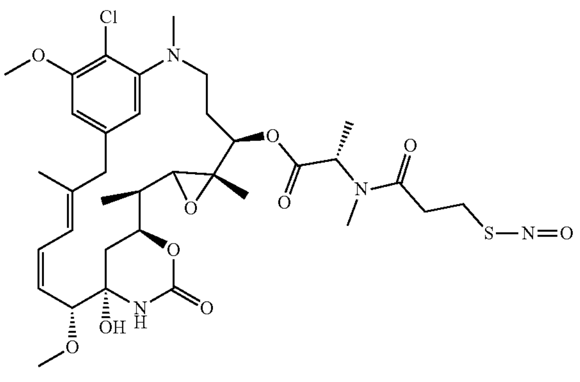

DM1-NO

Synthesis and Characterization of PLGA-b-PEG

The synthesis of PLGA-b-PEG followed a published protocol with slight modifications (below) (Cheng, et al., *Biomaterials,* 28, 869-876 (2007)).

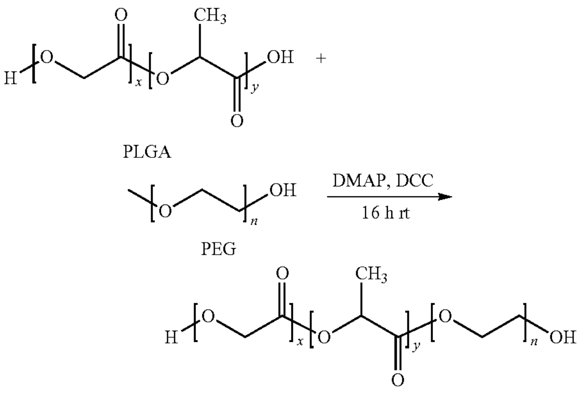

PLGA
PEG
PLGA-b-PEG-OH

Reaction Scheme for PLGA-PEGylation

Briefly, PEG (2.29 g, 0.684 mmol), PLGA-COOH (1.0 g, 0.170 mmol), and 4-di methylaminopyridine (0.023 g, 0.187 mmol) were mixed in 30 mL of dry methylene chloride $CH_2Cl_2$. Next, a 10 mL $CH_2Cl_2$ solution of N,N'-dicyclohexycarbodiimide (DCC, 0.141 g or 0.684 mmol) was dropwise added to the reaction mixture at 0° C. with stirring. The mixture was warmed up to room temperature and stirred overnight. Insoluble dicyclohexylurea was filtered out. The raw product was precipitated out by adding 50 mL of 50:50 diethyl ether and methanol to the mixture. The mixture was centrifuged for 15 min at 4° C. The purification step was repeated 4-5 times. The resulting white pallet was dried under high vacuum to obtain the polymer product. The yield was 68-73%. The $^1$H-NMR ($CHCl_3$-d) data for PLGA-b-PEG showed: δ 5.20 [m, ($OCHCH_3C(O)$)], 4.82 [m, ($OCH_2C(O)$)], 3.63 [s, ($OCH_2$)], 1.57 [m, ($CH_3CH$)].

Synthesis and Characterization of Nanoparticles

In brief, the polymer was dissolved in DMSO to a final polymer concentration of 5 mg/mL and was mixed completely with 1.5 mg/mL of drug (30% concentration with respect to polymer concentration). The mixture was then added dropwise to nanopure water (Millipore) under vigorous stirring. The nanoparticles (NPs) were allowed to self-assemble for 2 h with continuous stirring at room temperature. The NPs were washed four times with nanopore water through an Amcon Ultra-15 centrifugal filter unit (Millipore, Billerica, Mass., USA) with a molecular cutoff of 100-kDa. After purification, the NP solutions were resuspended in PBS (1×) and stored at 4° C. until further use.

Figure 1C:
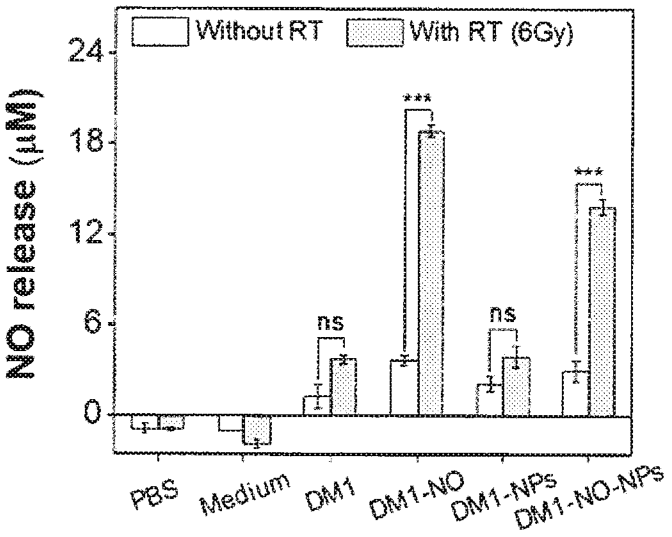
FIG. 1C is a bar graph showing NO release increased from 3.68 μM to 18.88 μM with DM1-NO and from 2.96 μM to 13.87 μM with DM1-NO-NPs in the presence of 6 Gy X-ray irradiation. Quantification was based on Greiss assay. PBS, cell culture medium (RPBI-1640), DM1, and DM1-NPs were tested as controls.
Figure 1D:
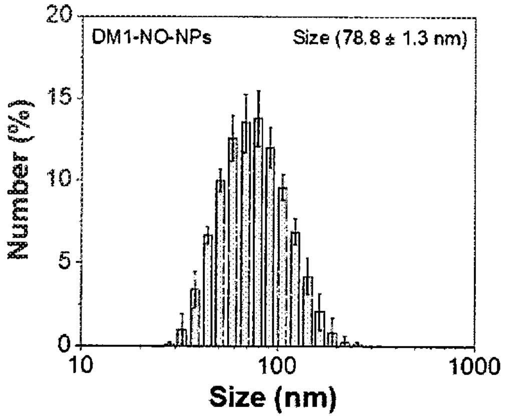
FIG. 1D is a histogram showing the results of DLS analysis of DM1-NO-NPs in water.
Figure 1E:
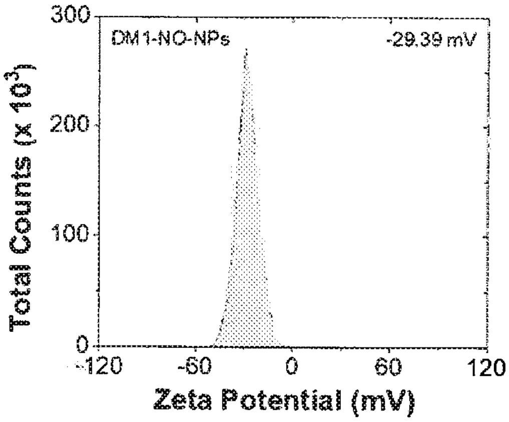
FIG. 1E is a plot showing the zeta potential of DM1-NO-NPs in water.
Figure 1F:
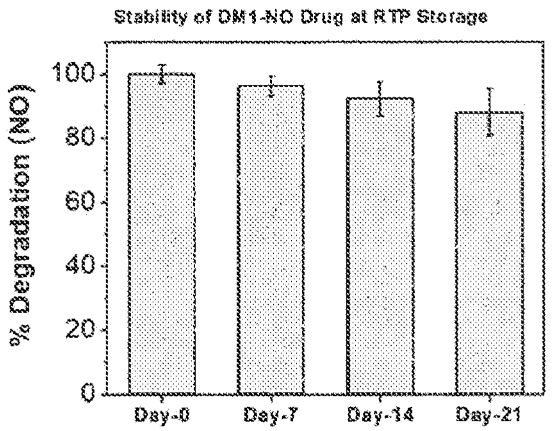
FIG. 1F is a bar graph illustrating the stability of DM1-NO under ambient conditions. After synthesis, dry product of DM1-NO was kept at room temperature and the total amount of remaining NO was quantified using Griess assay on Day 0, 7, 14, and 21.

The physical characteristics of the NPs (e.g. size distribution and zeta potential) were characterized using a dynamic light scattering (DLS) instrument (Malvern Zetasizer Nano S90). The morphology of the NPs was determined using transmission electron microscopy (TEM) (FBI Tecnai20, 200 kV). The cumulative drug release of the nanoparticles studied at pH 5.0, 6.5 and 7.4 was assess by fluorometric thiol assay (FIG. 1H).

Quantification of Drug and Nitric Oxide Release

The amount of drug loaded into polymeric NPs was quantified by the fluorometric thiol assay (Winther, et al., *Biochim. Biophys. Acta,* 1840, 838-846 (2014)). This method is 400-fold more sensitive than the colorimetric method (Ellman's reagent), according to the manufacturer's protocol (Cayman Chemical, Anne Arbor, Mich., USA). The corresponding amount of drug loaded into the NPs was quantitatively measured by comparing to a standard curve. NP solution with no loaded drug (Empty-NPs) was used as the negative control. The drug loading capacity of this drug in the NPs was found to be around 3.8% and the encapsulation efficiency to be around 43%. Both values are comparable with PLGA NPs loaded with other drugs (Tian, et al., *J. Mater. Chem. B,* 5 (30), 6049-6057 (2017)).

NO concentration was assessed to determine the amount of DM1-NO prodrug loaded into the DM1-NO-NPs. NO undergoes a series of reactions with several molecules in solutions. Therefore, to quantify the overall NO amount, the total nitrite (NO2-) and nitrate (NO3-) concentrations in a NP solution cells) were measured using Nitrate/Nitrite Colorimetric assay (Cayman Chemical) by following the vendor's protocol.

Results

DM1-NO was synthesized by reacting DM1 with tert-butyl nitrite in anhydrous DMSO. See a reaction scheme for DM1-NO synthesis illustrated below.

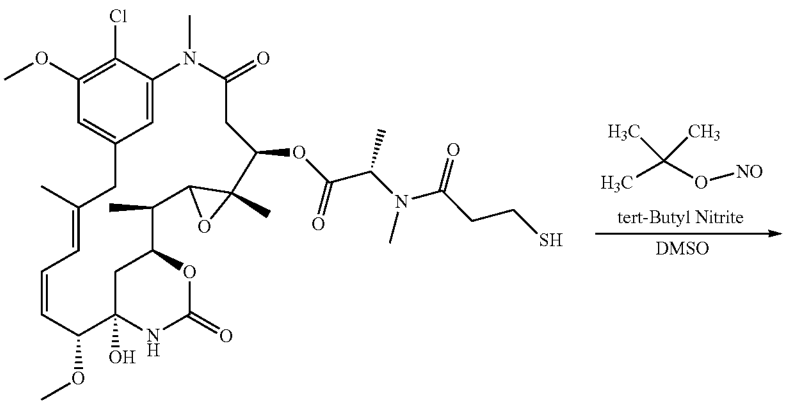

Mertansine (DM1)

-continued

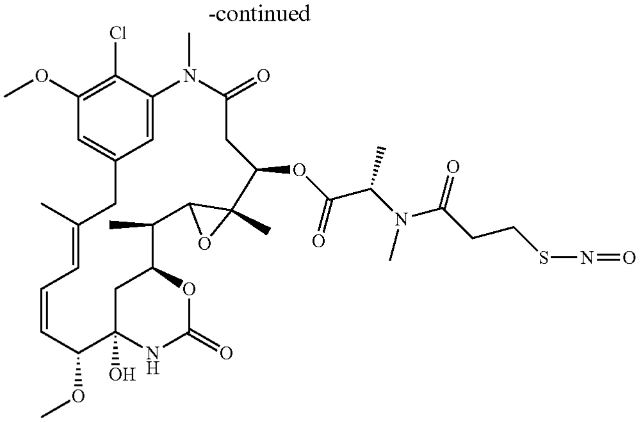

S-Nitroso-Mertansine (DM1-NO)

The resulting compound was purified on a flash column. 1H-NMR analysis found that the peak at δ=6.0 ppm disappeared after the reaction, indicating successful nitrosation of the DM1 thiol group. High resolution electrospray ionization mass spectrometry found a main peak at 789.2548, which agrees with the calculated m/z of [M+Na]+. The DM1-NO product was analyzed on a Sievers NOA 280i system, which measures NO levels based on a gas phase chemiluminescence reaction between NO and ozone. According to the analysis, the yield of DM1-NO was 86%.

DM1-NO was stable under ambient conditions in the powder form. According to Griess assay, less than 10% of the compound was degraded over 2 weeks' storage at room temperature (FIG. 1F). DM1-NO gradually broke down in PBS at 37° C. (FIG. 1G), and the degradation was accelerated at low pH (e.g. pH 6.5 or 5.5, FIG. 1G, Table 1), and under X-ray irradiation (FIG. 1C).

TABLE 1

Figure 1G:
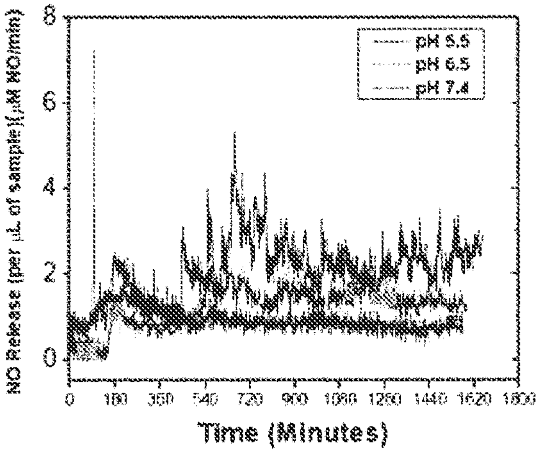
FIG. 1G is plot illustrating the stability of DM1-NO in solutions. DM1-NO (20.09 μmol) was dissolved in PBS of different pH (5.5, 6.5, and 7.4). Time-dependent NO release was measured on a Sievers NOA 280i system, which assesses NO based on gas phase chemiluminescent reaction between NO and ozone.
Figure 1H:
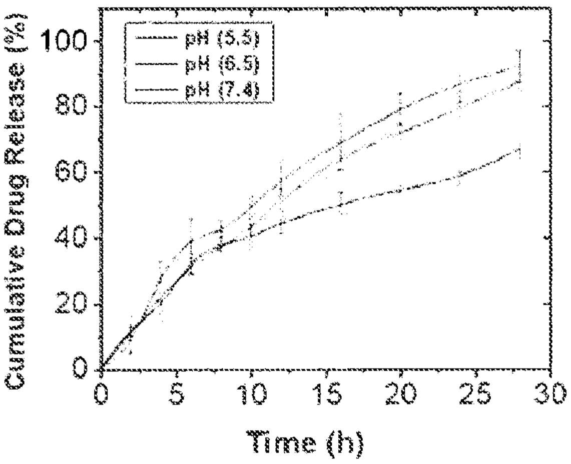
FIG. 1H is a line graph showing release profiles for DM1-NO-NPs, tested in PBS of different pH at 37° C. by Greiss assays.

| NO releases corresponding to FIG. 1G | | |
|---|---|---|
| pH | Average NO Release (per μL of sample) (μmol NO/min) | |
| 5.5 | 1.29E−07 | 9.91E−09 |
| 6.5 | 7.81E−08 | 2.42E−09 |
| 7.4 | 7.83E−08 | 2.37E−09 |

For instance, when 6 Gy X-ray irradiation was applied to solutions containing DM1-NO, NO release was increased by 5.14-fold (FIG. 1C). This enhanced degradation was attributed to OH radicals generated through water radiolysis (Azzam et al., *Cancer Lett.* 327, 48-60 (2012)) which facilitated DM1-NO oxidation.

Figure 1I:
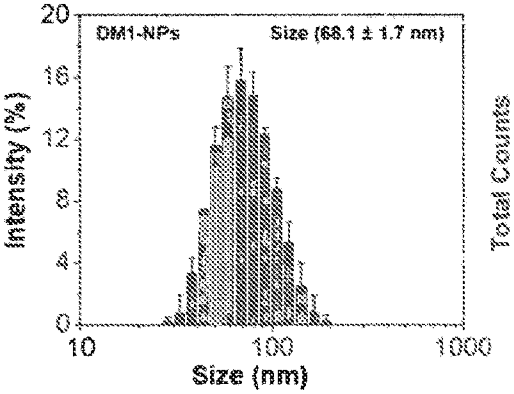
FIG. 1I is a histogram showing the results of DLS analysis of DM1-NPs.
Figure 1J:
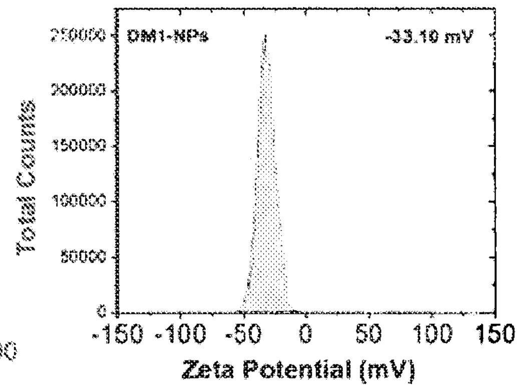
FIG. 1J is a plot showing the zeta potential of DM1-NPs.
Figure 1K:
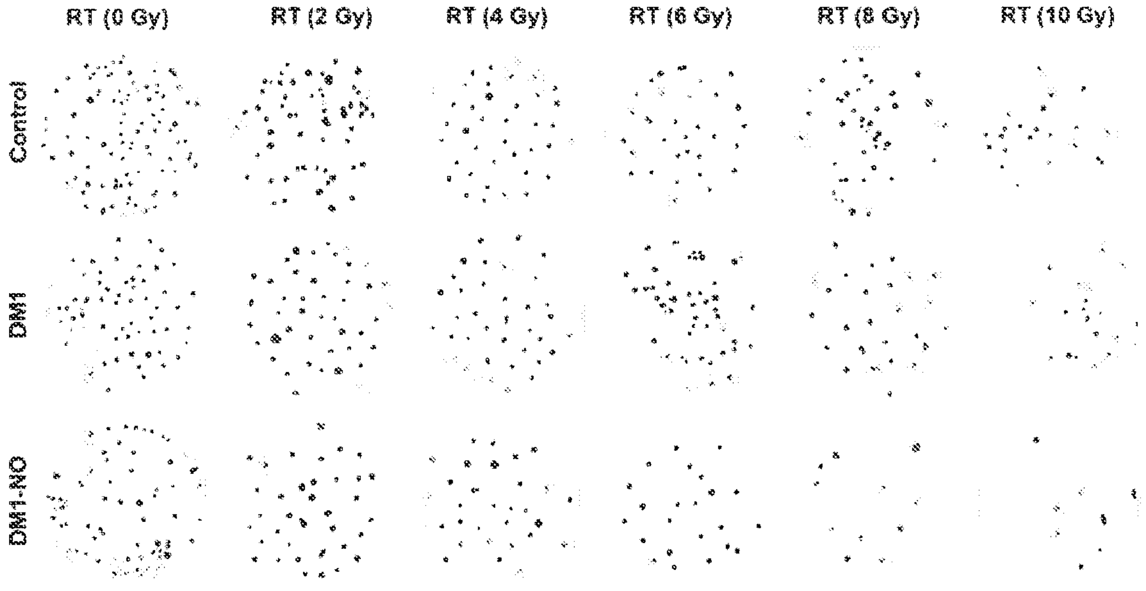
FIG. 1K is a series of representative images of clonogenic assays. H1299 cells were treated with 20 nM of DM1 and DM1-NO for 12 h, followed –X-ray irradiation (6 Gy). The resulting cells were plated for clonogenic assays.
Figure 1L:
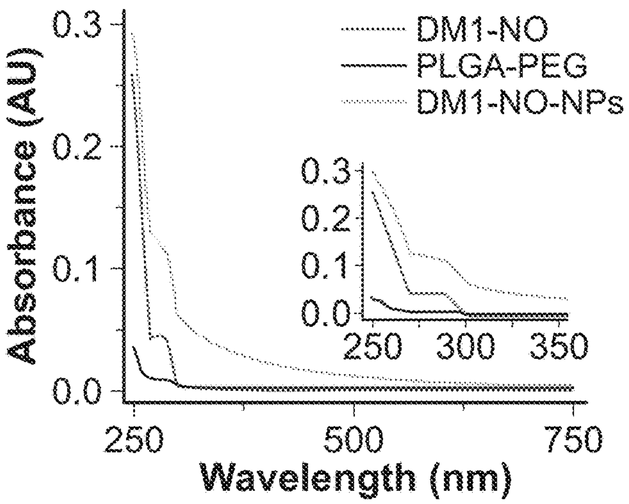
FIG. 1L is a plot showing UV-vis analysis of DM1-NO, PLGA-b-PEG and DM1-NO-NPs.
Figure 1M:
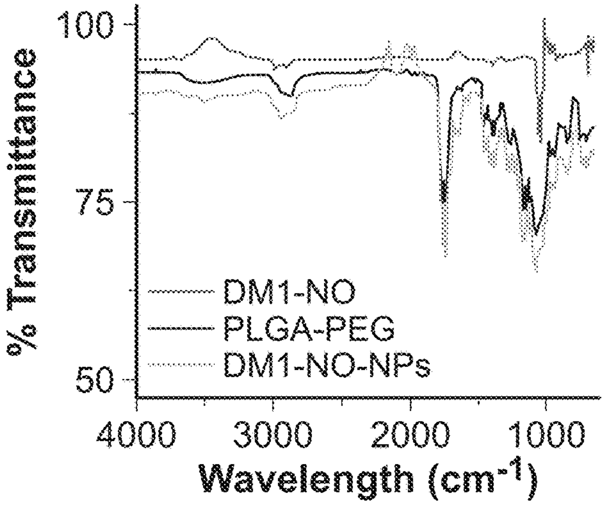
FIG. 1M is a plot showing FT-IR analysis of DM1-NO, PLGA-b-PEG and DM1-NO-NPs.
Figure 1N:
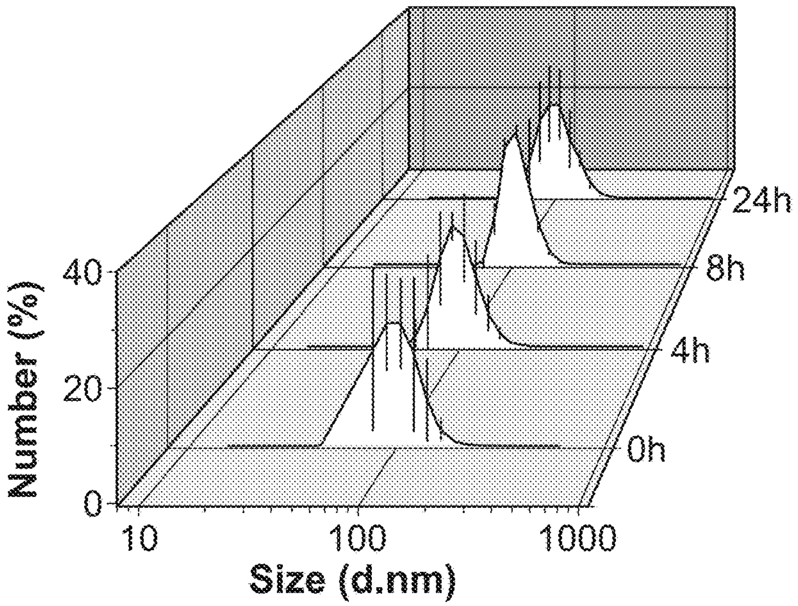
FIG. 1N is a plot showing the results of DLS analysis (hydrodynamic size) over time for DM1-NO-NPs that were incubated in PBS for 24 h.

DM1-NO was loaded onto PLGA-b-PEG nanoparticles through a nanoprecipitation method. The drug loading efficiency and encapsulation efficiency were 3.8% and 43%, respectively. Transmission electron microscope and dynamic light scattering (DLS, FIG. 1D) found that the resulting, DM1-NO PLGA-b-PEG nanoparticles (abbreviated as DM1-NO-NPs onward), have an average size of ~78 nm in water. The polydispersity index or PDI was 0.18±0.01, indicating narrow size distribution and good water dispersibility. DM1-NO-NPs remained stable in PBS without substantial size change over 24 h (FIG. 1N). The nanoparticle surface was negatively charged (zeta potential −29.39 mV, FIG. 1E), which is attributed to the multiple surface hydroxyl groups.

DM1-NO-NPs were loaded onto a dialysis device and compound release was assessed at 37° C. in PBS. Due to hydrophobicity of S-nitrosothiol under physiological conditions, DM1-NO was very slowly released from the nanoparticles at pH 7.4, taking more than 15 h for ~50% of the payload to be liberated (FIG. 1H). The release was significantly accelerated at lower pH. For instance, at pH 6.5, the t½ was reduced to 12 h and at pH 5.5 to 10 h (FIG. 1H).

Example 2: Nitrosylation and Particle Formulation Each Independently Reduce the Toxicity of DM1

Materials and Methods

Cell Culture

H1299 cells were obtained from ATCC (Manassas, Va., USA). Cells were cultured in RPMI-1640 (Gibco, Invitrogen, Carlsbad, Calif., USA) growth medium supplemented with 10% fetal bovine serum (MediaTech, Manassas, Va., USA), 2 mM L-glutamine 100 U/mL penicillin (MediaTech, USA).), and 100 μg/mL streptomycin (MediaTech). Cells were maintained in a humidified atmosphere containing 5% CO2 and temperature was maintained at 37° C.

Measurement of Cells Cytotoxicity (MTT Assay)

The viability of the H1299 cells after different treatments was measured by (4,5-dimethythiazon-2-yl)-2,5-diphenyl tetrazolium bromide (MTT) assay using an Infinite M200 microplate reader (BioTek's Synergy™ Mx, USA). Around $3\times10^3$ cells per well were seeded into a 96-well plate and cultured overnight until the cells fully adhered to the bottom of the plate. The cells were treated with different treatment groups, including free drugs (DM1 and DM1-NO), and drug loaded nanoparticles (DM1-NPs and DM1-NO-NPs) for 72 h. Each treatment group had a final drug concentration of 0.8-500 nM in the growth medium. After that MTT reagent (in 20 μL PBS, 5 mg/mL) was added to each well. The cells were further incubated for 4 h at 37° C. The medium in each well was then removed and replaced by 100 μL DMSO. The plate was gently shake for 5 min (instrument setup) to dissolve the formazan crystals, and the absorbance at 570 nm was recorded by a microplate reader. Each experiment condition was run three times and the data were shown as the mean value plus a standard deviation (±SD).

Results

MTT cell viability assays were performed with H1299 cells, which are a human NSCLC cell line. DM1 was very efficient at suppressing cell proliferation, showing an $IC_{50}$ value of 19.8 nM (FIG. 2A, Table 2).

TABLE 2

Figure 2A:
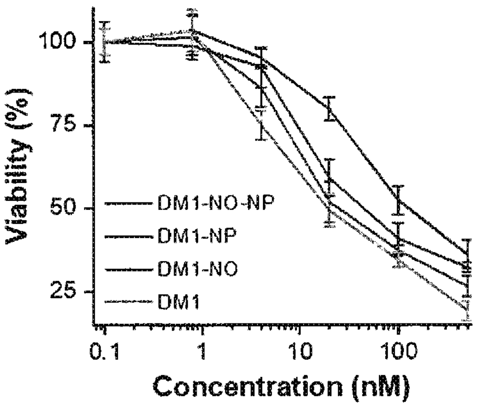
FIG. 2A is a line graph showing cell viability, tested with H1299 cells using MTT assays at 72 h. DM1, DM1-NO, DM1-NPs, and DM1-NO-NPs were studied.

IC50 values of DM1, DM1-NO, DM1-NPs, and DM1-NO-NPs, based on results from FIG. 2A.

| Sample | $IC_{50}$ (nM) (Without RT) |
|---|---|
| DM1 | 19.8 |
| DM1-NO | 25.9 |
| DM1-NP | 52.7 |
| DM1-NO-NP | 98.2 |

As a comparison, DM1-NO-NPs showed an IC50 of 98.2 nM. For comparison, DM1 encapsulated PLGA-b-PEG nanoparticles were prepared (abbreviated as DM1-NPs, FIGS. 1I-1J), and their toxicity accessed. DM1-NO-NPs and DM1-NPs showed reduced toxicity compared to the corresponding free drugs (FIG. 2A, Table 2), which was attributed to controlled drug release. Between DM1-NO-NPs and DM1-NPs, DM1-NO-NPs showed a lower toxicity ($IC_{50}$ 98.2 vs. 52.7 nM, FIG. 2B), which is due to S-nitrosylation of DM1.

Example 3: The Toxicity of Nitrosylated DM1 is Activated by Radiation

Materials and Methods

Clonogenic Assay

Around $3\times10^5$ of H1299 cells were plated in a series of 25 mm petri dishes in 5 mL of complete RMPI-1640 medium, and the cells were incubated for 24 h at 37° C. Once the cells were completely adhered to the bottom of the plate, the media was replaced with fresh RPMI-1640 containing DM1 or DM1-NO with a final concentration of 20 nM. After another 12 h of incubation, the cell cultures were irradiated by X-rays (320 kV) of different doses Immediately following the X-ray irradiation, the cell monolayers were trypsinized using 0.05% Trypsin/EDTA (Gibco, Life Technologies, USA). Single cells were collected and plated onto a 25 mm petri dish in 5 mL complete media (FIG. 1K). Each dish was then incubated for 21 days to allow colonies to form. After that, the media was removed and 0.5% crystal violet in 70% methanol was used to fixed and stain the existing colonies. The plates were sufficiently and carefully rinsed, and were dried at room temperature. Once dried, the colonies were counted manually under a microscope. When observed under the microscope, colonies of 21-50 cells were said to be surviving colonies. The survival rate of these colonies was normalized to the plating efficiency of the untreated control cells. The mean and standard deviation of surviving colonies in each treatment group was calculated.

Detection of ·OH, $^1O_2$ and NO Radicals

Methylene blue (MB) (Sigma-Aldrich, USA) and Singlet Oxygen Sensor Green (SOSG) (Invitrogen, USA) were used to assess ·OH and $^1O_2$ production, respectively. Briefly, 1 mL aqueous solutions of MB (100 μL, 0.5 mM) or SOSG (100 μL, 10 μM) containing different treatment groups (20 nM) were subjected to 6 Gy radiation Immediately after radiation, absorption at 664 nm for MB and fluorescence intensity of SOSG (excitation/emission: 504/525 nm) were measured. Un-irradiated samples and empty NPs were studied as controls.

Superoxide Dismutase (SOD) Assay:

Around $3\times10^4$ cells per well were seeded into each well of a six-well plate and cultured overnight. The cells treated with free drug (DM1 and DM1-NO), and drug loaded nanoparticles (DM1-NPs and DM1-NO-NPs) were given the same concentration of drug (20 nM) and irradiated with 6 Gy of radiation. The plates were then incubated for 24 h. After the treatment, the cells were rinsed with PBS, and the cell pellets were collected using a cell scraper. Cells were homogenized using a sonicator in ice-cold 20 mM 4-(2-hydroxyethyl)-1-piperazineethanesulfonic acid (HEPS) buffer (pH 7.2, containing 1 mM of ethylene glycol-bis(β-aminoethyl ether)-N,N,N',N'-tetraacetic acid, also known as EGTA; Millipore Sigma, USA), 210 mL of mannitol, and 70 mM sucrose. Following homogenization, a pellet was formed by centrifugation at 15,000×g for 15 minutes at 4° C. The supernatant was collected, and an assay was immediately performed to assess cytosolic SOD levels by comparing to a standard curve. To measure mitochondrial SOD levels, the pellet was resuspended in ice-cold PBS, and the sample was measured accordingly.

Lipid Peroxidation Assay:

BOBIPY 581/591 probe (ThermoFisher Scientific, USA) was used to measure lipid peroxidation levels. Briefly, H1299 cells were incubated with DM1-NO-NPs (20 nM) for 12 h*** (time). After replenishing the incubation medium, X-ray (6 Gy) was applied. For controls, cells incubated with PBS, DM1, DM1-NO and DM1-NPs, or not receiving radiation were studied. The BOBIPY 581/591 probe (10 μM) was added to the cells and incubated for 30 min and ice-cooled PBS was used to wash the cells. After that, both red (590 nm) and green (510 nm) emission were recorded and the ratios computed (the phenylbutadiene experiences a fluorescent shift from red to green upon oxidation).

Peroxynitrite:

Peroxynitrite levels were measured by Peroxynitrite Green Sensor (AAT Bioquest, Sunnyvale, Calif., USA), which upon reaction with peroxynitrites produces a green florescence compound. Briefly, around 5×103 cells were seeded in a costar black wall/clear, bottom 96-well plate (corning, ME-USA), and incubated with 20 nM of free drug (DM1 and DM1-NO) or drug loaded nanoparticles (DM1-NPs and DM1-NO-NPs) for 6 h before being irradiated with X-ray at 6 Gy. After that, 10 μL of the Peroxynitrite Green Sensor solution was added to each well and incubated with cells for 1 hour. Fluorescence signals were measured on a microplate reader using the FITC filter: (490 nm excitation, 530 nm emission, and 515 nm cutoff). For confocal microscopic imaging, cells were seeded in CLSM-special dish and similar treatment as above-mentioned were used. Images were taken on a Zeiss LSM 710 system using the FITC filter.

Intracellular ROS/NO Measurement:

H1299 cells ($2\times10^4$ cells) were seeded onto Nunc Lab Tek Chamber Slides (ThermoFisher Scientific, USA) and incubated with 20 nM of free drug (DM1 and DM1-NO) or drug loaded nanoparticles (DM1-NPs and DM1-NO-NPs) for 12 h. The cells were then irradiated by X-ray (6 Gy). Serum-free RPMI-1640 medium containing (100 μL, 5 μM) 4-Amino-5-Methylamino-2',7'-Difluorofluorescein Diacetate (DAF-FM, ThermoFisher Scientific, USA) and Ethidium Homodimer III (100 μL, 10 μM) (EthD-III, Biotium, USA, Cat. #s 40050) was added to each well and allowed to further incubate for 30-35 min. The NO released from the drug would then react with DAF-FM to produce green fluorescence. Meanwhile, EthD-III, a DNA dye that is impermeable to an intact plasma membrane, translocates dead cells and binds to the nucleus DNA to give out red fluorescence. To remove free dye molecules, the cells were washed with serum-free medium three times and imaged under a confocal laser microscope (Zeiss, LSM 710, USA) with the following setup. DAF-FM (FITC), ex/em: nm; EthD-III (Rhodomine (red)), ex/em.

γ-H2AX Assay:

$3\times10^4$ cells were seeded into each well and cultured overnight and further incubated with 20 nM of free drugs (DM1 and DM1-NO) or drug loaded nanoparticles (DM1-NPs and DM1-NO-NPs) for 12 h. The cells then received 6-Gy irradiation and were incubated for another hour. Then the cells were fixed in ice cold 50% $CH_3OH$ and 50% $(CH_3)_2CO$ for 20 min After fixation, cells were permeabilized with 0.5% Triton-X-100 in PBS (1×) and then blocked with 0.2% skimmed milk (Difco™ Skim Milk, BD, VWR, USA), 0.1% TritonX-100 (Millipore, Sigma USA), and 5% Goat Serum (Normal Goat Serum, ab7481) in PBS. Then cells were stained with the Anti-phospho H2A.X (Ser139) Antibody, conjugate anti-γ-H2AX antibody AlexaFluor-647 (Millipore, Sigma USA USA) for detection of phospho-Histone H2A.X. Cells were wash 3 times with ice cold PBS (1×) and coverslips were mounted using mounting medium containing DAPI (Fluoro-Gel II with Dapi, Electron MicroscopyMSciences, USA) to counterstain cellular nuclei. γ-H2AX foci were counted by Image-J. The average number of foci per cell was calculated from a minimum of 50 cells per sample. Experimental data represent the average of three independent experiments.

In Vitro Cells Cycles Arrest:

H1299 cells were seeded onto 6-well plates at a density of $2\times10^5$ cells per well and cultured overnight. The cells were then incubated with 20 nM of free drugs (DM1 and DM1-NO) or drug loaded nanoparticles (DM1-NPs and DM1-NO-NPs) for 24 h, and were then harvested and washed with ice-cold phosphate-buffered saline (PBS) and fixed with cold 70% (vol/vol) ethanol overnight at 4° C. The resulting cells were resuspended in PBS (1×) buffer containing a final concentration of 20 μg/mL RNase A and 20 μg/mL propidium iodide (eBioscience, Invitrogen, USA) for 15 min. The cell cycle profiles were determined using flow cytometry (HyperCyAn, Beckman USA) and analyzed using CellQuest software.

Tubulin Inhibition Assay:

The assay was performed according to the manufacturer's protocol (PurSolutions, USA). In brief, β-tubulin proteins (>97% pure) were suspended in G-PEM buffer (pH 6.9, containing 80 mM PIPES, 2 mM $MgCl_2$, 0.5 mM EDTA, and 1.0 mM GTP) to a final concentration of 1.0 mg/mL. The tubulin solution was then incubated with G-PEM buffer alone (control), and free drugs (DM1 and DM1-NO) or drug loaded nanoparticles (DM1-NPs and DM1-NO-NPs). The drug concentration range was 0-20 μmol/L and the incubation took 45 min at 30° C. For sedimentation assays, the polymers formed were centrifuged (35000×g, 1 h, 30° C.), and the pellets were further depolymerized in 1 mmol/L GTP in PEM buffer at 0° C. overnight and the protein concentrations were determined. The sedimentation assay for each compound was performed at least twice. For TEM analysis, the samples were fixed in 0.2% glutaraldehyde (Millipore sigma, USA) and stained with 0.5% uranyl acetate (Millipore sigma, USA) to observe tubule morphology. The images were acquired on a transmission electron microscope (Hitachi HT7800) TEM) operated at 120 KV.

Results

The potential of DM1-NO as a radiosensitizer was assessed by clonogenic assays. Briefly, DM1 or DM1-NO was incubated with H1299 cells, the cells were irradiated with X-rays (0-10 Gy), and the resulting cells were seeded onto a petri dish (FIG. 1K). Colonies consisting more than 50 cells after 3 weeks were counted, and the data fit to a linear-quadratic model (Table 3).

Figure 2B:
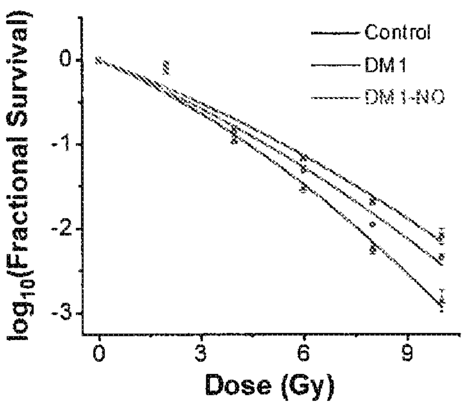
FIG. 2B is a line graph showing clonogenic assay results, tested with H1299 cells. DM1+RT, DM1-NO+RT, and RT alone were tested. The results were fit into the linear-quadratic (LQ) model.

TABLE 3

α, β, and $D_{10}$ values, based on fitting results from FIG. 2B. Linear Quadratic Model

| Best fit Value | α | β | $D_{10}$ |
|---|---|---|---|
| Control | 0.0649 | 0.0029 | 5.40 |
| DM1 | 0.0729 | 0.0033 | 4.89 |
| DM1-NO | 0.0765 | 0.0051 | 4.39 |

DM1 shows a D10 (radiation dose at 10% fractional survival) of 4.89 Gy, compared to that of 5.40 Gy for RT alone (Table 3). DM1-NO has an even lower D10 of 4.39 Gy, and a dose modifying factor at 10% factional survival (DMF10) of 1.23. The fact that DM1-NO shows lower toxicity than DM1 but higher dose modifying effects supports the hypothesis that DM1-NO under radiation releases DM1 and NO which collectively sensitize cancer cells to RT. The MTT results also confirmed the enhanced radiosensitizing effects of DM1-NO and DM1-NO-NPs relative to DM1 (FIG. 2A, Table 2, FIG. 7H, Table 4).

TABLE 4

Figure 7A:
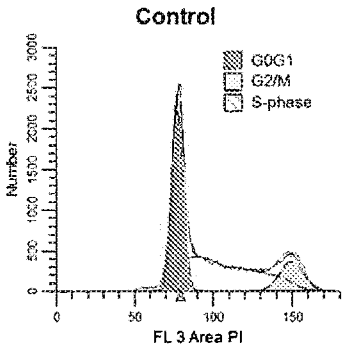
FIGS. 7A-7E are plots showing the results of a cell cycle analysis, based on PI staining and assessed by flow cytometry. H1299 cells were incubated with PBS (7A), DM1 (7B), DM1-NO (7C), DM1-NPs (7D), or DM1-NO-NPs (20 nM, DM1 concentration) (7E) before analysis.
Figure 7B:
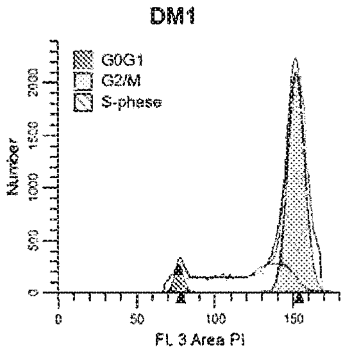
Figure 7C:
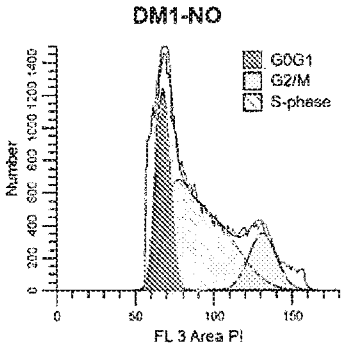
Figure 7D:
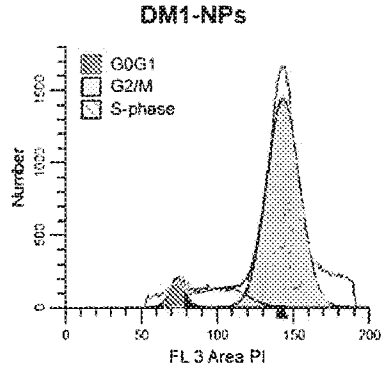
Figure 7E:
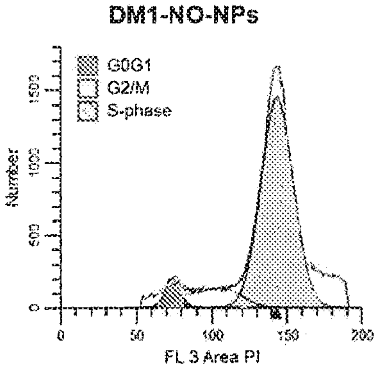
Figure 7F:
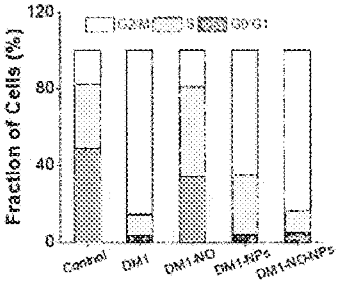
FIG. 7F is a bar graph showing fractions of cells at S, G0/G1, or G2/M phases, based on analysis results described in FIGS. 7A-7E. *P<0.05; P<0.01; *P<0.001; ns, no significant difference.
Figure 7G:
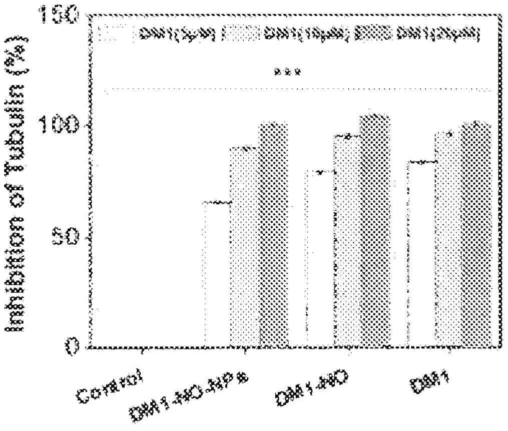
FIG. 7G is a bar graphs showing Percentage of tubulin inhibition. Tubulin polymer was collected by centrifugation (35000×g for 1 h at 30° C.) and the amount of tubulin protein sediment was quantified by measuring protein concentration. ***, P<0.001.
Figure 7H:
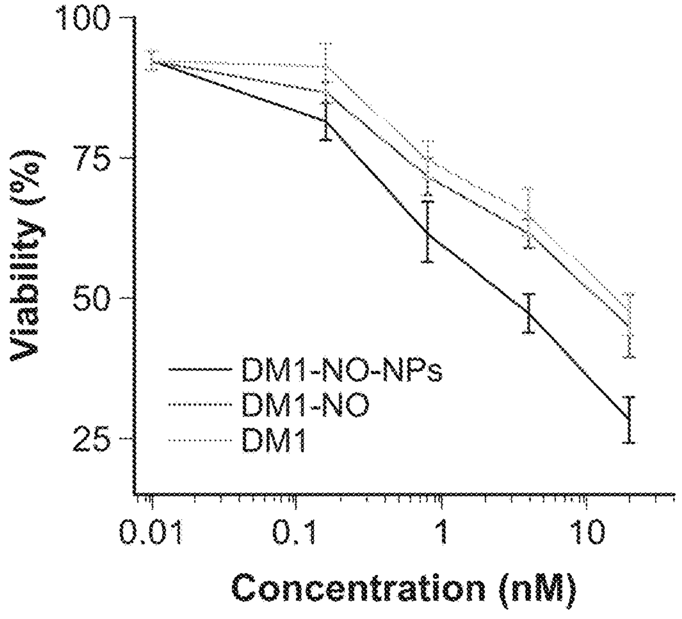
FIG. 7H is a line graph showing cell viability, tested with H1299 cells using 72-h MTT in the presence of RT. DM1, DM1-NO, and DM1-NO-NPs were studied.

$IC_{50}$ values for viability data presented in FIG. 7H.

| Sample | $IC_{50}$ (nM) (With RT) |
|---|---|
| DM-1 | 17.4 |
| DM1-NO | 14.9 |
| DM1-NO-NPs | 3.3 |

Figures 3A, 3B, 3C, 3D:
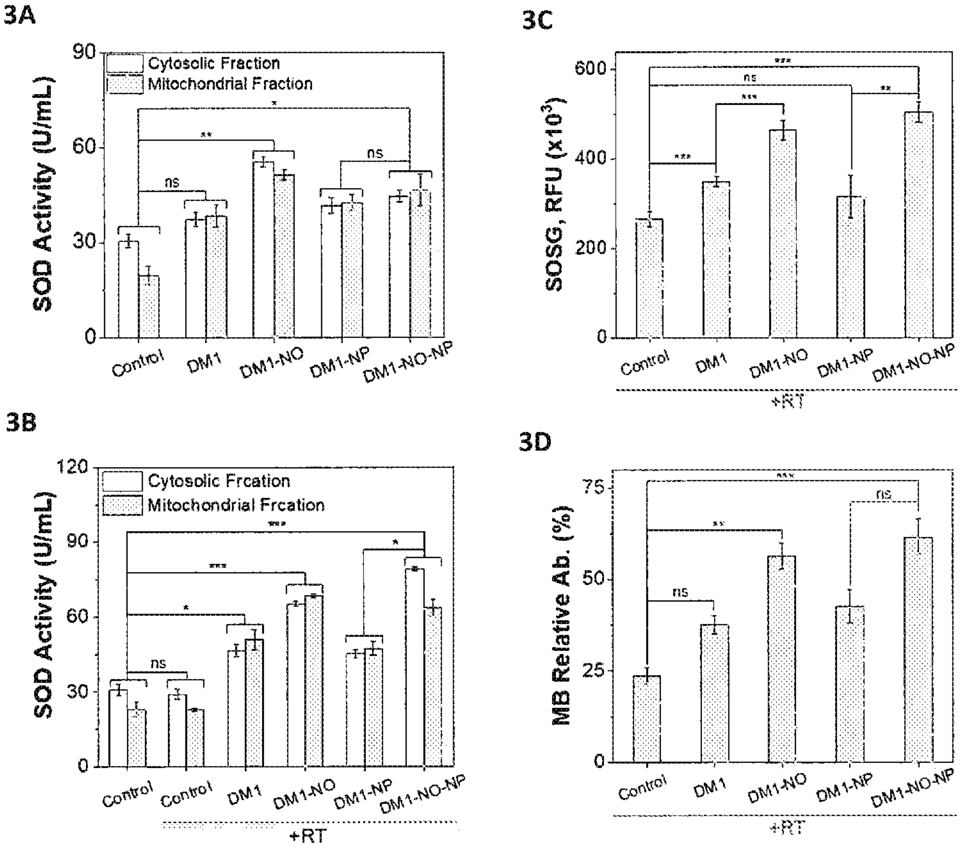
FIGS. 3A-3D are bar graphs showing the impact on intracellular oxidative stress. The studies were performed with H1299 cells that had been incubated with DM1, DM1-NO, DM1-NPs, DM1-NO-NPs, or PBS.

To better understand the radiosensitizing effects, intracellular oxidative stress after RT was assessed. Cytosol and mitochondrial superoxide dismutase (SOD) levels were increased when cells were incubated with DM1-NO, and were further elevated when radiation (6 Gy) was applied (FIG. 3A-3B). For instance, compared to DM1+RT, DM1-NO+RT treatment increased the cytosol SOD activity by 70.08% and mitochondrial SOD activity by 24.36%. A similar level of SOD elevation was observed with DM1-NO-NPs (FIG. 3A). The intracellular $^1O_2$ and OH levels were also measured using Singlet Oxygen Sensor Green (SOSG) and methylene blue (MB) staining, respectively. Both SOSG fluorescence activity (FIG. 3C) and MB bleaching (FIG. 3D, manifested as absolute value changes) were significantly elevated with DM1-NO-NPs+RT, again confirming an increased oxidative stress (Ewing, *Radiat. Res.* 94, 171-189 (1983), Riley, *Int. J. Radiat. Biol.* 65, 27-33 (1994)).

Figure 4A:
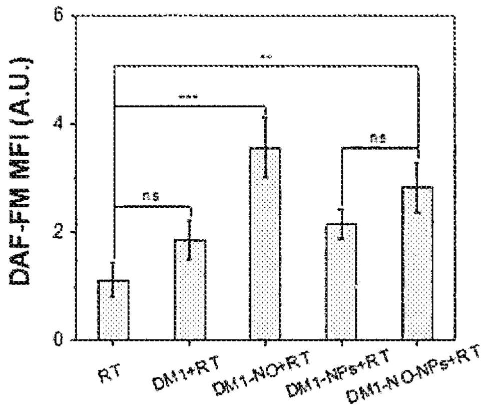
FIG. 4A is a bar graph showing median fluorescence intensity (MFI) of DAF-FM. H1299 cells were incubated with 20 nM DM1, DM1-NO, DM1-NPs, DM1-NO-NPs, or PBS for 12 h and then received 6 Gy irradiation. Cells were stained with DAF-FM (for NO) and Eth-III (for cells with breached membrane) and imaged by confocal microscopy.
Figure 4B:
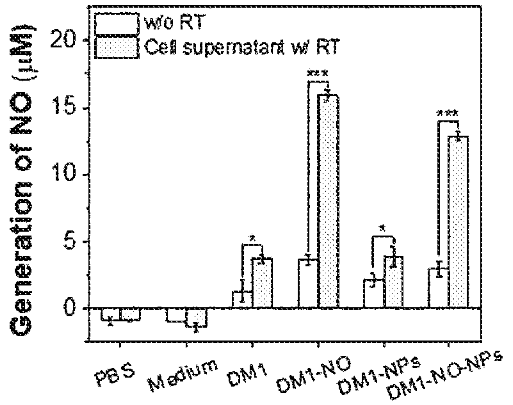
FIG. 4B is a bar graph showing intracellular NO levels, measured by Greiss assays. H1299 cells were incubated with DM1, DM1-NO, DM1-NPs, DM1-NO-NPs, or PBS and then either received 6 Gy irradiation (w/RT) or not (w/o RT).
Figure 5A:
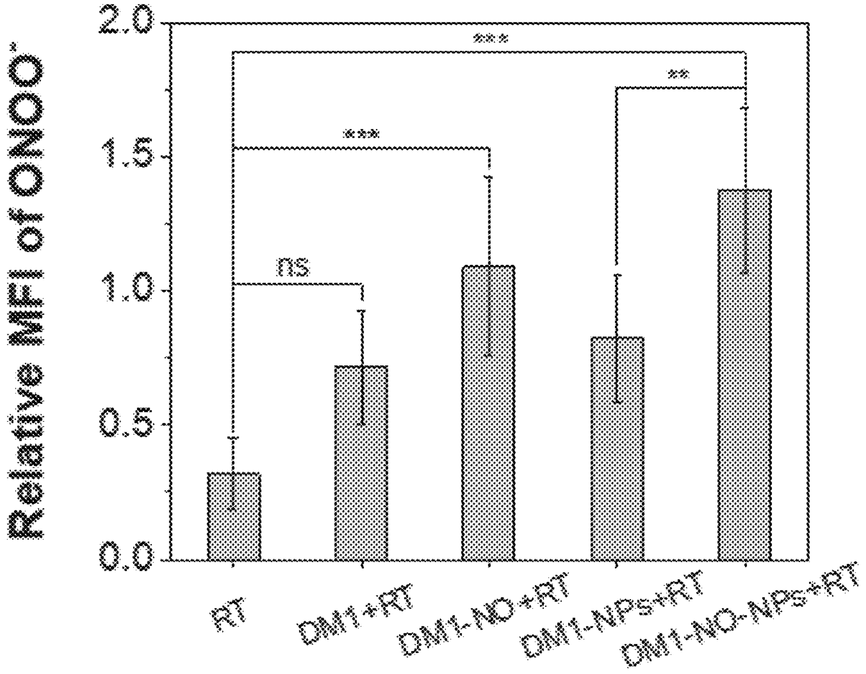
FIG. 5A is a bar graph showing relative increase of MFI compared to the control. H1299 cells were incubated with 20 nM DM1, DM1-NO, DM1-NPs, DM1-NO-NPs, or PBS for 6 h and then received 6 Gy irradiation. Peroxynitrite Sensor Green staining was performed to measure ONOO— in cells. For control, cells received neither drug incubation nor irradiation. Cells were imaged by confocal microscopy.
Figure 5B:
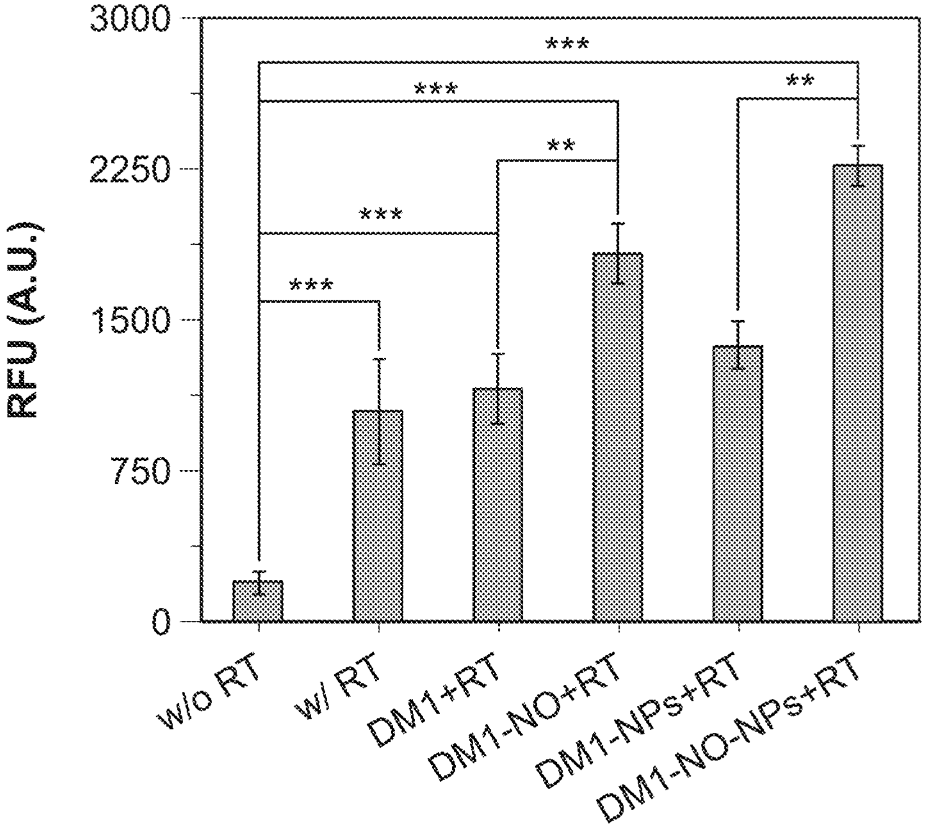
FIG. 5B is a bar graph showing relative fluorescence units (RFU). H1299 cells received the same treatments as described in FIG. 5A, and the fluorescence activity was measured on a microreader instead of under a confocal microscope. * P<0.05; P<0.01; *P<0.001; ns, no significant difference.

Intracellular NO level changes were assessed using DAF-FM, a fluorometric sensor of NO. Confocal fluorescence microscopy found higher levels of positive DAF-FM staining with DM1-NO-NPs+RT than with DM1-NPs+RT. Relative to un-irradiated cells, the fluorescence intensity was increased by 2.52-fold for DM1-NO-NPs+RT and 1.66-fold for DM1-NPs+RT, respectively (FIG. 4A). Similar results were observed with Griess assays, which found a 4.36-fold increase of NO release for DM1-NO-NPs+RT, and a 1.83-fold increase for DM1-NPs+RT (FIG. 4B). Free NO would react with intracellular ROS to form reactive nitrogen species (RNS) such as peroxynitrites (Pacher et al., *Physiol. Rev.* 87, 315-424 (2007)) which are highly toxic (Fraszczak et al., *J. Immunol.* 184, 1876-1884 (2010), Korkmaz et al., *Interdiscip. Toxicol.* 2, 219-228 (2009)). Indeed, Peroxynitrite Sensor Green staining found that the intracellular peroxynitrite level was significantly elevated with DM1-NO-NPs+RT (FIG. 5A). Fluorometric analysis revealed a 2.17-fold increase of Peroxynitrite Sensor Green activity with DM1-NO-NPs+RT than with RT alone (FIG. 5B).

Figure 4C:
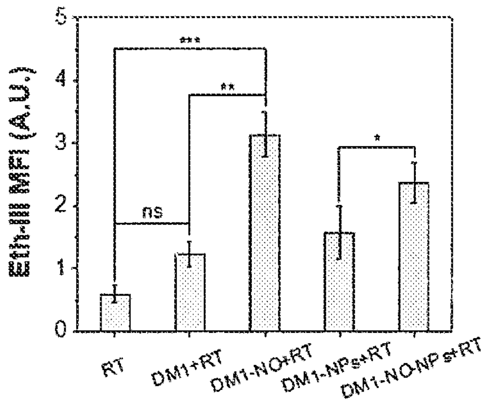
FIG. 4C is a bar graph showing MFI of Eth-III based on imaging results from the assay described in FIG. 4A. *P<0.05; P<0.01; *P<0.001; ns, no significant difference.
Figure 6A:
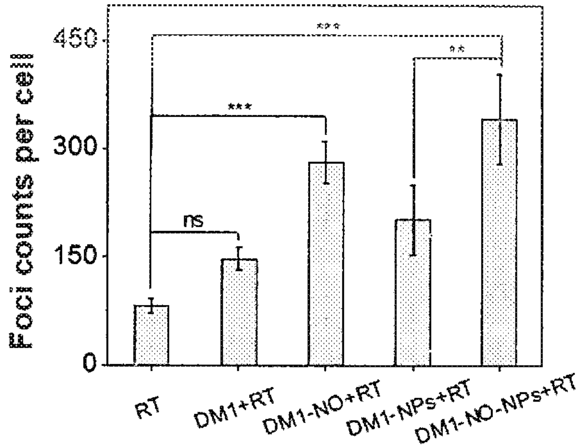
FIG. 6A is a bar graph showing foci numbers per cell. Anti-γH2AX staining, performed 12 h after H1299 cells were treated with 20 nM DM1-NO-NPs plus 6 Gy irradiation (DM1-NO-NPs+RT). DM1-NPs+RT, DM1-NO+RT, DM1+RT, RT alone, and un-treated cells were investigated for comparison. Cells were imaged, and analysis was performed by Image-J.
Figure 6B:
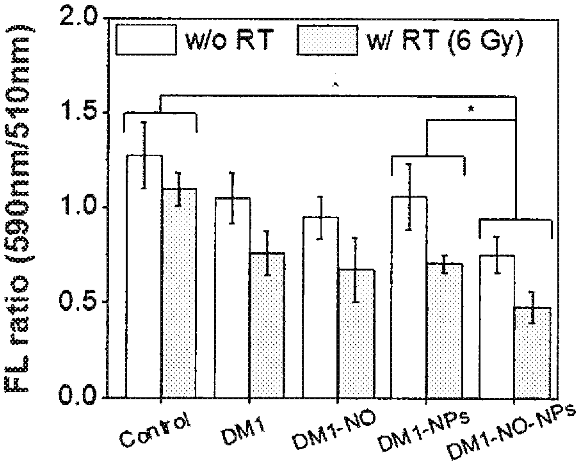
FIG. 6B is a bar graph showing lipid peroxidation levels, assessed using BOBIPY lipid assay by measuring red/green (590/510 nm) fluorescence ratio. H1299 cells were treated with 20 nM DM1-NO-NPs for 12 h, with and without 6 Gy irradiation (DM1-NO-NPs+RT). DM1-NPs+RT, DM1-NO+RT, DM1+RT, RT alone, and untreated cells were investigated for comparison. *, P<0.05; P<0.01; *P<0.001; ns, no significant difference.

The elevated ROS and RNS levels caused extensive damage to intracellular components. γH2AX staining found more positive staining with DM1-NO-NPs+RT, with foci numbers increased by 4.14 times relative to RT alone (FIG. 6A). BODIPY Lipid Probe assay found that the 581/591 nm ratio was decreased by 56.47%, indicating significantly enhanced lipid peroxidation (FIG. 6B). Notably, DNA and lipid damage was much more significant with DM1-NO-NPs+RT than with DM1-NPs+RT, underscoring the role of NO and its RNS derivatives in the treatment. These results also agree well with MTT (FIG. 2A, Tables 2-3) and Eth III staining results (FIG. 4C), confirming that an elevated oxidative stress, much of it attributable to NO released from DM1-NO, was behind the radiosensitizing effects.

On the other front, DM1 released from DM1-NO-NPs would interfere with tubulin polymerization (Lopus et al., *Mol. Cancer Ther.* 9, 2689-99 (2010), Bhattacharyya & Wolff, *FEBS Lett.* 75, 159-162 (1977)). This was studied by incubating β-tubule (1 mg/mL) in the presence of DM1, DM1-NO, DM1-NO-NPs, or PBS for 1 h, and then examining fiber formation by TEM. In the absence of drugs, β-tubule self-assembled into long fibers. As a comparison, all the DM1 containing compounds or nanoparticles efficiently inhibited fiber formation. Notably at high concentrations (e.g. 20 μM DM1), β-tubulin started to form aggregations due to non-specific interaction among β-tubule molecules (Bhattacharyya & Wolff, *FEBS Lett.* 75, 159-162 (1977)). Tubule polymerization was quantitatively assessed by sedimentation (FIG. 7G). Compared to the PBS control, DM1-NO-NPs suppressed polymer formation by 65.7%, 90.6%, and 99.7%, respectively, at 5, 10, and 20 μM (DM1 concentration).

Microtubule formation is an essential step in cell mitosis. Inhibiting the process would enrich cells at the G2/M phase (Ng et al., *Cancer Res.* 60, 5451-5455 (2000)). This was analyzed by flow cytometry using propidium iodide (PI) cell staining (FIG. 7A-7E). When H1299 cells were incubated with DM1, the portion of cells in the G2/M phase was drastically increased from 17.5% to 85.3% (FIG. 7F). A similar level of G2/M arrest (83.47%) was observed with DM1-NO-NPs. The mitosis arrest is believed to also contribute to the dose modifying effects of DM1-NO-NPs.

Example 4: Particle Formulated-Nitrosylated DM1 Accumulates in Tumors and Kills Cancer Cells in Response to Radiation

Materials and Methods

Tumor Model Establishment and Therapy Studies

All animal experiments were performed according to protocols approved by the Institutional Animal Care and Use Committee (IACUC). Female athymic nude mice (Charles River Laboratories, USA) at 6 weeks old were housed in a protected unit specified for immunodeficient animals. To establish tumor models, H1299 cells ($2\times10^5$ cells) were suspend in a matrigel solution and were subcutaneously injected into mice using a 28-gauge needle. All mice were randomized into six groups (n=5). When the average tumor volume reached 150 mm3, 200 μL free drug (DM1, DM1-NO) or drug loaded NPs (DM1-NPs, DM1-NO-NPs) in PBS at a dose of 260.8 nmol/kg were injected intravenously into the mice. Mice treated with 200 μL PBS were studied as a control. All the other mice received X-ray irradiation (6 Gy, 320 kV) to tumors 4 h after drug/nanoparticle injection, with the rest of the body shielded by lead. Tumor size and body weight were inspected every 3 days using a digital caliper, and the tumor volume was estimated as (length)×(width)2/2. After 24 days, the mice were euthanized, and the tumor was excised and dissected into slices for hematoxylin and eosin (H&E) staining.

Toxicity Study (AST/ALT):

Six-week old female albino BALB/c mice were purchased from Charles River Laboratories, USA. The animals were divided into control and experimental groups (n=3) and marked to permit individual identification. A similar dose (260.8 nmol/kg) of DM1-NO-NPs as used in therapeutic study was administered intravenously and the mice were examined for 10 days to observations for abnormal sign of toxicity such as change in behavioral, dizziness, respiratory distress or mortality were conducted until the end of the study. To further evaluate the hepatic function, alanine aminotransferase (ALT) and aspartate aminotransferase (AST) activities were measured and blood chemistry analysis was performed by using 20 μL blood serum sample form each treated animal to assess the following: white blood cells (WBC), red blood cells (RBC), and platelets (PLT), plateletcrit, (PCT, mean platelet volume or platelet distribution width) and also corresponding sets of electrolytes (sodium, potassium, chloride, bicarbonate, sugar (glucose) calcium, inorganic phosphate, and magnesium, lipids (cholesterol), albumin, and total protein levels were also analyzed.

Histological Analysis:

The gross pathological changes in main organs (including the brain, heart, lungs liver, kidney spleen) were harvested and immediately transferred in fixation solution (10% buffered formalin) and embedding in paraffin for further histopathological evaluation. Sections with thickness of about 5 μm were prepared, stained with hematoxylin and eosin (H&E), and examined for histopathological changes using microscope with varying magnification and objective lens.

Statistical Analysis:

The means and standard errors were calculated from at least three repeated groups in all the experiments. Statistical significance between groups was determined with the Student's t-test where $P<0.05$ was considered to statistically signify difference between two groups.

Results

Figure 8A:
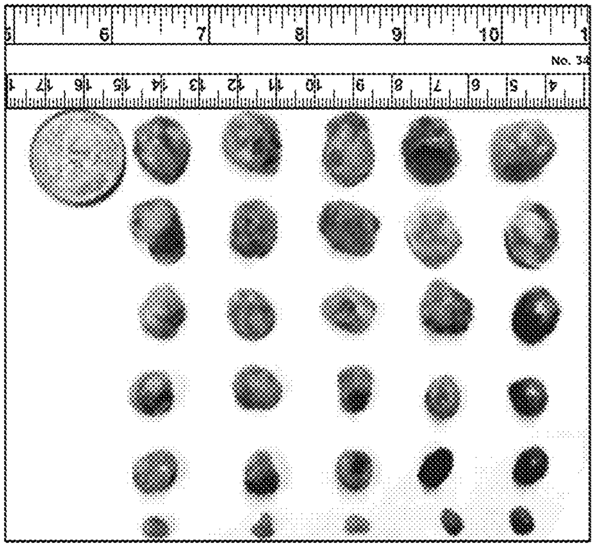
FIGS. 8A-8D show the results of therapy studies, performed on H1299 tumor bearing nude mice. The animals received i.v. injection of PBS, DM1, DM1-NO, DM1-NPs, or DM1-NO-NPs and then X-ray irradiation (6 Gy) after 4 h (n=5). Animals receiving PBS injection only was studied as a control.
Figure 8B:
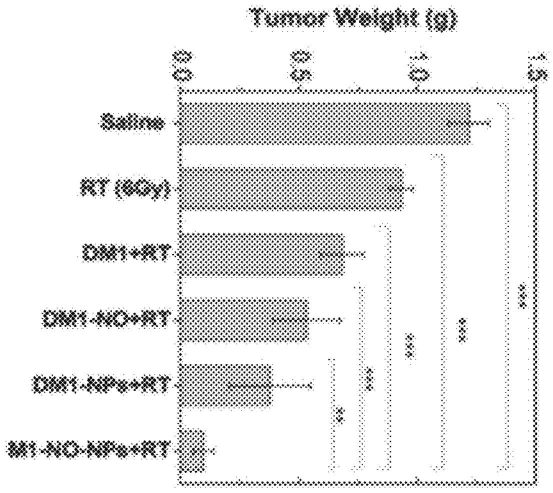
Figure 8C:
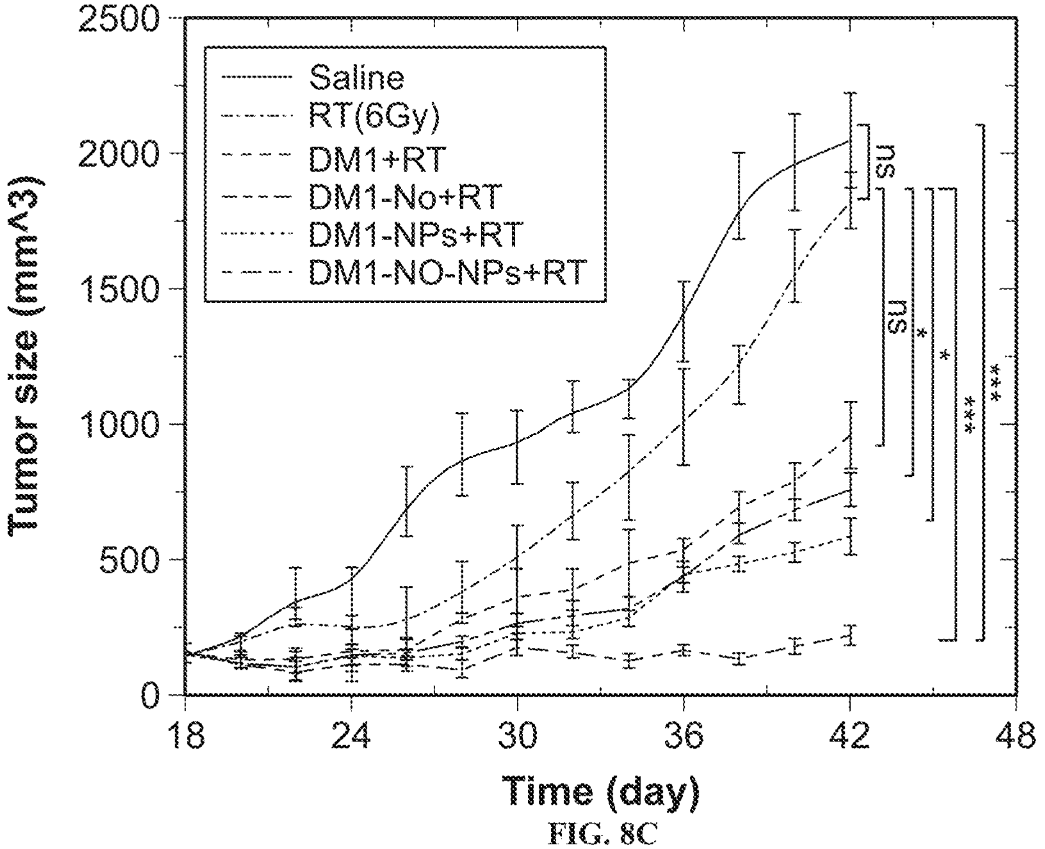
Figure 8D:
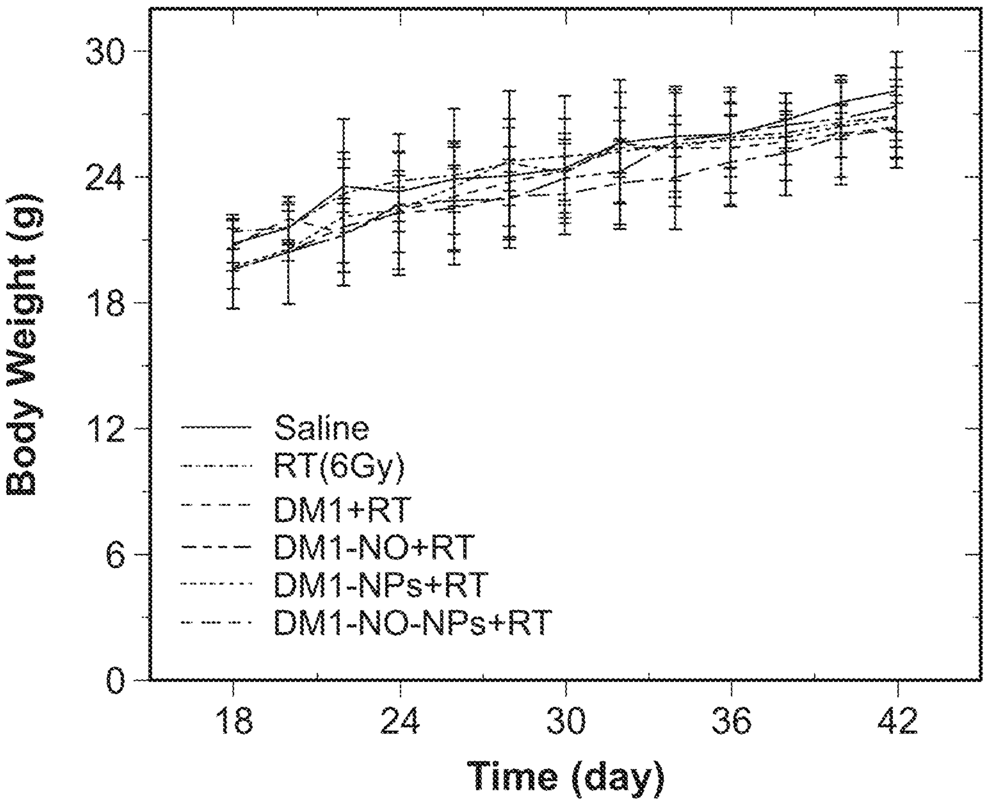

In vivo therapy studies were performed with H1299 tumor bearing nude mice. When tumor size reached 150 mm3, DM1-NO-NPs (260.8 nmol/kg, equivalent to 0.2 mg DM1/kg) was intravenously (i.v.) injected into the animals (n=5). X-ray radiation (6 Gy) was applied to tumors, with the other parts of the animal body lead-shielded. Single radiation at similar doses are commonly used in pre-clinical small animal studies (Biglin et al., *Radiat. Oncol.* 14, 134 (2019)). For comparison, DM1, DM1-NO, and DM1-NPs at the same DM1 concentration, as well as PBS, were also tested. All the animals were euthanized after 24 days and their tumors and major organs were harvested. DM1-NO-NPs+RT showed the most effective tumor suppression among all treatment groups (FIG. 8A-8C). On Day 24, the average tumor size was 219.4 mm3 and weight was 0.096 g. As a comparison, the tumor size and weight were 1826.4 mm3, and 0.931 g, respectively, for the RT only group. This represents a 9.64-fold enhancement in tumor inhibition rate (TIR) for DM1-NO-NPs+RT relative to RT alone (FIG. 8B, 8C). Notably, the tumor inhibition of DM1-NO-NPs+RT was also much greater than DM1-NO+RT and DM1-NPs+RT (Day 24 tumor volumes were 759.33 and 589.03 mm3, respectively; FIG. 8B). This indicates that both nanoparticle drug delivery and NO release have contributed to the superior radiosensitizing effects of DM1-NO-NPs+RT. Meanwhile, there was no significant body weight drop (FIG. 8D) nor signs of toxicity for DM1-NO-NPs+RT treated animals, indicating good tolerance. The harvested tumor and major organ samples were blindly examined by a pathologist. For the PBS control, the tumor had about 50% coagulative necrosis with very few TUNEL positive cells at the periphery of these foci of necrosis. The remaining tumor cells were large and appeared viable with many well-defined mitotic figures. For animals in the RT group, there was more coagulative necrosis (about 70%) while the remaining tumor cells had degenerative changes (rounded up, shrunken, increased cytoplasmic eosinophilia). Compared to the other groups, tumors in the DM1-NO-NPs+RT group had more positive TUNEL staining, indicating increased treatment efficacy. In all the treatment groups, no signs of toxicity were found in normal tissues such as the brain, lung and kidneys.

Figure 9A:
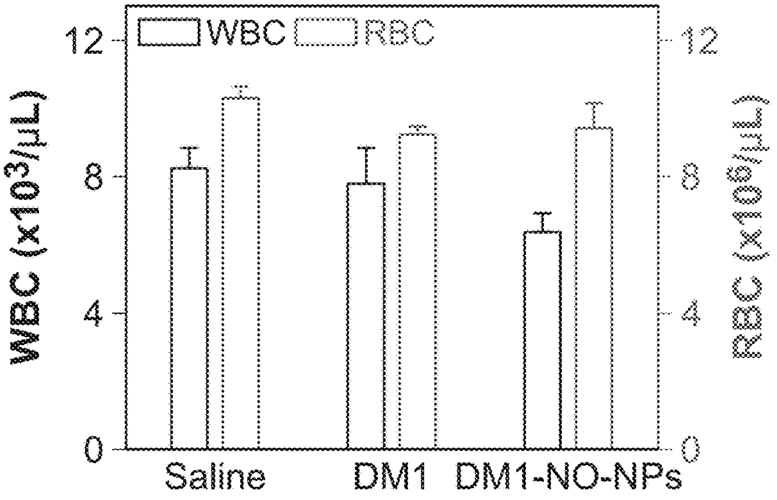
FIGS. 9A-9C show the results of hematological analysis for toxicity assessment. Blood was taken from balb/c mice receiving i.v. injection of 260.8 nmol/kg (equivalent to dose used in therapy studies) DM1-NO-NPs or DM1, or PBS on Day 10 (n=3).
Figure 9B:
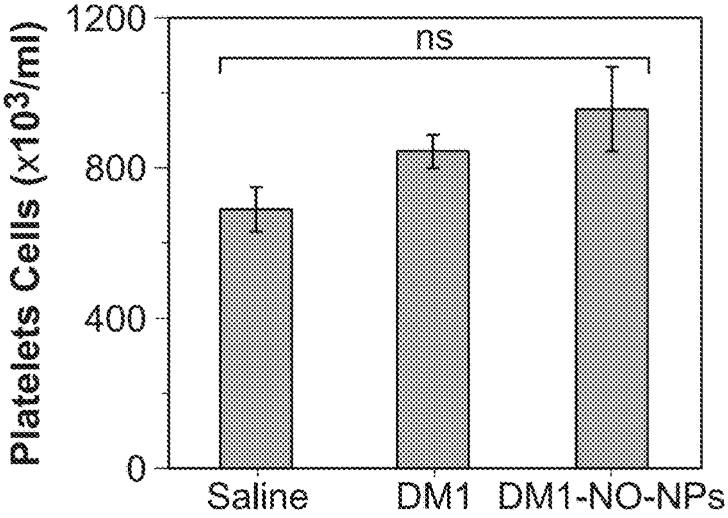
Figure 9C:
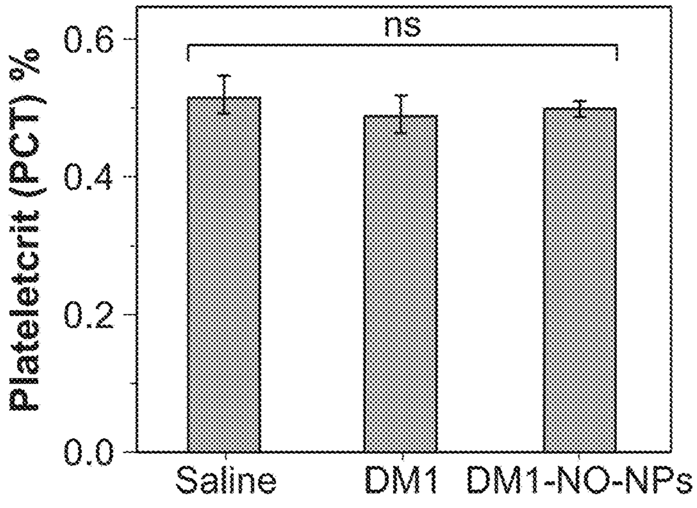
Figures 10A, 10B, 10C, 10D, 10E, 10F, 10G:
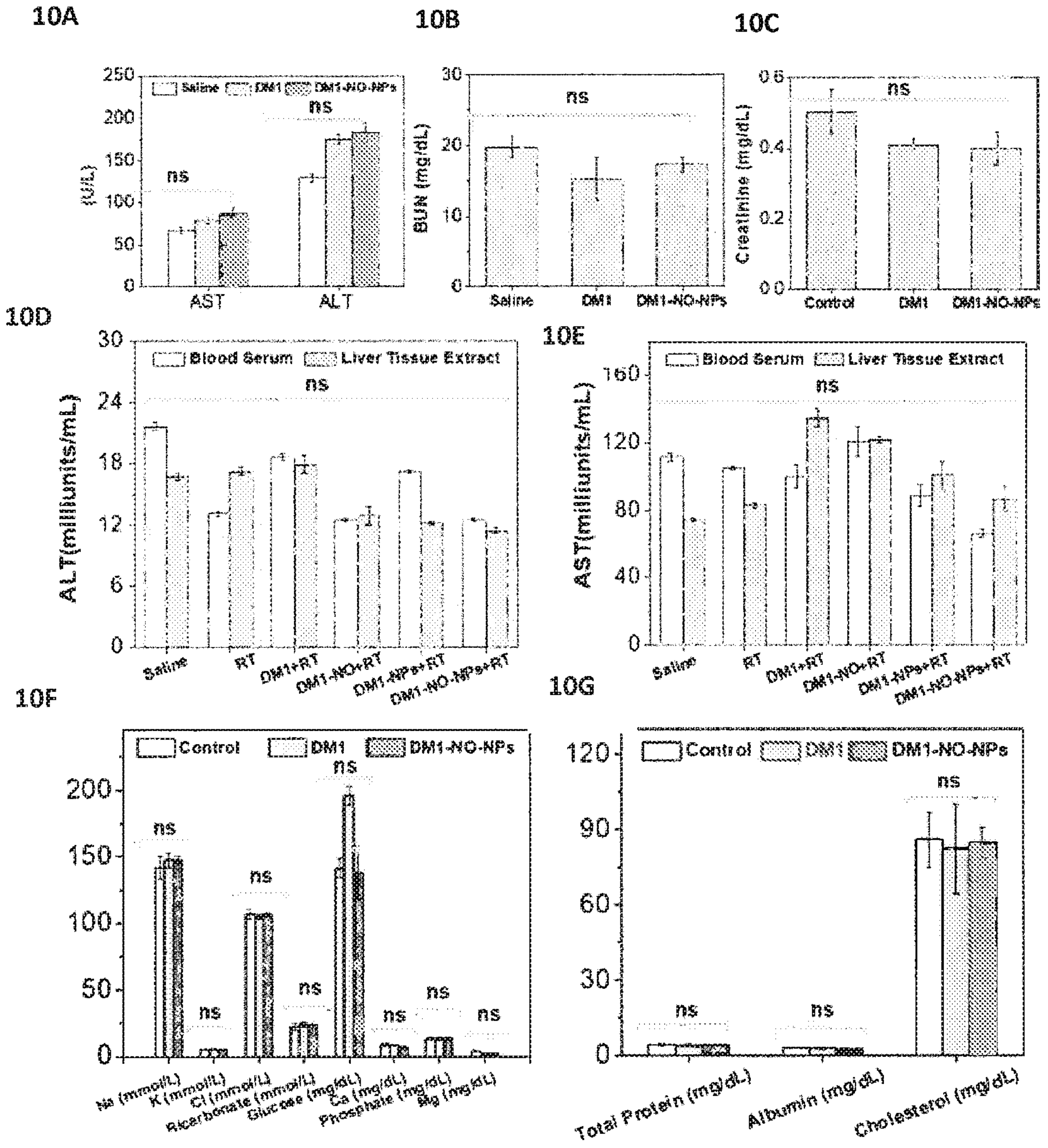
FIGS. 10A-10G show the results of in vivo toxicity studies. Blood or tissue samples were taken from balb/c mice receiving i.v. injection of 206.8 nmol/kg (equivalent DM1 dose) DM1-NO-NPs or DM1, or PBS on Day 10 (n=3).

To better understand the potential adverse effects, toxicity studies were performed in separate animals. Briefly, DM1-NO-NPs was injected at a dose of (260.8 nmol/kg) to normal balb/c mice. For comparison, saline or DM1 alone at the same concentration was injected. Blood samples were collected after 10 days and hematology tests were conducted. Complete blood count (CBC) shows that white blood cell (WBC), red blood cell (RBC), platelet (PLT), and plateletcrit (PCT) levels were all within normal ranges and were comparable to the PBS control (FIGS. 9A-9C). Alanine transaminase (ALT), aspartate transaminase (AST), bilirubin, and creatinine (CR) levels were also examined (FIGS. 8*a*-*c*). There was an increase of ALT level with DM1-NO-NPs relative to the saline control (FIG. 10A), but the difference was not significant (P=0.29). All the other indices were within normal ranges (Otto et al., *J. Am. Assoc. Lab. Anim. Sci.* 55, 375-386 (2016)) indicating little impact of the treatment on liver and kidney functions. ALT and AST levels were also analyzed in the liver tissues and found no significant difference between the DM1-NO-NPs+RT and PBS control groups either (FIG. 10D, 10E). Other markers including sodium, potassium, chloride, bicarbonate, magnesium, calcium, glucose, inorganic phosphate, and magnesium, cholesterol, albumin, and total protein levels were all within normal ranges (FIGS. 10G, 10G). Overall, these results confirmed the low toxicity of DM1-NO-NPs at the test dose.

The foregoing experiments exemplify preparation of DM1-NO, a nitrosylated maytansine analog, and encapsulation of it into PLGA-b-PEG nanoparticles for tumor delivery and sensitizing cancer cells to RT. While DM1 has potential as a radiosensitizer, it has seldom been investigated in the context of RT due to its high systematic toxicity. This problem is solved by using nanoparticle delivery and nitrosylation that suppresses the toxicity of the drug in the absence of radiation. Once delivered to tumors, external irradiation breaks the S—N bond and liberates DM1 as an anti-mitotic agent. The EPR-based drug delivery and the fact that radiation is confined to tumor areas lends high selectivity to the approach. While the current studies were performed in NSCLC models, the nanoparticles have great potential in treatment of other cancer types including, but not limited to, colorectal, brain, and breast cancer.

The functions of nitrosylation are at least two-fold. In addition to reducing the toxicity of DM1 in the absence of radiation, it also enhances the sensitivity of cancer cells to radiation therapy. Specifically, DM1-NO is released from nanoparticles in tumors and degraded under irradiation to release a highly reactive radical, NO. The latter can react with ROS, which are abundant in irradiated tumors, to form RNS such as peroxynitrites. With complementary radiosensitizing mechanisms, DM1 and NO synergize to improve RT outcomes. Both the NO release and its reaction with ROS are promoted under irradiation, which again can be delivered to tumors in a conformal manner in the clinic.

The foregoing experiments utilize PLGA-b-PEG nanoparticles, which are a well-established nanoplatform. Studies show good DM1-NO loading and controlled release of the drug. Meanwhile, DM1-NO as a small molecule can be potentially loaded onto other polymer-, liposome-, or micelle-based nanoparticles. It is also possible to load DM1-NO onto inorganic nanoparticles, including those having high-Z elements. High-Z nanoparticles are promising radiosensitizers for their large absorption cross-section for high-energy photons and the potential to increase energy deposition in tumors (Song et al., *Adv. Mater.* 29, 1700996 (2017)). For instance, Bi2S3 and Au—Bi2S3 nanoparticles have shown good dose modifying factors (Wang et al., *ACS Nano* 13, 5947-5958 (2019), Nosrati et al., *Sci. Eng.* 5, 4416-4424 (2019)). Gd bound silica nanoparticles and hafnium oxide nanoparticles are being tested in the clinic to enhance radiotherapy. The combination may further improve treatment outcomes. Aside from being a radiosensitizer, NO may have other impacts on tumor microenvironment (Salimian, *Trends Cancer* 3, 659-672 (2017)). For instance, NO may dilate blood vessels (Zhao et al., *J. Pharmacol. Sci.* 129, 83-94 (2015)), possibly making tumors more accessible to nanoparticles.

Example 5: Coupling $NTS_{mut}$ to the Nanoparticles Improves Tumor Accumulation

Materials and Methods

DM1-NO loaded PLGA nanoparticles were prepared by nanoprecipitation. Briefly, PLGA-COOH was dissolved in DMSO to a final polymer concentration of 5 mg/mL and was mixed with 1.5 mg/mL of DM1-NO. The mixture was dropwise added to pure water under vigorous stirring to produce nanoparticles. After purification, the NP solutions were resuspended in PBS (1×). The surface carboxyl groups were activated by EDC/NHS, and the nanoparticles were then reacted with $NTS_{mut}$ and p-$NH_2$-Bn-DOTA at a 5:1 mole ratio for coupling. The resulting nanoparticles were purified and labeled with $^{64}Cu$ for PET imaging. DM1-NO encapsulated PLGA nanoparticles coupled with $NTS_{mut}$ only were tested as a comparison. H1299 tumor bearing mice were i.v. injected with these nanoparticles (~100 μCi per mouse) and subjected to PET imaging at 1, 4, and 24 h.

Chemical Structures of Cys-$NTS_{mut}$:

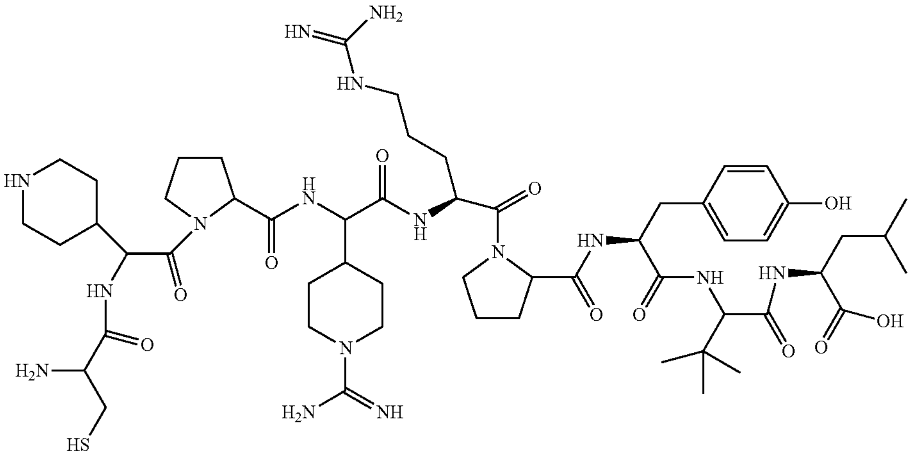

Cys-NTSmut

Results

While DM1-NO-PLGA NPs accumulated in tumors through the EPR effect, $NTS_{mut}$-DM1-NO PLGA NPs accumulated in tumors through both EPR and NTSR1 targeting. See FIG. 11.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A compound containing the structural motif:

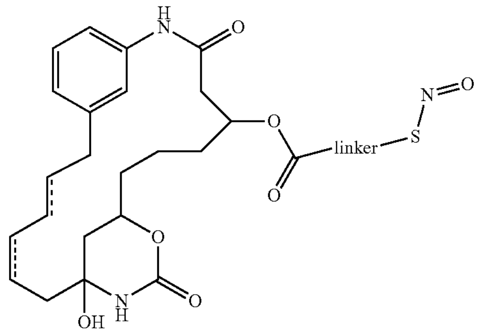

or

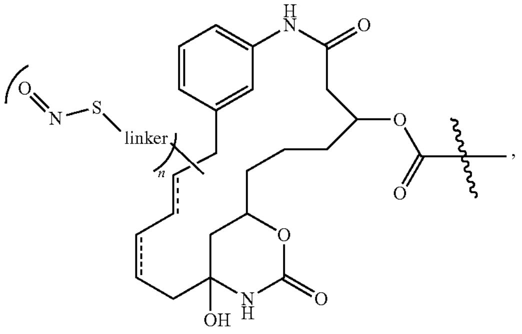

wherein:

n is an integer between 1 and 13, inclusive, the dashed lines indicate the presence of a bond or absence of a bond, and the corresponding carbon atoms have none, one, or two hydrogen atoms attached to each according to valency, and "linker" is, independently, substituted amido, unsubstituted amido, substituted alkyl, substituted alkylene, unsubstituted alkylene, substituted aryl, substituted heteroaryl, substituted alkenyl, substituted alkynyl, substituted alkoxy, substituted aroxy, substituted alkylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, substituted polyaryl, substituted $C_3$-$C_{20}$ cyclic, substituted $C_3$-$C_{20}$ heterocyclic, or absent.

2. The compound of claim 1, having the structure:

Formula I

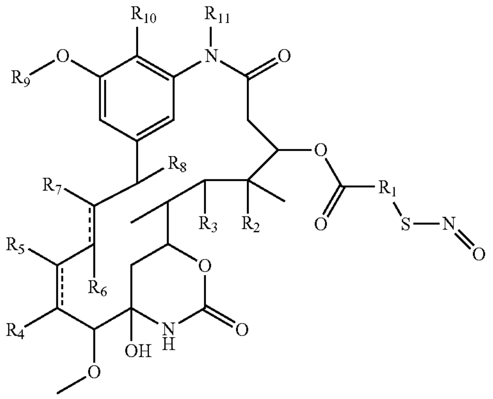

Formula I(a)

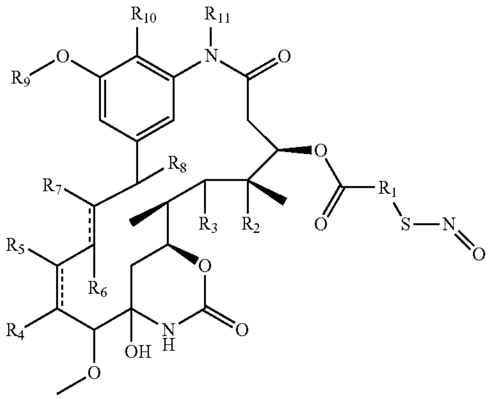

wherein:

$R_1$ is substituted amido, unsubstituted amido, substituted alkyl, substituted alkylene, unsubstituted alkylene, substituted aryl, substituted heteroaryl, substituted alkenyl, substituted alkynyl, substituted alkoxy, substituted aroxy, substituted alkylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, substituted polyaryl, substituted $C_3$-$C_{20}$ cyclic, or substituted $C_3$-$C_{20}$ heterocyclic, and $R_2$ and $R_3$ together with the carbon atoms to which they are bonded are an epoxide, or $R_2$, $R_3$, $R_4$, $R_5$, $R_6$, and $R_8$ are independently hydrogen, halogen, substituted alkyl, unsubstituted alkyl, substituted aryl, unsubstituted aryl, substituted heteroaryl, unsubstituted heteroaryl, unsubstituted alkenyl, substituted alkenyl, unsubstituted alkynyl, substituted alkynyl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic, $R_7$, $R_9$, and $R_{11}$ are independently unsubstituted alkyl, substituted alkyl, hydrogen, halogen, substituted aryl, unsubstituted aryl, substituted heteroaryl, unsubstituted heteroaryl, unsubstituted alkenyl, substituted alkenyl, unsubstituted alkynyl, substituted alkynyl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic, and $R_{10}$ is halogen, hydrogen, substituted alkyl, unsubstituted alkyl, substituted aryl, unsubstituted aryl, substituted heteroaryl, unsubstituted heteroaryl, unsubstituted alkenyl, substituted alkenyl, unsubstituted alkynyl, substituted alkynyl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic.

3. The compound of claim 2, wherein $R_1$ has the structure:

Formula II

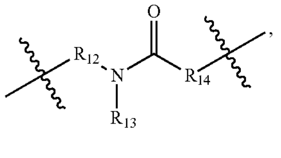

wherein $R_{12}$ is substituted $C_1$-$C_5$alkylene or unsubstituted $C_1$-$C_5$ alkylene, $R_{13}$ is hydrogen, substituted $C_1$-$C_5$alkyl, or unsubstituted $C_1$-$C_5$ alky, and $R_{14}$ is substituted $C_1$-$C_5$ alkylene or unsubstituted $C_1$-$C_5$ alkylene.

4. The compound of claim 3, having a structure selected from:

Formula III

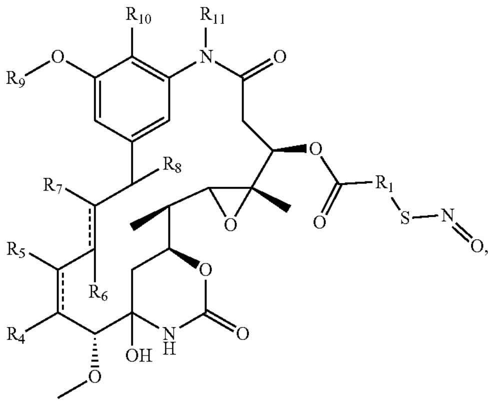

Formula IV

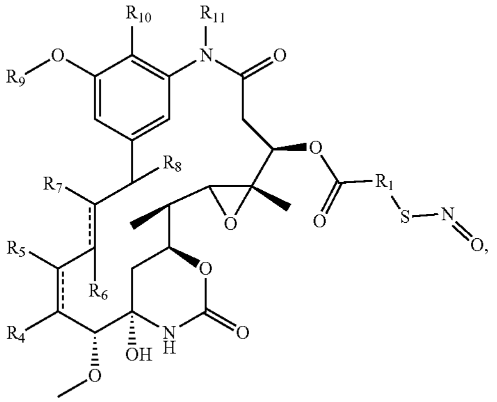

Formula V

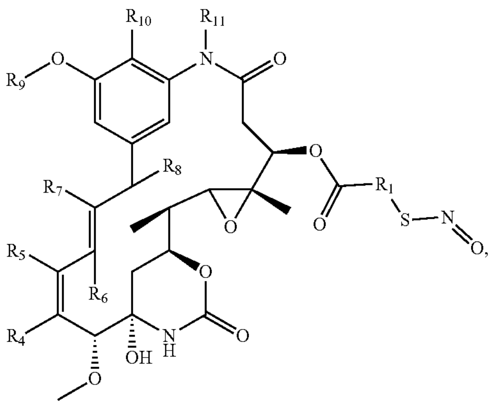

-continued

Formula VI

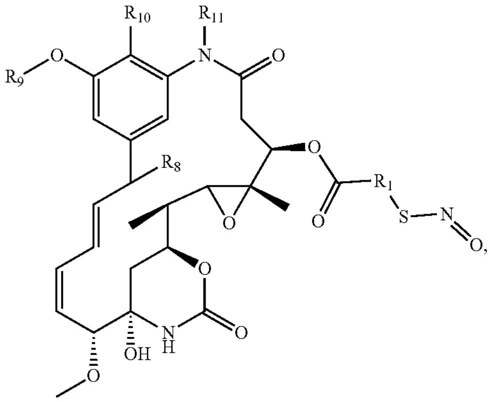

Formula VII

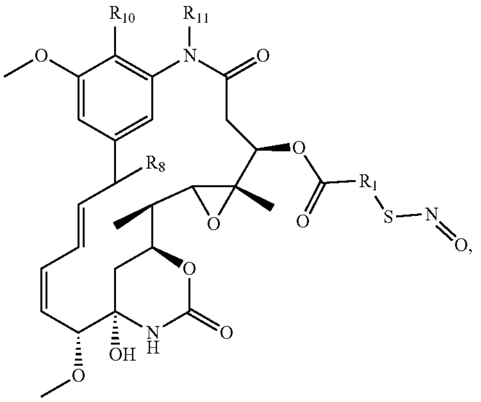

Formula VIII

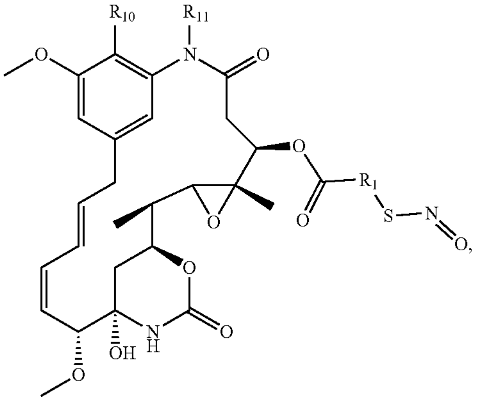

-continued

Formula IX

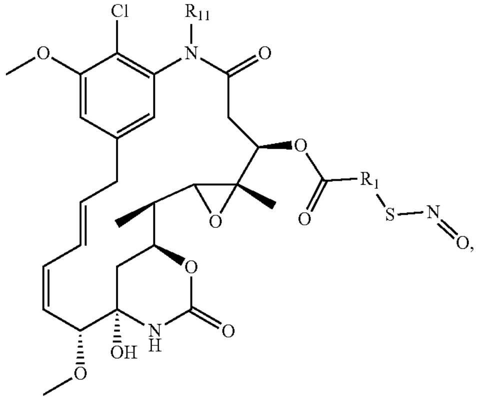

or

Formula X

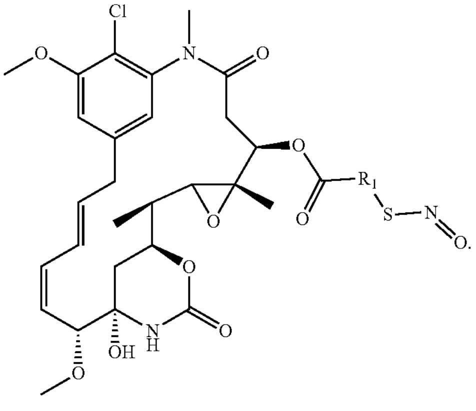

5. The compound of claim 4, wherein when present:

$R_4$, $R_5$, $R_6$, and $R_8$ are independently hydrogen, hydroxy, halogen, substituted $C_1$-$C_5$ alkyl, unsubstituted $C_1$-$C_5$ alkyl, substituted aryl, unsubstituted aryl, substituted heteroaryl, unsubstituted heteroaryl, unsubstituted $C_1$-$C_5$ alkenyl, substituted $C_1$-$C_5$ alkenyl, unsubstituted $C_1$-$C_5$ alkynyl, substituted $C_1$-$C_5$ alkynyl, unsubstituted $C_1$-$C_5$ alkoxy, substituted $C_1$-$C_5$ alkoxy, unsubstituted aroxy, substituted aroxy, unsubstituted $C_1$-$C_5$ alkylthio, substituted $C_1$-$C_5$ alkylthio, unsubstituted arylthio, substituted arylthio, unsubstituted $C_1$-$C_5$ carbonyl, substituted $C_1$-$C_5$ carbonyl, unsubstituted $C_1$-$C_5$ carboxyl, substituted $C_1$-$C_5$ carboxyl, unsubstituted $C_1$-$C_5$ amino, substituted $C_1$-$C_5$ amino, unsubstituted $C_1$-$C_5$ sulfonyl, substituted $C_1$-$C_5$ sulfonyl, unsubstituted $C_1$-$C_5$ sulfamoyl, substituted $C_1$-$C_5$ sulfamoyl, unsubstituted $C_1$-$C_5$ phosphonyl, substituted $C_1$-$C_5$ phosphonyl, unsubstituted polyaryl, substituted polyaryl, unsubstituted $C_3$-$C_6$ cyclic, substituted $C_3$-$C_6$ cyclic, unsubstituted $C_3$-$C_6$ heterocyclic, or substituted $C_3$-$C_6$ heterocyclic, $R_7$, $R_9$, and $R_{11}$ are independently unsubstituted $C_1$-$C_5$alkyl, substituted $C_1$-$C_5$ alkyl, hydrogen, hydroxy, halogen, substituted aryl, unsubstituted aryl, substituted heteroaryl, unsubstituted heteroaryl, unsubstituted $C_1$-$C_5$ alkenyl, substituted $C_1$-$C_5$ alkenyl, unsubstituted $C_1$-$C_5$ alkynyl, substituted $C_1$-$C_5$ alkynyl, unsubstituted $C_1$-$C_5$ alkoxy, substituted $C_1$-$C_5$ alkoxy, unsubstituted aroxy, substituted aroxy, unsubstituted $C_1$-$C_5$alkylthio, substituted $C_1$-$C_5$ alkylthio, unsubstituted arylthio, substituted arylthio, unsubstituted $C_1$-$C_5$ carbonyl, substituted $C_1$-$C_5$ carbonyl, unsubstituted $C_1$-$C_5$ carboxyl, substituted $C_1$-$C_5$ carboxyl, unsubstituted $C_1$-$C_5$ amino, substituted $C_1$-$C_5$ amino, unsubstituted $C_1$-$C_5$ sulfonyl, substituted $C_1$-$C_5$ sulfonyl, unsubstituted $C_1$-$C_5$ sulfamoyl, substituted $C_1$-$C_5$ sulfamoyl, unsubstituted $C_1$-$C_5$ phosphonyl, substituted $C_1$-$C_5$ phosphonyl, unsubstituted polyaryl, substituted polyaryl, unsubstituted $C_3$-$C_6$ cyclic, substituted $C_3$-$C_6$ cyclic, unsubstituted $C_3$-$C_6$ heterocyclic, or substituted $C_3$-$C_6$ heterocyclic, and $R_{10}$ is halogen, hydrogen, hydroxy, substituted $C_1$-$C_5$alkyl, unsubstituted $C_1$-$C_5$alkyl, substituted aryl, unsubstituted aryl, substituted heteroaryl, unsubstituted heteroaryl, unsubstituted $C_1$-$C_5$ alkenyl, substituted $C_1$-$C_5$ alkenyl, unsubstituted $C_1$-$C_5$ alkynyl, substituted $C_1$-$C_5$ alkynyl, unsubstituted $C_1$-$C_5$alkoxy, substituted $C_1$-$C_5$ alkoxy, unsubstituted aroxy, substituted aroxy, unsubstituted $C_1$-$C_5$alkylthio, substituted $C_1$-$C_5$ alkylthio, unsubstituted arylthio, substituted arylthio, unsubstituted $C_1$-$C_5$ carbonyl, substituted $C_1$-$C_5$ carbonyl, unsubstituted $C_1$-$C_5$ carboxyl, substituted $C_1$-$C_5$ carboxyl, unsubstituted $C_1$-$C_5$ amino, substituted $C_1$-$C_5$ amino, unsubstituted $C_1$-$C_5$ sulfonyl, substituted $C_1$-$C_5$ sulfonyl, unsubstituted $C_1$-$C_5$ sulfamoyl, substituted $C_1$-$C_5$ sulfamoyl, unsubstituted $C_1$-$C_5$ phosphonyl, substituted $C_1$-$C_5$ phosphonyl, unsubstituted polyaryl, substituted polyaryl, unsubstituted $C_3$-$C_6$ cyclic, substituted $C_3$-$C_6$ cyclic, unsubstituted $C_3$-$C_6$ heterocyclic, or substituted $C_3$-$C_6$ heterocyclic.

6. The compound of claim 5, wherein when present:

$R_4$, $R_5$, and $R_6$ are independently hydrogen, hydroxy, halogen, substituted $C_1$-$C_5$ alkyl, unsubstituted $C_1$-$C_5$ alkyl, substituted aryl, unsubstituted aryl, substituted heteroaryl, or unsubstituted heteroaryl, $R_7$ is unsubstituted $C_1$-$C_5$alkyl, substituted $C_1$-$C_5$ alkyl, hydrogen, hydroxy, halogen, substituted aryl, unsubstituted aryl, substituted heteroaryl, or unsubstituted heteroaryl.

7. The compound of claim 6, wherein when present $R_8$ is hydrogen, hydroxy, halogen, substituted $C_1$-$C_5$ carboxyl, unsubstituted $C_1$-$C_5$ carboxyl, substituted $C_1$-$C_5$ carbonyl, or unsubstituted $C_1$-$C_5$ carbonyl.

8. The compound of claim 7, wherein when present $R_9$ is unsubstituted $C_1$-$C_5$ alkyl, substituted $C_1$-$C_5$alkyl, hydrogen, substituted $C_1$-$C_5$ carbonyl, or unsubstituted $C_1$-$C_5$ Previously presented.

9. The compound of claim 8, wherein when present $R_{10}$ is a halogen, substituted $C_1$-$C_5$ alkyl, unsubstituted $C_1$-$C_5$ alkyl, substituted $C_1$-$C_5$ carbonyl, or unsubstituted $C_1$-$C_5$ carbonyl.

10. The compound of claim 9, wherein when present $R_{11}$ is hydrogen, substituted $C_1$-$C_5$alkyl, unsubstituted $C_1$-$C_5$ alkyl, substituted aryl, unsubstituted aryl, substituted heteroaryl, or unsubstituted heteroaryl.

11. The compound of claim 10, having the structure:

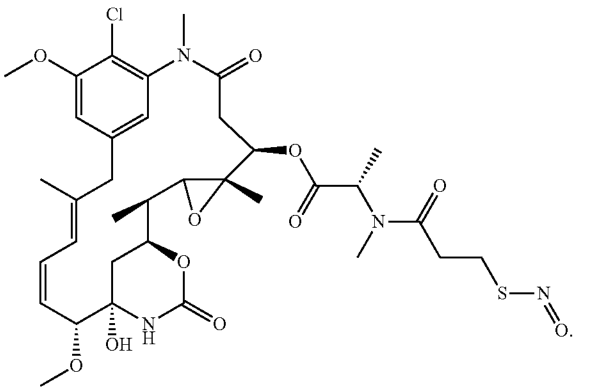 [SMILES: COc1cc2cc(c1Cl)N(C)C(=O)C[C@@H](OC(=O)[C@H](C)N(C)C(=O)CCSN=O)[C@]1(C)OC1[C@H](C)[C@@H]1C[C@@](O)(NC(=O)O1)[C@H](OC)/C=C\C=C(/C)C2]

12. A compound comprising an analog of a radiosensitizer parent compound comprising one or more S-nitrosothiol moieties, wherein the S—N bond of the S-nitrosothiol moiet(ies) is cleavable by radiation during radiotherapy and releases the parent compound and nitric oxide, optionally wherein the radiosensitizer parent compound is nicotinamide, metronidazole or an analog thereof, optionally selected from misoniszole, etanidazole, and nimorazole; a hypoxic cell cytotoxic agent, optionally selected from mitomycin-C and tirapazamine; a membrane active agent optionally selected from procaine, lidocaine, and chlorpromazine; a radiosensitizing nucleoside optionally selected from 5-fluorouracil, fluorodeoxyuridine bromodeoxyuridine, lododeoxyuridine, hydroxyurea, gemcitabine, and fludarabine, a texaphryin optionally selected from motexafin gadolinium; a suppressor of sulfhydral groups optionally selected from N-ethylmaleimide, diamide, and diethylmaleate; a chemotherapeutic agent optionally selected from paclitaxel, docetaxel, irinotecan, and cisplatin; pentoxifylline; vinorelbine; a PARP inhibitor; a histone deacetylase inhibitor; and a proteasome inhibitor.

13. A nanoparticle comprising the compound of claim 1, wherein the nanoparticle is a polymeric nanoparticle, liposome, or inorganic nanoparticle.

14. The nanoparticle of claim 13, wherein the nanoparticle is a polymeric nanoparticle comprising one or more amphiphilic, hydrophobic, and/or hydrophilic polymers.

15. The nanoparticle of claim 14, wherein one or more of the hydrophobic polymers is polyester.

16. The nanoparticle of claim 15, wherein the polyester or polyesters are selected from poly(lactic acid-co-glycolic acid)s, poly(lactic acid), poly(glycolic acid).

17. The nanoparticle of claim 16, wherein the nanoparticle comprises one or more hydrophilic polymers, optionally wherein one or more of the hydrophilic polymers are a polyalkylene glycol.

18. The nanoparticle of claim 17, wherein the nanoparticle is a polymeric nanoparticle comprising poly(lactide-co-glycolic)-block-poly(ethylene glycol) (PLGA-b-PEG).

19. The nanoparticle of claim 13, further comprising a targeting agent coupled thereto.

20. The nanoparticle of claim 19, wherein the targeting agent targets NTSR1, optionally wherein the targeting agent is NTS or a variant thereof.

21. The nanoparticle of claim 16 further comprising a targeting agent that targets NTSR1, wherein the compound is

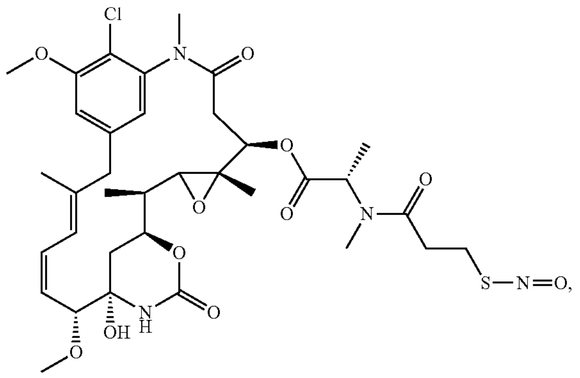

S-Nitroso-Mertansine (DM1-NO)

optionally the nanoparticle is a polymeric nanoparticle comprising poly(lactide-co-glycolic)-block-poly(ethylene glycol) (PLGA-b-PEG).

22. A pharmaceutical composition comprising an effective amount of the compound of claim 1 or nanoparticles comprising the same, and a pharmaceutically acceptable diluent or carrier.

* * * * *

SEQUENCE LISTING

<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (1)..(2)
<223> OTHER INFORMATION: X = any amino acid
<220> FEATURE:
<221> NAME/KEY: MISC_FEATURE
<222> LOCATION: (8)..(9)
<223> OTHER INFORMATION: X = any amino acid

<400> SEQUENCE: 1

Xaa Xaa Cys Asn Gly Arg Cys Xaa Xaa
1               5

<210> SEQ ID NO 2
<211> LENGTH: 11
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (2)..(3)
<223> OTHER INFORMATION: X= any amino acid
<220> FEATURE:
<221> NAME/KEY: MISC_FEATURE
<222> LOCATION: (4)..(4)
<223> OTHER INFORMATION: X= cysteine or any amino acid (C/X)
<220> FEATURE:
<221> NAME/KEY: MISC_FEATURE
<222> LOCATION: (8)..(8)

-continued

<223> OTHER INFORMATION: X= cysteine or any amino acid (C/X)
<220> FEATURE:
<221> NAME/KEY: MISC_FEATURE
<222> LOCATION: (9)..(10)
<223> OTHER INFORMATION: X= any amino acid

<400> SEQUENCE: 2

Cys Xaa Xaa Xaa Asn Gly Arg Xaa Xaa Xaa Cys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (6)..(11)
<223> OTHER INFORMATION: X= any amino acid

<400> SEQUENCE: 3

Cys Asn Gly Arg Cys Xaa Xaa Xaa Xaa Xaa Xaa
1               5                   10

<210> SEQ ID NO 4
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 4

Cys Arg Gly Arg Arg Ser Thr
1               5

<210> SEQ ID NO 5
<211> LENGTH: 13
<212> TYPE: PRT
<213> ORGANISM: Artificial Sequence
<220> FEATURE:
<223> OTHER INFORMATION: synthetic polypeptide

<400> SEQUENCE: 5

Gln Leu Tyr Glu Asn Lys Pro Arg Arg Pro Tyr Ile Leu
1               5                   10

<210> SEQ ID NO 6
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 6

Pro Arg Arg Pro Tyr Ile Leu
1               5